US007736886B2

(12) United States Patent
Puchta et al.

(10) Patent No.: US 7,736,886 B2
(45) Date of Patent: Jun. 15, 2010

(54) RECOMBINATION SYSTEMS AND METHODS FOR ELIMINATING NUCLEIC ACID SEQUENCES FROM THE GENOME OF EUKARYOTIC ORGANISMS

(75) Inventors: Holger Puchta, Karlsruhe (DE); Christian Biesgen, Quedlinburg (DE)

(73) Assignee: SunGene GmbH & Co. KGaA and Institut f. Pflanzengenetik u. Kulturpflanzenforschung (DE)

( * ) Notice: Subject to any disclaimer, the term of this patent is extended or adjusted under 35 U.S.C. 154(b) by 303 days.

(21) Appl. No.: 10/750,891

(22) Filed: Jan. 5, 2004

(65) Prior Publication Data
US 2005/0172365 A1  Aug. 4, 2005

Related U.S. Application Data

(63) Continuation-in-part of application No. PCT/EP02/07281, filed on Jul. 2, 2002.

(30) Foreign Application Priority Data
Jul. 4, 2001  (DE) .................... 101 31 786

(51) Int. Cl.
*C12N 1/00* (2006.01)
*C12N 15/87* (2006.01)
*C12N 1/12* (2006.01)
*C12N 15/74* (2006.01)

(52) U.S. Cl. .............. 435/254.11; 435/463; 435/257.2; 435/477; 435/478

(58) Field of Classification Search ............ None
See application file for complete search history.

(56) References Cited

U.S. PATENT DOCUMENTS

| 5,527,695 A | 6/1996 | Hodges et al. |
| 5,792,632 A | 8/1998 | Dujon et al. |
| 6,395,959 B1 * | 5/2002 | Dujon et al. ........... 800/18 |

FOREIGN PATENT DOCUMENTS

WO  WO 96/14408  5/1996

OTHER PUBLICATIONS

Lyznik et al. 1996, Nucleic Acids Research 24:3784-3789.*
Puchta, H., et al., "Two Different but related mechanisms are used in plants for the repair of genomic double-strand breaks by homologous recombination", Proc. Natl. Acad. Sci. USA, vol. 93, 1996, pp. 5055-5060.
Aggarwal, A., et al., "Novel site-specific DNA endonucleases", Current Opinion in Structural Biology, vol. 8, 1998, pp. 19-25.
Russell, S., et al. "Directed Excision of a Transgene from the Plant Genome", Mol. Genet. Genet. vol. 234, 1992, pp. 49-59.
Kilby, N., et al., "FLP Recombinase in Transgenic Plants: Constitutive Activity in Stably Transformed Tobacco and Generation of Marked Cell Clones in Arabidopsis", The Plant Journal, vol. 8, No. 5, 1995, pp. 637-652.
Onouchi, H., et al., "Visualization of Site-Specific Recombination Catalyzed by a Recombinase from *Zygosaccharomyces rouxii* in *Arabidopsis thaliana*", Mol. Gen. Genet. vol. 247, 1995, pp. 653-660.
Haber, J., "In Vivo Biochemistry: Physical Monitoring of Recombination Induced by Site-Specific Endonucleases", BioEssays, vol. 17, No. 7, 1995, pp. 609-620.
Puchta, H., "Use of I-Sce I to Induce DNA Double-Strand Breaks in Nicotiana", Chapter 36, in Methods in Molecular Biology, vol. 113, DNA Repair Protocols: Euroacryotic Systems, Henderson, D.S., ed., Humana Press Inc., NJ, USA, 1999, pp. 447-451.
Segal, D., et al., "Endonuclease-induced, Targeted Homologous Extrachromosomal Recombination in *Xenopus* Oocytes", Proc. Natl. Acad. Sci. USA, vol. 92, 1995, pp. 806-810.
Kuzminov, A., "Recombinational Repair of DNA Damage in *Escherichla coli* and Bacteriophageλ", Microbiology and Molecular Biology Reviews, vol. 63, No. 4, 1999, pp. 751-813.
Heifetz, P., et al., "Protein Expression in Plastids", Current Opinion in Plant Biology, vol. 4, 2001, pp. 157-161.
Mengiste, T., et al., "Prospects for the Precise Engineering of Plant Genomes by Homologous Recombination", Biol. Chem., vol. 380, 1999, pp. 749-758.
Hohn, B., et al., "Gene Therapy in Plants", Proc. Natl. Acad. Sci. USA, vol. 96, 1999, pp. 8321-8323.
Puchta, H., et al., "From CentiMorgans to Base Pairs: Homologous Recombination in Plants", Trends in Plant Science, vol. 1, No. 10, 1996, pp. 340-348.
Siebert, R., et al., "Efficient Repair of Genomic Double-Strand Breaks by Homologous Recombination between Directly Repeated Sequences in the Plant Genome", The Plant Cell, vol. 14, 2002, pp. 1121-1131.
Dale, E., et al., "Gene Transfer with Subsequent Removal of the Selection Gene from the Host Genome", Proc. Natl. Acad. Sci. USA, vol. 88, 1991, pp. 10558-10562.
Osborne, B., et al., "A System for Insertional Mutagenesis and Chromosomal Rearrangement Using the Ds Transposon and Cre-*lox*", The Plant Journal, vol. 7, No. 4, 1995, 687-701.
Lyznik, L.A., et al., "FLP-Mediated Recombination of *FRT* Sites in the Maize Genome", Nucleic Acids Research, vol. 24, No. 19, 1996, pp. 3784-3789.
Sugita, K., et al., "A transformation Vector for the Production of Marker-Free Transgenic Plants Containing a Single Copy Transgene at High Frequency", The Plant Journal, vol. 22, No. 5, 2000, pp. 461-469.

(Continued)

*Primary Examiner*—Anne Marie Grunberg
*Assistant Examiner*—Li Zheng
(74) *Attorney, Agent, or Firm*—Connolly Bove Lodge & Hutz LLP

(57) ABSTRACT

The invention relates to recombination systems and methods for eliminating nucleic acid sequences from the chromosomal DNA of eukaryotic organisms, and to transgenic organisms—preferably plants—which comprise these systems or were generated using these methods.

29 Claims, 15 Drawing Sheets

OTHER PUBLICATIONS

Jasin, M., "Genetic Manipulation of Genomes with Rare-Cutting Endonucleases", TIG, vol. 12, No. 6, 1996, pp. 224-228.

Bibikova, M., et al., "Stimulation of Homologous Recombination through Targeted Cleavage by Chimeric Nucleases", Molecular and Cellular Biology, vol. 21, No. 1, 2001, pp. 289-297.

Posfai, G., et al., "Markerless Gene Replacement in *Escherichia coli* Stimulated by a Double-Strand Break in the Chromosome", Nucleic Acids Research, vol. 27, No. 22, 1999, pp. 4409-4415.

Dürrenberger, F. et al., "Double Strand Break-Induced Recombination in *Chlamydomonas reinhardtii* Chloroplasts", Nucleic Acids Research, vol. 24, No. 17, 1996, pp. 3323-3331.

Kanaar, R., et al., "Recombination and Joining: Different Means to the Same Ends", Genes and Function, vol. 1, No. 3, 1997, pp. 165-174.

Vergunst, A.C., et al., "Recombination in the Plant Genome and its Application in Biotechnology", Critical Reviews in Plant Sciences, vol. 18, No. 1, 1999, pp. 1-31.

Roth, D., et al., "Illegitimate Recombination in Mammalian Cells", Chapter 21 in Genetic Kucherlapatl, R., et al., eds., Washington, 1988, pp. 621-635.

Puchta, H., "Removing Selectable Marker Genes: Taking the Shortcut", Trends in Plant Science, vol. 5, No. 7, 2000, p. 273-274.

* cited by examiner

A

B

RECOMBINATION SYSTEMS AND METHODS FOR ELIMINATING NUCLEIC ACID SEQUENCES FROM THE GENOME OF EUKARYOTIC ORGANISMS

RELATED APPLICATIONS

This application is a continuation-in-part application of International Application PCT/EP02/07281, with an international filing date of Jul. 2, 2002, now abandoned, which claims priority to German application no. DE 10131786.7 filed Jul. 4, 2001.

BACKGROUND

1. Field of the Invention

The invention relates to recombination systems and methods for eliminating nucleic acid sequences from the genome of eukaryotic organisms, and to transgenic organisms—preferably plants—comprising these systems.

2. Description of the Background

The purpose of biotechnological research into organisms consists in, inter alia, obtaining commercially utilizable information on the function of certain genes and gene products and the elucidation of biosynthetic pathways or disease mechanisms. The information obtained in this manner can be employed in a multiplicity of ways. They serve for example for the production of novel medicaments, the development of alternative, biotechnological production methods or the generation of modified plants. An aim of biotechnological research into plants is the generation of plants with advantageous novel characteristics, for example for increasing agricultural productivity, improving the quality in foodstuffs or for the production of certain chemicals or pharmaceuticals (Dunwell J M, J Exp Bot. 2000; 51 Spec No: 487-96).

In the generation of transgenic organisms, selection of the organisms which have been modified in the desired manner is required owing to the poor efficacy of the methods used (such as, for example, stable transformation or, in particular, homologous recombination). Transgenic plants can be generated by a series of techniques (Review: Potrykus I. and Spangenberg G. ed. (1995) *Gene transfer to plants*. Springer, Berlin). In particular the gene transfer mediated by *Agrobacterium tumefaciens* and the bombardment of plant cells with the particle gun play an important role in this context. An important problem is the fact that transgenic DNA, once stably introduced into an organism, can only be removed with difficulty. The genes for resistance to antibiotics or herbicides, which are used during the transformation procedure for selection purposes, remain in the transgenic plants, which contributes substantially to the lack of acceptance of these "gene food" products among consumers.

It has therefore been attempted for some time to develop techniques by means of which foreign DNA can be integrated into the plant genome at the specific sites or reexcised therefrom (Ow D W and Medberry S L (1995) Crit Rev in Plant Sci 14:239-261).

The skilled worker is familiar with a variety of systems for the site-directed removal of recombinantly introduced nucleic acid sequences. They are based on the use of sequence—specific recombinases and two recognition sequences of said recombinases which flank the sequence to be removed. The effect of the recombinase on this construct brings about the excision of the flanked sequence, one of the recognition sequences remaining in the genome of the organism. Various sequence-specific recombination systems are described, such as the Cre/lox system of the bacteriophage P1 (Dale E C and Ow D W (1991) Proc Natl Acad Sci USA 88:10558-10562; Russell S H et al. (1992) Mol Gene Genet 234: 49-59; Osborne B I et al. (1995) Plant J. 7, 687-701), the yeast FLP/FRT system (Kilby N J et al. (1995) Plant J 8:637-652; Lyznik L A et al. (1996) Nucleic Acids Res 24:3784-3789), the Mu phage Gin recombinase, the *E. coli* Pin recombinase or the R/RS system of the plasmid pSR1 (Onouchi H et al. (1995) Mol. Gen. Genet. 247:653-660; Sugita K et al. (2000) Plant J. 22:461-469). Here, the recombinase (for example Cre or FLP) interacts specifically with its corresponding recombination sequences (34 bp lox sequence and 47 bp FRT sequence, respectively) in order to delete or invert the interposed sequences. Reports on successful applications of these systems in plants are limited. Thus, David Ow's group has demonstrated that a selection marker used for the transformation of plants which was flanked by two lox sequences can be reexcised from the plant genome by the expression of Cre (Dale E C and Ow D W (1991) Proc Natl Acad Sci USA 88:10558-10562). A disadvantage of the sequence-specific recombination systems is the reversibility of the reaction, that is to say an equilibrium exists between excision and integration of the marker gene in question. This frequently brings about the selection of mutations, i.e. as soon as a mutation blocks the further interaction of the lox recognition sequences with the enzyme, the (undesired) product is removed from the equilibrium and fixed. This not only applies to the Cre-lox system, but also to the other sequence-specific recombinases (see above). A further disadvantage is the fact that one of the recognition sequences of the recombinase remains in the genome, which is thus modified. This may have effects on the characteristics of the organisms when, for example, the recognition sequence modifies or destroys reading frames or genetic control elements such as promotors or enhancers. Furthermore, the recognition sequence which remains in the genome excludes a further use of the recombination system, for example for a second genetic modification, since interactions with the subsequently introduced recognition sequences cannot be ruled out. Substantial chromosomal rearrangements or deletions may result.

Zubko et al. describe a system for the deletion of nucleic acid sequences from the tobacco genome, where the sequence to be deleted is flanked by two 352 bp attP recognition sequences from the bacteriophage Lambda. Deletion of the flanked region takes place independently of the expression of helper proteins in two of eleven transgenic tobacco lines by spontaneous intrachromosomal recombination between the attP recognition regions. The disadvantages of this method are that recombination, or deletion, cannot be induced specifically at a particular point in time, but takes place spontaneously. The fact that the method worked only in a small number of lines suggests that the integration locus in the cases in question tends to be unstable (Puchta H (2000) Trends in Plant Sci 5:273-274).

On page 12 in the key to FIG. 32, WO 96/14408 describes a method for eliminating a genetic locus in which in each case one recognition sequence of the homing restriction endonuclease I-SceI is inserted at the respective end of the sequence to be deleted. Treatment with the endonuclease leads to double-strand breaks at both ends of the sequence to be deleted. The free ends then join up by means of "recombination". The "recombination" cited here can only be an illegitimate recombination—as can also be seen from the Figure—(for example a non-homologous end-joining (NHEJ) event), since no homologous sequences exist at the two remaining ends of the genomic DNA. Illegitimate recombination, however, leads to unpredictable recombination events. This may have effects on the characteristics of the organisms if for example reading frames or genetic control elements such as promotors or enhancers are modified or destroyed thereby. The system requires two recognition sequences which flank the fragment to be deleted.

The generation of sequence-specific double-strand breaks with the aid of restriction enzymes in eukaryotic genomes such as yeast (Haber J E (1995) Bioassays 17:609-620), mammalian cells (Jasin M (1996) Trends Genet. 12:224-228) or plants (Puchta H (1 999a) Methods Mol Biol 113:447-451) is described.

What is described is the induction of an intramolecular recombination on a plasmid DNA in *Xenopus* oocytes by sequence-specific cleavage with the endonuclease I-SceI (Segal D J and Caroll D (1995) Proc Natl Acad Sci USA 92:806-810) or by synthetic, chimeric nucleases (Bibikova M et al. (2001) Mol Cell Biol 21(1):289-297). The aim is the site-directed recombination between two homologous sequences between which a suitable nuclease cleavage site is located. Both cases are extrachromosomal recombination events in which in each case only part of the extra chromosomal plasmid DNA undergoes homologous recombination.

Posfai et al. describe a method for exchanging genes in the prokaryote *E.coli* (Posfai G et al. (1999) Nucleic Acids Res 27(22):4409-4415). Here, recombination between the endogenous and the mutated gene results in the *E.coli* genome, induced by cleavage with the restriction enzyme I-SceI. Aim and object was the exchange of an endogenous gene for a mutated transgene. Recombinations in *E.coli* proceed in a markedly simpler way and with greater efficacy than in higher eukaryotes (for example described by Kuzminov A (1999) Microbiol Mol Biol Rev. 63(4):751-813).

Dürrenberger et al. describe the induction of recombination in chloroplasts of the single-celled green alga *Chlamydomonas reinhardtii* using the I-SceI homing endonuclease (Dürrenberger F et al. (1996) Nucleic Acid Res 24(17):3323-3331). Recombination takes place between the endogenous 23S gene and an inserted 23S cDNA which contains a I-SceI cleavage site. Double-strand breaks are induced by mating the transgenic organism in question with an organism expressing I-SceI. Recombinations in chloroplasts proceed in a markedly simpler manner and with greater efficacy than in the chromosomal DNA of higher eukaryotes. Thus, indeed, homologous recombination appears to be the preferred, normal way of DNA integration in plastids (chloroplasts) (described in: Heifetz P B and Tuttle A M (2001) Curr Opinion Plant Biol 4:157-161). It appears that plastids have a specific system which enables them to undergo homologous recombination, as opposed to the nucleus, and facilitates the site-directed introduction of foreign DNA (Heifetz P B (2000) Biochimie 82:655-666).

The gene targeting technique, in which a site-directed integration into the chromosomal DNA of the host organism is to be achieved by means of homologous recombination works acceptably well only in the case of prokaryotes and yeast. The generation of corresponding transgenic organisms is possible in a few species only (such as, for example, mice) and even then highly complicated (see also Kanaar R Hoeijmakers J H (1997) Genes Funct 1(3):165-174). The existing, poor homologous recombination efficacy (approx. $1:1\times10^6$) is compensated for in this case by the use of complicated, sophisticated selection techniques which are limited to the species in question (such as, for example, "ES" cell technology). In other species—but above all in Higher Plants—such technologies have not been established as yet (Mengiste T and Paszkowski J (1999) Biol Chem. 380:749-758; Vergunst A C and Hooykaas P J J (1999) Crit Rev Plant Sci 18:1-31; Puchta H (1999) Methods Mol Biol 113:447-451; Hohn B and Puchta H (1999) Proc Natl Acad Sci USA 96:8321-8323). Attempts to achieve homologous recombination in plants resulted in random, nonhomologous "illegitimate" insertion events in most cases. Here, the DNA introduced is integrated at one or more unpredictable sites in the plant genome. Integration takes place by means of illegitimate recombination (Roth D B and Wilson J H (1988) illegitimate recombination in mammalian cells. In "Genetic recombination", R. Kucherlapati and G. R. Smith Edts., American Society of Microbiology, Washington, USA; pp.621-635) and not in sequence regions which are homologous to the transferred DNA (Puchta H and Hohn B (1996) Trends Plant Sci. 1:340-348). The problem of lacking efficacy in homologous recombination, which is serious predominantly in plants, is generally known to the skilled worker. The causes are addressed by current research (Review article: Mengiste T and Paszkowski J (1999) Biological Chemistry 380(7-8):749-58). Increasing the efficacy of homologous recombination has long been a need in plant biotechnology which is hitherto unresolved.

A further need which has long existed in biotechnological research and which is not addressed by any of the established systems is the provision of systems and methods which enables the site-directed elimination of nucleic acid sequences from the chromosomal DNA of a eukaryotic organism and allow the repeated application to the same organism. For example, it is an aim of plant biotechnology further to improve by means of recombinant methods existing high-yielding varieties. In this context, it is particularly important to eliminate, after the transformation has taken place, superfluous transgene sequences such as selection markers. In addition, methods for the predictable elimination of sequences, for example from the chromosomal DNA of an organism, would offer further applications in the field of genetic engineering which are of great interest scientifically and economically.

SUMMARY OF THE INVENTION

The present invention is directed to systems and methods that enable the predictable elimination of defined nucleic acid sequences from the chromosomal DNA of a eukaryotic organism and allow the repeated, successive application to the same organism. This invention was achieved in a surprising manner by providing the recombination system according to the invention.

One embodiment of the invention is directed to recombination systems for eliminating DNA sequences from the chromosomal DNA of eukaryotic cells or organisms, which comprises, in a eukaryotic cell or organism, a transgenic recombination construct inserted into the chromosomal DNA of a eukaryotic organism comprising a sequence consisting, in the 5'/3'-direction, of a first homology sequence A and at least one recognition sequence for the site-directed induction of DNA double-strand breaks and a second homology sequence B, the homology sequences A and B having a sufficient length and sufficient homology in order to ensure homologous recombination, together with an enzyme suitable for inducing DNA double-strand breaks at the recognition sequence (b1) for the site-directed induction of DNA double-strand breaks or a nucleic acid sequence encoding an enzyme suitable for inducing DNA double-strand breaks at the recognition sequence (b1).

Another embodiment of the invention is directed to methods for eliminating DNA sequences from chromosomal DNA of eukaryotic cells or organisms, which comprises combining, in a eukaryotic cell or organism, a transgenic recombination construct inserted into the chromosomal DNA of a eukaryotic organism comprising a sequence consisting, in the 5'- to 3'-orientation, of a first homology sequence A and at least one recognition sequence for the site-directed induction of DNA double-strand breaks and a second homology sequence B, the homology sequences A and B having a sufficient length and sufficient homology in order to ensure homologous recombination, together with an enzyme suitable for inducing DNA double-strand breaks at the recognition sequence (b1) for the site-directed induction of DNA double-strand breaks, and the induction of DNA double-strand breaks at the recognition sequence for the site-directed induction of DNA double-strand breaks and the homologous recombination taking place between the homology sequences A and B.

Other embodiments and advantages of the invention are set forth in part in the description, which follows, and in part, may be obvious from this description, or may be learned from the practice of the invention.

DESCRIPTION OF THE FIGURES

FIG. 7. Diagrams of exemplary embodiments of the invention.

DESCRIPTION OF THE INVENTION

Figure 1:
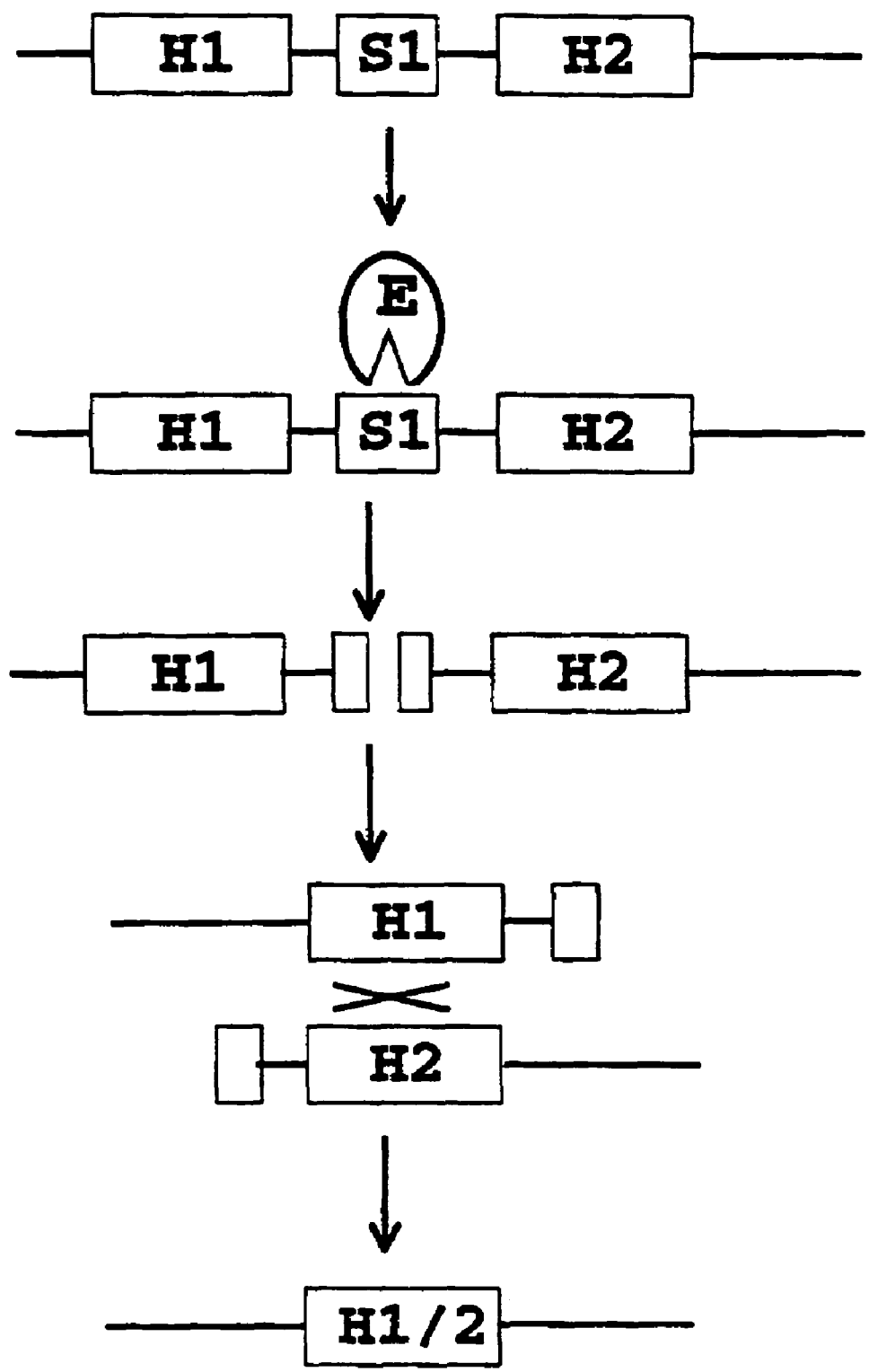
FIG. 1. Diagram of a principal of the invention.

As embodied and broadly described herein, the present invention is directed to systems and methods that enable the predictable elimination of defined nucleic acid sequences from the chromosomal DNA of a eukaryotic organism. The invention enables sequences (for example selection markers such as genes for resistance to antibiotics or herbicides) to be deleted from the chromosomal DNA of an organism in an accurately predictable manner. In doing so, the sequence to be eliminated is flanked by recognition sequences for the site-directed induction of DNA double-strand breaks (for example recognition sequences of rare-cleaving restriction enzymes) and combined with homologous sequences in the region of the cleavage sites. A double-strand break is induced by an enzyme suitable for inducing DNA double-strand breaks at the recognition sequence for the site-directed induction of DNA double-strand breaks (for example a sequence-specific nuclease), which, in consequence, triggers the homologous recombination of homologous sequences located at the break, and thus the deletion of any nucleic acid sequences located between the sequences. The recognition sequence for the site-directed induction of DNA double-strand breaks is likewise deleted, and the method can thus be used repeatedly for further controlled genetic modifications.

Surprisingly, this induced homologous recombination takes place with high efficacy and precision, which is in contrast to previous experience in the field of homologous recombination, including in plants. The frequency can be compared with the parallel, nonhomologous events (for example non-homologous end-joining events) (cf. Example 5). This is a remarkable finding which is in contrast to earlier observations, according to which the frequency of homologous recombination—above all in the case of plants—is secondary, almost negligible, in comparison with the "illegitimate" events.

The sequences which are deleted are those located between the homology sequences A and B. In contrast to systems such as, for example, the cre/lox or the FRT/FLP system, one is not bound to specific sequences when performing recombination. The skilled worker knows that any sequence can undergo homologous recombination with another sequence provided that sufficient length and homology exist. Owing to the sequence-specific induction of the double-strand breaks, the homologous recombination efficacy between the homology sequences A and B is increased considerably, indeed enabled in the first place in some cases.

With regard to the recombination construct, "transgene" refers to all those constructs which are the result of recombinant methods in which either a) at least one of the homology sequences A or B, or b) at least one recognition sequence for the site directed induction of DNA double-strand breaks, or c) (a) and (b)

are not located in their natural genetic environment (for example at their natural chromosomal locus) or have been modified by recombinant methods, it being possible for the modification to encompass, for example, substitutions, additions, deletions, inversion or insertions of one or more nucleotide residues.

"Eukaryotic cell or organism" generally refers to any eukaryotic cell or organism and to cells, tissues, parts or propagation material (such as seeds or fruits) derived from these in which an induction of double-strand breaks may take place at the recognition sequence for the site-directed induction of DNA double-strand breaks and the homologous recombination between the homology sequences A and B may take place while the recombination construct and the enzyme suitable for inducing DNA double-strand breaks at the recognition sequence for the site-directed induction of DNA double-strand breaks are simultaneously present in one reaction space (for example in a cell or cell compartment). A particularly preferred embodiment encompasses compartments of a eukaryotic cell such as, for example, the nucleus.

Cells or organisms that are especially preferably encompassed are those which constitute a multi-celled eukaryotic organism or are derived from the latter, and cells, tissues, parts or propagation material (such as seeds or fruits) of same. Very especially preferably encompassed cells or organisms are those which constitute an animal or plant organism or are derived from the latter, and cells, tissues, parts or propagation material of same. Most preferably encompassed cells or organisms are those which constitute a plant organism or are derived from the latter, and cells, tissues, parts or propagation material of same. Preferred genera and species are detailed further below.

Referring to the homology sequences A and B, "sufficient length" preferably refers to sequences with a length of at least 20 base pairs, preferably at least 50 base pairs, especially preferably at least 100 base pairs, very especially preferably at least 250 base pairs, most preferably at least 500 base pairs.

Referring to the homology sequences A and B, "sufficient homology" preferably refers to sequences with at least 70%, preferably 80%, by preference at least 90%, especially preferably at least 95%, very especially preferably at least 99%, most preferably 100%, homology within these homology sequences over a length of at least 20 base pairs, preferably at least 50 base pairs, especially preferably at least 100 base pairs, very especially preferably at least 250 base pairs, most preferably at least 500 base pairs.

Homology between two nucleic acid sequences is understood as meaning the identity of the nucleic acid sequence over in each case the entire sequence length which is calculated by alignment with the aid of the program algorithm GAP (Wisconsin Package Version 10.0, University of Wisconsin, Genetics Computer Group (GCG), Madison, USA), setting the following parameters:

| Gap Weight: 12 | Length Weight: 4 |
|---|---|
| Average Match: 2,912 | Average Mismatch: −2,003 |

In a preferred embodiment, only one recognition sequence for the site-directed induction of DNA double-strand breaks is located between the homology sequences A and B, so that the recombination construct employed in the recombination system or method according to the invention is constructed in the 5'- to 3'-orientation as follows:

a1) a first homology sequence A, and b1) a recognition sequence for the site-directed induction of DNA double-strand breaks, and a2) a second homology sequence B, the homology sequences A and B having a sufficient length and sufficient homology in order to ensure homologous recombination.

In a preferred embodiment, a further nucleic acid sequence is located between the homology sequences A and B, so that the recombination construct employed in the recombination system or method according to the invention is constructed as follows in the 5'/3'-direction of:

a1) a first homology sequence A, and b1) a recognition sequence for the site-directed induction of DNA double-strand breaks, and c) a further nucleic acid sequence, and a2) a second homology sequence B, the homology sequences A and B having a sufficient length and sufficient homology in order to ensure homologous recombination.

The recognition sequence for the site-directed induction of DNA double-strand breaks may also be located after or within the further nucleic acid sequence.

In a further preferred embodiment, a second recognition sequence for the site-directed induction of double-strand breaks is present after the further nucleic acid sequence. This embodiment is advantageous in particular in the case of homology sequences A and B which are further apart, or in the case of longer further nucleic acid sequences, since recombination efficacy is increased. In this embodiment, the recombination construct employed in the recombination system or method according to the invention is constructed as follows in a 5'- to 3'-orientation of:

a1) a first homology sequence A, and b1) a first recognition sequence for the site-directed induction of DNA double-strand breaks, and c) a further nucleic acid sequence, and b2) a second recognition sequence for the site-directed induction of DNA double-strand breaks, and a2) a second homology sequence B, the homology sequences A and B having a sufficient length and sufficient homology in order to ensure homologous recombination.

Furthermore, other recognition sequences may also be present between the homology sequences A and B, in addition to the second recognition sequences for the site-directed induction of DNA double-strand breaks. The individual recognition sequences (for example b1 or b2) for the site-directed induction of DNA double-strand breaks may be identical or different, i.e. they may act as recognition sequence for an individual enzyme for the site-directed induction of DNA double-strand breaks or else for a variety of enzymes. Here, the embodiment in which the recognition sequences for the site-directed induction of DNA double-strand breaks act as recognition sequence for an individual enzyme for the site-directed induction of DNA double-strand breaks is preferred in this context.

The skilled worker is familiar with a variety of ways to obtain one of the recombination constructs according to the invention. They can be prepared by means of customary recombination and cloning techniques as are described, for example, in T. Maniatis, E. F. Fritsch and J. Sambrook, Molecular Cloning: A Laboratory Manual, Cold Spring Harbor Laboratory, Cold Spring Harbor, N.Y. (1989), in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

Preferably, the recombination construct according to the invention is generated by joining the abovementioned essential constituents of the recombination construct together in the abovementioned sequence using the recombination and cloning techniques with which the skilled worker is familiar, and the result is then introduced into the chromosomal DNA of a host organism.

However, the skilled worker is aware that he may also obtain the recombination construct according to the invention in other ways. Thus, the host organism may already comprise one or more of the essential components of the recombination construct. The recombination construct according to the invention is then generated by introducing one further, or more, essential components of the recombination construct in the correct position relative to the existing components in said organism. Thus, for example, the starting organism may already comprise one of the homology sequences A or B. If the organism already comprises a homology sequence A, introducing a construct consisting of a recognition sequence for the site-directed induction of DNA double-strand breaks and a second homology sequence B after the homology sequence A gives rise to one of the recombination constructs according to the invention.

Furthermore, the skilled worker is familiar with various ways in which the recombination construct according to the invention may be introduced into the chromosomal DNA of a eukaryotic cell or organism. In this context, the insertion may be directed (i.e. taking place at a defined insertion site) or undirected (i.e. taking place randomly). Suitable techniques are known to the skilled worker and described by way of example herein.

"Enzyme suitable for inducing DNA double-strand breaks in the recognition sequence for the site-directed induction of DNA double-strand breaks" (herein "DSBI enzyme", which stands for "double strand-break inducing enzyme") generally refers to all those enzymes which are capable of generating double-strand breaks in double stranded DNA in a sequence-specific manner. The following may be mentioned by way of example, but not by limitation:

1. Restriction endonucleases (type II), preferably homing endonucleases as described in detail herein.
2. Recombinases (such as, for example, Cre/lox; R-RS; FLP/FTR as described above).
3. Transposases, for example the P-element transposase (Kaufman P D and Rio D C (1992) Cell 69(1):27-39) or AcDs (Xiao Y L and Peterson T (2000) Mol Gen Genet 263(1):22-29). In principle, all transposases or integrases are suitable as long as they have sequence specificity (Haren L et al. (1999) Annu Rev Microbiol. 1999; 53:245-281; Beall E L, Rio D C (1997) Genes Dev. 11(16):2137-2151).
4. Chimeric nucleases as described in detail herein.
5. Enzymes which induce double-strand breaks in the immune system, such as the RAG1/RAG2 system (Agrawal A et al. (1998) Nature 394(6695):744-451).
6. Group II intron endonucleases. Modifications of the intron sequence allows group II introns to be directed to virtually any sequence in a double-stranded DNA, where group II introns can subsequently insert by means of a reverse splice mechanism (Mohr et al. (2000) Genes & Development 14:559-573; Guo et al. (2000) Science 289:452-457). During this reverse splice mechanism, a double-strand break is introduced into the target DNA, the excised intron RNA cleaving the sense strand while the protein portion of the group II intron endonuclease hydrolyses the antisense strand (Guo et al. (1997) EMBO J 16: 6835-6848). If it is only desired to induce the double-strand break without achieving complete reverse splicing, as is the case in the present invention, it is possible to resort to, for example, group II intron endonucleases which lack the reverse transcriptase activity. While this does not prevent the generation of the double-strand break, the reverse splicing mechanism cannot proceed to completion. Suitable enzymes are not only natural enzymes, but also synthetic enzymes.

Preferred enzymes are all those DSBI enzymes whose recognition sequence is known and which can either be obtained in the form of their proteins (for example by purification) or expressed using their nucleic acid sequence. Especially preferred are restriction endonucleases (restriction enzymes) which have no or only a few recognition sequences—besides the recognition sequences present in the transgenic recombination construct—in the chromosomal DNA sequence of a particular eukaryotic organism. This avoids further double-strand breaks at undesired loci in the genome.

This is why homing endonucleases are very especially preferred (Review: (Belfort M and Roberts R J (1997) Nucleic Acids Res 25: 3379-3388; Jasin M (1996) Trends Genet. 12:224-228; Internet: http://rebase.neb.com/rebase/rebase.homing.html). Owing to their long recognition sequences, they have no, or only a few, further recognition sequences in the chromosomal DNA of eukaryotic organisms in most cases.

The sequences encoding for such homing endonucleases can be isolated for example from the chloroplast genome of *Chlamydomonas* (Turmel M et al. (1993) J Mol Biol 232: 446-467). They are small (18 to 26 kD) and their open reading frame (ORF) has a "coding usage" which is suitable directly for nuclear expression in eukaryotes (Monnat R J Jr et al. (1999) Biochem Biophys Res Com 255:88-93). Homing endonucleases which are very especially preferably isolated are the homing endonucleases I-SceI (WO96/14408), I-SceII (Sarguiel B et al. (1990) Nucleic Acids Res 18:5659-5665), I-SceIII (Sarguiel B et al. (1991) Mol Gen Genet. 255:340-341), I-CeuI (Marshall (1991) Gene 104:241-245), I-CreI (Wang J et al. (1997) Nucleic Acids Res 25: 3767-3776), I-ChuI (Cote V et al.(1993) Gené 129:69-76), I-TevI (Chu et al. (1990) Proc Natl Acad Sci USA 87:3574-3578; Bell-Pedersen et al. (1990) Nucleic Acids Res18:3763-3770), I-TevII (Bell-Pedersen et al. (1990) Nucleic Acids Res18: 3763-3770), I-TevIII (Eddy et al. (1991) Genes Dev. 5:1032-1041), Endo SceI (Kawasaki et al. (1991) J Biol Chem 266: 5342-5347), I-CpaI (Turmel M et al. (1995a) Nucleic Acids Res 23:2519-2525) and I-CpaII (Turmel M et al. (1995b) Mol. Biol. Evol. 12, 533-545).

Further homing endonucleases are detailed in the above-mentioned Internet website, and examples which may be mentioned are homing endonucleases such as F-SceI, F-SceII, F-SuvI, F-TevI, F-TevII, I-AmaI, I-AniI, I-CeuI, I-CeuAIIP, I-ChuI, I-CmoeI, I-CpaI, I-CpaII, I-CreI, I-CrepsbIP, I-CrepsbIIP, I-CrepsbIIIP, I-CrepsbIVP, I-CsmI, I-CvuI, I-CvuAIP, I-DdiI, I-DdiII, I-DirI, I-DmoI, I-HmuI, I-HmuII, I-HspNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PpbIP, I-PpoI, I-SPBetaIP, I-ScaI, I-SceI, I-SceII, I-SceIII, I-SceIV, I-SceV, I-SceVI, I-SceVII, I-SexIP, I-SneIP, I-SpomCP, I-SpomIP, I-SpomIIP, I-SquIP, I-Ssp6803I, I-SthPhiJP, I-SthPhiST3P, I-SthPhiS3bP, I-TdeIP, I-TevI, I-TevII, I-TevIII, I-UarAP, I-UarHGPA1P, I-UarHGPA13P, I-VinIP, I-ZbiIP, PI-MtuI, PI-MtuHIP, PI-MtuHIP, PI-PfuI, PI-PfuII, PI-PkoI, PI-PkoII, PI-PspI, PI-Rma43812IP, PI-SPBetaIP, PI-SceI, PI-TfuI, PI-TfuII, PI-ThyI, PI-TliI, PI-TliII, and combinations thereof.

Preferred in this context are the homing endonucleases whose gene sequences are already known, such as, for example, F-SceI,I-CeuI,I-ChuI, I-DmoI, I-CpaI, I-CpaII, I-CreI, I-CsmI, F-TevI, F-TevII, I-TevI, I-TevII, I-AniI, I-CvuI, I-DdiI, I-HmuI, I-HmuII, I-LlaI, I-NanI, I-MsoI, I-NitI, I-NjaI, I-PakI, I-PorI, I-PpoI, I-ScaI, I-Ssp68031, PI-PkoI, PI-PkoII, PI-PspI, PI-TfuI, PI-TliI, and combinations thereof.

Very especially preferred are commercially available homing endonucleases such as I-CeuI, I-SceI, I-DmoI, I-PpoI, PI-PspI or PI-SceI.

The enzymes can be isolated from their organisms of origin in the manner with which the skilled worker is familiar, and/or their coding nucleic acid sequence can be cloned. The sequences of various enzymes are deposited in GenBank.

Very especially preferred are the homing endonucleases I-SceI, I-CpaI, I-CpaII, I-CreI and I-ChuI. Most preferred are the homing endonucleases as shown in SEQ ID NO: 2, 4, 6, 8 or 10, or combinations thereof.

Synthetic DSBI enzymes which may be mentioned by way of example are chimeric nucleases which are composed of an unspecific nuclease domain and a sequence-specific DNA binding domain consisting of zinc fingers (Bibikova M et al. (2001) Mol Cell Biol. 21:289-297). These DNA-binding zinc finger domains can be adapted to suit any DNA sequence. Suitable methods for preparing suitable zinc finger domains are described and known to the skilled worker (Beerli R R et al., Proc Natl Acad Sci USA. 2000; 97 (4):1495-1500; Beerli R R, et al., J Biol Chem 2000; 275(42):32617-32627; Segal D J and Barbs C F 3rd., Curr Open Chem Biol 2000; 4(1):34-39; Kang J S and Kim J S, J Biol Chem 2000; 275(12):8742-8748; Beerli R R et al., Proc Natl Acad Sci USA 1998; 95(25):14628-14633; Kim J S et al., Proc Natl Acad Sci USA 1997; 94(8):3616-3620; Klug A, J Mol Biol 1999; 293(2): 215-218; Tsai S Y et al., Adv Drug Deliv Rev 1998; 30(1-3): 23-31; Mapp A K et al., Proc Natl Acad Sci USA 2000; 97(8):3930-3935; Sharrocks A D et al., Int J Biochem Cell Biol 1997; 29(12):1371-1387; Zhang L et al., J Biol Chem 2000; 275(43):33850-33860).

The DSBI enzyme is preferably expressed as a fusion protein with a nuclear localization sequence (NLS). This NLS sequence enables facilitated transport into the nucleus and increases the efficacy of the recombination system. A variety of NLS sequences are known to the skilled worker and described, inter alia, by Jicks G R and Raikhel N V (1995) Annu. Rev. Cell Biol. 11:155-188. Preferred for plant organisms is, for example, the NLS sequence of the SV40 large antigen. Very especially preferred are the following NLS sequences:

```
NLS1:
N-Pro-Lys-Thr-Lys-Arg-Lys-Val-C    (SEQ ID NO: 29)

NLS2:
N-Pro-Lys-Lys-Lys-Arg-Lys-Val-C    (SEQ ID NO: 30)
```

The homing endonucleases as shown in SEQ ID NO: 4, 6, 8 or 10 used in the use examples are fusion proteins of the native nucleases and the NLS2 nuclear localization sequence.

Owing to the small size of many DSBI enzymes (such as, for example, the homing endonucleases), an NLS sequence is not necessarily required. These enzymes are capable of passing through the nuclear pores even without any aid. This is confirmed by the efficacy of the homing endonuclease as shown in SEQ ID NO: 2 which has been used and which encompasses no nuclear localization sequence.

In a further preferred embodiment, the activity of the DSBI enzyme can be induced. Suitable methods have been described for sequence-specific recombinases (Angrand P O et al. (1998) Nucl. Acids Res. 26(13):3263-3269; Logie C and Stewart A F (1995) Proc Natl Acad Sci USA 92(13):5940-5944; Imai T et al. (2001) Proc Natl Acad Sci USA 98(1): 224-228). These methods employ fusion proteins of the DSBI enzyme and the ligand binding domain for steroid hormone receptor (for example the human androgen receptor, or mutated variants of the human estrogen receptor as described therein). Induction may be effected with ligands such as, for example, estradiol, dexamethasone, 4-hydroxytamoxifen or raloxifen.

Some DBSI enyzmes are active as dimers (homo- or heterodimers; I-CreI forms a homodimer; I-SecIV forms a heterodimer) (Wernette C M (1998) Biochemical & Biophysical Research Communications 248(1):127-333)). Dimerization can be designed as an inducible feature, for example by exchanging the natural dimerization domains for the binding domaine of a low-molecular-weight ligand. Addition of a dimeric ligand then brings about dimerization of the fusion protein. Corresponding inducible dimerization methods, and the preparation of the dimeric ligands, have been described (Amara J F et al. (1997) Proc Natl Acad Sci USA 94(20): 10618-1623; Muthuswamy S K et al. (1999) Mol Cell Biol 19(10):6845-685; Schultz L W and Clardy J (1998) Bioorg Med Chem Lett. 8(1):1-6; Keenan T et al. (1998) Bioorg Med Chem. 6(8):1309-1335).

"Recognition sequence for the site-directed induction of DNA double-strand breaks" generally refers to those sequences which, under the conditions in the eukaryotic cell or organism used in each case, enable the recognition and cleavage by the DSBI enzyme. The recognition sequences for the respective DSBI enzymes detailed are mentioned in Table 1 herein by way of example, but not by limitation.

TABLE 1

Recognition sequences and organisms of origin of DSBI enyzmes ("^" indicates the cleavage site of the DSBI enzyme within a recognition sequence).

| DSBI enzyme | Organism of origin | Recognition sequence |
|---|---|---|
| CRE | Bacteriophage P1 | 5'-AACTCTCATCGCTTCGGATAACTTCCTGTTATCCGAAACATATCACTCACTTTGGTGATTTCACCGTAACTGTCTATGATTAATG-3' |
| FLP | Saccharomyces cerevisiae | 5'-GAAGTTCCTATTCCGAAGTTCCTATTCTCTAGAAAGTATAGGAACTTC-3' |
| R | pSR1 Plasmids | 5'-CGAGATCATATCACTGTGGACGTTGATGAAAGAATACGTTATTCTTTCATCAAATCGT |
| P-Element Transposase | Drosophila | 5'-CTAGATGAAATAACATAAGGTGG |
| I-AniI | Aspergillus nidulans | 5'-TTGAGGAGGTT^TCTCTGTAAATAANNNNNNNNNNNNNNN 3'-AACTCCTCCAAAGAGACATTTATTNNNNNNNNNNNNNNN^ |
| I-DdiI | Dictyostelium discoideumAX3 | 5'-TTTTTTGGTCATCCAGAAGTATAT 3'-AAAAAACCAG^TAGGTCTTCATATA |

TABLE 1-continued

Recognition sequences and organisms of origin of DSBI enyzmes ("^" indicates the cleavage site of the DSBI enzyme within a recognition sequence).

| DSBI enzyme | Organism of origin | Recognition sequence |
| --- | --- | --- |
| I-CvuI | Chlorella vulgaris | 5'-CTGGGTTCAAAACGTCGTGA^GACAGTTTGG<br>3'-GACCCAAGTTTTGCAG^CACTCTGTCAAACC |
| I-CsmI | Chlamydomonas smithii | 5'-GTACTAGCATGGGGTCAAATGTCTTTCTGG |
| I-CmoeI | Chlamydomonas moewusii | 5'-TCGTAGCAGCT^CACGGTT<br>3'-AGCATCG^TCGAGTGCCAA |
| I-CreI | Chlamydomonas reinhardtii | 5'-CTGGGTTCAAAACGTCGTGA^GACAGTTTGG<br>3'-GACCCAAGTTTTGCAG^CACTCTGTCAAACC |
| I-ChuI | Chlamydomonas humicola | 5'-GAAGGTTTGGCACCTCG^ATGTCGGCTCATC<br>3'-CTTCCAAACCGTG^GAGCTACAGCCGAGTAG |
| I-CpaI | Chlamydomonas pallidostigmatica | 5'-CGATCCTAAGGTAGCGAA^ATTCA<br>3'-GCTAGGATTCCATC^GCTTTAAGT |
| I-CpaII | Chlamydomonas pallidostigmatica | 5'-CCCGGCTAACTC^TGTGCCAG<br>3'-GGGCCGAT^TGAGACACGGTC |
| I-CeuI | Chlamydomonas eugametos | 5'-CGTAACTATAACGGTCCTAA^GGTAGCGAA<br>3'-GCATTGATATTGCCAG^GATTCCATCGCTT |
| I-DmoI | Desulfurococcus mobilis | 5'-ATGCCTTGCCGGGTAA^GTTCCGGCGCGCAT<br>3'-TACGGAACGGCC^CATTCAAGGCCGCGCGTA |
| I-SceI | S. cerevisiae | 5'-AGTTACGCTAGGGATAA^CAGGGTAATATAG<br>3'-TCAATGCGATCCC^TATTGTCCCATTATATC<br>5'-TAGGGATAA^CAGGGTAAT<br>3'-ATCCC^TATTGTCCCATTA ("Core"-Sequence) |
| I-SceII | S. cerevisiae | 5'-TTTTGATTCTTTGGTCACCC^TGAAGTATA<br>3'-AAAACTAAGAAACCAG^TGGGACTTCATAT |
| I-SceIII | S. cerevisiae | 5'-ATTGGAGGTTTTGGTAAC^TATTTATTACC<br>3'-TAACCTCCAAAACC^ATTGATAAATAATGG |
| I-SceIV | S. cerevisiae | 5'-TCTTTTCTCTTGATTA^GCCCTAATCTACG<br>3'-AGAAAAGAGAAC^TAATCGGGATTAGATGC |
| I-SceV | S. cerevisiae | 5'-AATAATTTTCT^TCTTAGTAATGCC<br>3'-TTATTAAAAGAAGAATCATTA^CGG |
| I-SceVI | S. cerevisiae | 5'-GTTATTTAATG^TTTTAGTAGTTGG<br>3'-CAATAAATTACAAAATCATCA^ACC |
| I-SceVII | S. cerevisiae | 5'-TGTCACATTGAGGTGCACTAGTTATTAC |
| PI-SceI | S. cerevisiae | 5'-ATCTATGTCGGGTGC^GGAGAAAGAGGTAAT<br>3'-TAGATACAGCC^CACGCCTCTTTCTCCATTA |
| F-SceI | S. cerevisiae | 5'-GATGCTGTAGGC^ATAGGCTTGGTT<br>3'-CTACGACA^TCCGTATCCGAACCAA |
| F-SceII | S. cerevisiae | 5'-CTTTCCGCAACA^GTAAAATT<br>3'-GAAAGGCG^TTGTCATTTTAA |
| I-HmuI | Bacillus subtilis bacteriophage SPO1 | 5'-AGTAATGAGCCTAACGCTCAGCAA<br>3'-TCATTACTCGGATTGC^GAGTCGTT |
| I-HmuII | Bacillus subtilis bacteriophage SP82 | 5'-AGTAATGAGCCTAACGCTCAACAANNNNNNNNNNNNNNNNNNNNNN<br>NNNNNNNNNNNNNNNNNN |

TABLE 1-continued

Recognition sequences and organisms of origin of DSBI enyzmes ("^" indicates the cleavage site of the DSBI enzyme within a recognition sequence).

| DSBI enzyme | Organism of origin | Recognition sequence |
|---|---|---|
| I-LlaI | *Lactococcus lactis* | 5'-CACATCCATAAC^CATATCATTTTT<br>3'-GTGTAGGTATTGGTATAGTAA^AAA |
| I-MsoI | *Monomastix* species | 5'-CTGGGTTCAAAACGTCGTGA^GACAGTTTGG<br>3'-GACCCAAGTTTTGCAG^CACTCTGTCAAACC |
| I-NanI | *Naegleria andersoni* | 5'-AAGTCTGGTGCCA^GCACCCGC<br>3'-TTCAGACC^ACGGTCGTGGGCG |
| I-NitI | *Naegleria italica* | 5'-AAGTCTGGTGCCA^GCACCCGC<br>3'-TTCAGACC^ACGGTCGTGGGCG |
| I-NjaI | *Naegleria jamiesoni* | 5'-AAGTCTGGTGCCA^GCACCCGC<br>3'-TTCAGACC^ACGGTCGTGGGCG |
| I-PakI | *Pseudendoclonium akinetum* | 5'-CTGGGTTCAAAACGTCGTGA^GACAGTTTGG<br>3'-GACCCAAGTTTTGCAG^CACTCTGTCAAACC |
| I-PorI | *Pyrobaculum organotrophum* | 5'-GCGAGCCCGTAAGGGT^GTGTACGGG<br>3'-CGCTCGGGCATT^CCCACACATGCCC |
| I-PpoI | *Physarum polycephalum* | 5'-TAACTATGACTCTCTTAA^GGTAGCCAAAT<br>3'-ATTGATACTGAGAG^AATTCCATCGGTTTA |
| I-ScaI | *Saccharomyces capensis* | 5'-TGTCACATTGAGGTGCACT^AGTTATTAC<br>3'-ACAGTGTAACTCCAC^GTGATCAATAATG |
| I-Ssp6803I | *Synechocystis* species | 5'-GTCGGGCT^CATAACCCGAA<br>3'-CAGCCCGAGTA^TTGGGCTT |
| PI-PfuI | *Pyrococcus furiosus* Vc1 | 5'-GAAGATGGGAGGAGGG^ACCGGACTCAACTT<br>3'-CTTCTACCCTCC^TCCCTGGCCTGAGTTGAA |
| PI-PfuII | *Pyrococcus furiosus* Vc1 | 5'-ACGAATCCATGTGGAGA^AGAGCCTCTATA<br>3'-TGCTTAGGTACAC^CTCTTCTGGGAGATAT |
| PI-PkoI | *Pyrococcus kodakaraensis* KOD1 | 5'-GATTTTAGAT^CCCTGTACC<br>3'-CTAAAA^TCTAGGGACATGG |
| PI-PkoII | *Pyrococcus kodakaraensis* KOD1 | 5'-CAGTACTACG^GTTAC<br>3'-GTCATG^ATGCCAATG |
| PI-PspI | *Pyrococcus* sp. | 5'-AAAATCCTGGCAAACAGCTATTAT^GGGTAT<br>3'-TTTTAGGACCGTTTGTCGAT^AATACCCATA |
| PI-TfuI | *Thermococcus fumicolans* ST557 | 5'-TAGATTTTAGGT^CGCTATATCCTTCC<br>3'-ATCTAAAA^TCCAGCGATATAGGAAGG |
| PI-TfuII | *Thermococcus fumicolans* ST557 | 5'-TAYGCNGAYACN^GACGGYTTYT<br>3'-ATRCGNCT^RTGNCTGCCRAARA |
| PI-ThyI | *Thermacoccus hydrothermalis* | 5'-TAYGCNGAYACN^GACGGYTTYT<br>3'-ATRCGNCT^RTGNCTGCCRAARA |
| PI-TliI | *Thermococcus litoralis* | 5'-TAYGCNGAYACNGACGG^YTTYT<br>3'-ATRCGNCTRTGNC^TGCCRAARA |
| PI-TliII | *Thermococcus litoralis* | 5'-AAATTGCTTGCAAACAGCTATTACGGCTAT |
| I-TevI | Bacteriophage T4 | 5'-AGTGGTATCAAC^GCTCAGTAGATG<br>3'-TCACCATAGT^TGCGAGTCATCTAC |
| I-TevII | Bacteriophage T4 | 5'-GCTTATGAGTATGAAGTGAACACGT^TATTC<br>3'-CGAATACTCATACTTCACTTGTG^CAATAAG |

TABLE 1-continued

Recognition sequences and organisms of origin of DSBI enyzmes ("^" indicates the cleavage site of the DSBI enzyme within a recognition sequence).

| DSBI enzyme | Organism of origin | Recognition sequence |
|---|---|---|
| F-TevI | Bacteriophage T4 | 5'-GAAACACAAGA^AATGTTTAGTAAANNNNNNNNNNNNNNN<br>3'-CTTTGTGTTCTTTACAAATCATTTNNNNNNNNNNNNNNN^ |
| F-TevII | Bacteriophage T4 | 5'-TTTAATCCTCGCTTC^AGATATGGCAACTG<br>3'-AAATTAGGAGCGA^AGTCTATACCGTTGAC |

Also encompassed are minor deviations (degenerations) of the recognition sequence which still enable recognition and cleavage by the DSBI enzyme in question. Such deviations—also in connection with different framework conditions such as, for example, calcium or magnesium concentration—have been described (Argast G M et al. (1998) J Mol Biol 280: 345-353). Also encompassed are core sequences of these recognition sequences. It is known that the inner portions of the recognition sequences suffice for an induced double-strand break and that the outer ones are not absolutely relevant, but can codetermine the cleavage efficacy. Thus, for example, an 18bp core sequence can be defined for I-SceI.

Recombination construct and DSBI enzyme can be combined to give one of the recombination systems or methods according to the invention in various ways with which the skilled worker is familiar. Thus, the recombination constructs and the DSBI enzyme can be combined in an organism, a cell, a cell compartment or a tissue for example as follows:

1.) Organisms which have the recombination cassette inserted into the chromosomal DNA are generated in the customary manner. For example, such plants can be generated preferably by agrobacteria-mediated transformation. The primary transformants which contain the recombination cassette are employed for the transformation with an expression cassette which ensures expression of the DSBI enzyme or grown in a suitable manner until homozygous, when they act as the host organism (for example host plant) for the transformation with an expression cassette which ensures expression of the DSBI enzyme. Starting from these host plants, it is possible, for example, to initiate, establish and use for transformation purposes in-vitro cultures such as, for example, callus cultures or embryogenic cultures. Transformation with the expression cassette for the DSBI enzyme can be in each case stable or transient.

2.) Organisms known as master organisms, which bear and express the corresponding gene for the DSBI enzyme (or an expression cassette which ensures the expression of the DSBI enzyme) are generated in the customary manner. For example, such master plants can be generated preferably by *agrobacterium*-mediated transformation. The primary transformants which express the DSBI enzyme are employed for the transformation with the recombination construct or grown in a suitable manner until homozygous, which is when they act as master organism or host organism (for example master plant) into which the recombination constructs are introduced. Starting from these master plants, it is possible, for example, to initiate, establish and use for transformation purposes in-vitro cultures such as, for example, callus cultures or embryogenic cultures.

3.) The gene encoding the DSBI enzyme (or an expression cassette which ensures the expression of the DSBI enzyme) can be integrated into a vector which already bears the recombination cassette and thus introduced into plant cells simultaneously with the target gene. It is preferred to insert the gene encoding the DSBI enzyme between the homology sequences and thus to delete it from the chromosomal DNA after it has fulfilled its function. Very especially preferably, expression of the DSBI enzyme is inducible in such a case (for example under the control of one of the inducible promotors described herein), in a development-dependent fashion using a development-dependent promotor, or else DSBI enzymes are employed whose activity is inducible in order to avoid cleaving the recombination construct immediately after the transformation and prior to its insertion into the genome.

4.) Relying on the co-transformation technique, the expression cassette which ensures the expression of the DSBI enzyme can be transformed into the cells simultaneously with the recombination construct, but on a separate vector. Co-transformation can be in each case stable or transient. In such a case, expression of the DSBI enzyme is preferably inducible (for example under the control of one of the inducible promotors described herein), in a development-dependent fashion using a development-dependent promotor, or else DSBI enzymes are employed whose activity is inducible in order to avoid cleaving the recombination construct immediately after the transformation and prior to its insertion into the genome.

5.) Organisms, for example plants or else animals, expressing the DSBI enzyme may also act as parent individuals. In the progeny from the hybridization between organisms expressing the DSBI enzyme on the one hand and organisms bearing the recombination construct on the other hand, the desired double-strand breaks and recombination between the homology sequences are observed, with the possible deletion of the sequences located between the homology sequences.

6.) Expression of the DSBI enzyme is also conceivable in a transient transformation approach in which the possibilities 2 to 4 can be exploited.

7.) The DSBI enzyme can also be introduced into cells comprising or bearing the transgenic recombination construct directly, for example via microinjection, particle bombardment (biolistic method), polyethylene glycol transfection or liposome-mediated transfection. This embodiment is advantageous since no DSBI-enzyme-encoding sequences can remain in the genome. Such a method has been described for example by Segal D J et al. (1995) Proc Natl Acad Sci USA 92:806-810.

8.) The DSBI enzyme may also be generated by introducing the DSBI-enzyme-encoding, in-vitro-generated mRNA into cells (for example via microinjection, particle bombardment (biolistic method) or liposome-mediated transfection). This embodiment is advantageous since no DSBI-enzyme-encoding sequences can remain in the genome.

9.) The DSBI enzyme can be introduced into plant cells as a fusion protein with the VirE2 or VirF protein of an *agrobacterium*. Such methods have been described for example for Cre recombinase (Vergunst A C et al. (2000) Science. 290: 979-982). If the expression cassette for the fusion protein is located outside the border sequences, it is not inserted into the plant genome. This embodiment is advantageous since no DSBI-enzyme-encoding sequences can remain in the genome.

The recombination system or method according to the invention can be realized in intact organisms or else in parts, cells or propagation material derived therefrom, especially preferably in intact plants or else in any plant tissue or plant in-vitro cultures including callus. An in-vitro application using, for example, wheat germ extract or reticulocyte extract can also be envisaged.

As described above, the DSBI enzyme can be generated using an expression cassette which comprises the DNA encoding a DSBI enzyme and is introduced into a eukaryotic cell or organism. In this context, the expression cassette for the DSBI enzyme preferably comprises a nucleic acid sequence encoding a DSBI enzyme as shown in SEQ ID NO: 2, 4, 6, 8 or 10 or a functional equivalent of same which is capable of generating DNA double-strand breaks in double-stranded DNA using the essentially identical recognition sequence. Essentially identical recognition sequences refer to those recognition sequences which, while deviating from the recognition sequence identified as optimal for the enzyme in question, still permit cleavage by this enzyme. Very especially preferably, the expression cassettes for the DSBI enzyme comprise a nucleic acid sequence as shown in SEQ ID NO: 1, 3, 5, 7 or 9, or combinations thereof.

Expression cassette—for example when referring to the expression cassette for the DSBI enzyme—means those constructions in which the DNA to be expressed is linked operably to at least one genetic control element which enables or regulates its expression (i.e. transcription and/or translation). Here, expression may be for example stable or transient, constitutive or inducible. For introducing it, the skilled worker may resort to various direct methods (for example transfection, particle bombardment, microinjection) or indirect methods (for example infection with agrobacteria, infection with viruses), all of which are detailed further below.

Operable linkage is generally understood as meaning an arrangement in which a genetic control sequence is capable of exerting its function with regard to a nucleic acid sequence, for example while encoding a DSBI enzyme. Function, in this context, may mean for example control of the expression, i.e. transcription and/or translation, of the nucleic acid sequence, for example one encoding a DSBI enzyme. Control, in this context, encompasses for example initiating, increasing, governing or suppressing the expression, i.e. transcription and, if appropriate, translation. Controlling, in turn, may be, for example, tissue- and/or time-specific. It may also be inducible, for example by certain chemicals, stress, pathogens and the like.

Operable linkage is understood as meaning for example the sequential arrangement of a promotor, of the nucleic acid sequence to be expressed—for example one encoding a DSBI enzyme—and, if appropriate, further regulatory elements such as, for example, a terminator, in such a way that each of the regulatory elements can fulfill its function when the nucleic acid sequence—for example one encoding a DSBI enzyme—is expressed.

This does not necessarily require a direct linkage in the chemical sense. Genetic control sequences such as, for example, enhancer sequences are also capable of exerting their function on the target sequence from positions located at a distance or indeed other DNA molecules. Preferred arrangements are those in which the nucleic acid sequence to be expressed—for example one encoding a DSBI enzyme—is positioned after a sequence acting as promotor so that the two sequences are linked covalently to one another. The distance between the promotor sequence and the nucleic acid sequence—for example one encoding a DSBI enzyme—is preferably less than 200 base pairs, especially preferably less than 100 base pairs, very especially preferably less than 50 base pairs.

The skilled worker is familiar with a variety of ways in order to obtain such an expression cassette. For example, it is preferably prepared by directly fusing a nucleic acid sequence which acts as promotor with a nucleotide sequence to be expressed—for example one encoding a DSBI enzyme. Operable linkage can be achieved by means of customary recombination and cloning techniques as are described, for example, in T. Maniatis, E. F. Fritsch and J. Sambrook, Molecular Cloning: A Laboratory Manual, Cold Spring Harbor Laboratory, Cold Spring Harbor, N.Y. (1989), in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

However, an expression cassette may also be constructed in such a way that the nucleic acid sequence to be expressed (for example one encoding a DSBI enzyme) is brought under the control of an endogenous genetic control element, for example a promotor, for example by means of homologous recombination or else by random insertion. Such constructs are likewise understood as being expression cassettes for the purposes of the invention.

The skilled worker furthermore knows that nucleic acid molecules may also be expressed using artificial transcription factors of the zinc finger protein type (Beerli R R et al. (2000) Proc Natl Acad Sci USA 97(4):1495-500). These factors can be adapted to suit any sequence region and enable expression independently of certain promotor sequences.

The term "genetic control sequences" is to be understood in the broad sense and refers to all those sequences which affect the coming into existence, or the function, of the expression cassette according to the invention. For example, genetic control sequences ensure transcription and, if appropriate, translation in prokaryotic or eukaryotic organisms. Preferably, the expression cassettes according to the invention encompass 5'-upstream of the respective nucleic acid sequence to be expressed a promotor and 3'-downstream a terminator sequence as additional genetic control sequence, and, if appropriate, further customary regulatory elements, in each case in operable linkage with the nucleic acid sequence to be expressed.

Genetic control sequences are described, for example, in "Goeddel; Gene Expression Technology: Methods in Enzymology 185, Academic Press, San Diego, Calif. (1990)" or "Gruber and Crosby, in: Methods in Plant Molecular Biology and Biotechnology, CRC Press, Boca Raton, Fla., eds.: Glick and Thompson, Chapter 7, 89-108" and the references cited therein.

Examples of such control sequences are sequences to which inductors or repressors bind and thus regulate the expression of the nucleic acid. The natural regulation of the sequences before the actual structural genes may still be present in addition to these novel control sequences or instead of these sequences and, if appropriate, may have been genetically modified in such a way that the natural regulation has been switched off and gene expression increased. However, the expression cassette may also be simpler in construction, that is to say no additional regulatory signals are inserted before the abovementioned genes, and the natural promotor together with its regulation is not removed. Instead, the natural control sequence is mutated in such a way that regulation no longer takes place and gene expression is increased. These modified promotors may also be placed on their own before the natural genes for increasing the activity.

A variety of control sequences are suitable, depending on the host organism or starting organism described in greater detail herein, which, owing to the introduction of the expression cassettes or vectors, becomes a genetically modified, or transgenic, organism.

Advantageous control sequences for the expression cassettes or vectors according to the invention are present for example in promotors such as cos, tac, trp, tet, phoA, tat, lpp, lac, lacIq, T7, T5, T3, gal, trc, ara, SP6, ?-PR or in the ?-PL promotor, which are advantageously used in Gram-negative bacteria.

Further advantageous control sequences are present for example in the Gram-positive promotors amy and SPO2, in the yeast or fungal promotors ADC1, MFa, AC, P-60, CYC1, GAPDH, TEF, rp28, ADH or in the plant promotors CaMV/35S (Franck et al. (1980) Cell 21:285-294), PRP1 (Martini N et al. (1993) Mol Gen Genet. 236(2-3):179-186), SSU, OCS, LEB4, USP, STLS1, B33, NOS; FBPaseP (WO 98/18940) or in the ubiquitin or phaseolin promotors.

Vectors which are suitable for expression in vertebrates, preferably in mammals, are vectors like the TK promotor, the RSV 3' LTR promotor, the CMV promotor or the SV40 early or late promotor. The skilled worker is familiar with other promotors. Inducible promotors suitable for use in vertebrates, preferably in mammals, encompass for example the Tet promotor/repressor, which is inducible or repressible by tetracycline or derivatives, the dexamethasone-inducible MMTV-LTR promotor, the *Drosophila* minimal heat shock promotor, which is inducible by ecdysone or the analog ponasterone A (for example within the pVgRXR expression system; Invitrogen, Inc.).

A preferred promotor is, in principle, any promotor which is capable of controlling the expression of genes, in particular foreign genes, in plants. Preferred promotors are those which enable constitutive expression in plants (Benfey et al. (1989) EMBO J. 8:2195-2202). A promotor which is preferably used is, in particular, a plant promotor or a promotor derived from a plant virus. Especially preferred is the promotor of the cauliflower mosaic virus 35S transcript (Franck et al. (1980) Cell 21:285-294; Odell et al. (1985) Nature 313:810-812; Shewmaker et al. (1985) Virology 140:281-288; Gardner et al. 1986, Plant Mol. Biol. 6, 221-228) or the 19S CaMV promotor (U.S. Pat. No. 5,352,605 and WO 84/02913). It is known that this promotor comprises a variety of recognition sequences for transcriptional effectors which, in their totality, bring about permanent and constitutive expression of the gene introduced (Benfey et al. (1989) EMBO J 8:2195-2202). A further suitable constitutive promotor is the Rubisco small subunit (SSU) promotor (U.S. Pat. No. 4,962,028). A further example of a suitable promotor is the leguminB promotor (GenBank Acc.-No.: X03677). Further preferred constitutive promotors are, for example, the *Agrobacterium* nopaline synthase promotor, the TR dual promotor, the *agrobacterium* OCS (octopine synthase) promotor, the ubiquitin promotor (Holtorf S et al. (1995) Plant Mol Biol 29:637-649), the promoters of the vacuolar ATPase subunits, or the promotor of a wheat proline-rich protein (WO 91/13991).

The Expression cassettes may also comprise an inducible, preferably chemically inducible, promotor (Aoyama T and Chua N H (1997) Plant J 11:605-612; Caddick M X et al. (1998) Nat. Biotechnol 16:177-180; Review: Gatz, Annu Rev Plant Physiol Plant Mol Biol 1997, 48:89-108), by means of which the expression of the exogenous gene in the plant can be controlled at a specific point in time. Such promotors, such as, for example, the PRP1 promotor (Ward et al., Plant. Mol. Biol. 22 (1993), 361-366), a salicylic-acid-inducible promotor (WO 95/19443), a benzenesulfonamide-inducible promotor (EP-A-0388186), a tetracycline-inducible promotor (Gatz et al., (1992) Plant J. 2, 397-404), an abscisic acid-inducible promotor (EP-A 335528), a salicylic acid-inducible promotor (WO 95/19443) or an ethanol-(Salter M G et al. (1998) *Plant J.* 16:127-132) or cyclohexanone-inducible (WO 93/21334) promotor may likewise be used.

In an especially preferred embodiment, the DSBI-enzyme-encoding nucleic acid, in particular, is expressed under the control of an inducible promotor. This leads to a controlled, governable expression and deletion—for example in plants—, and any problems caused by a constitutive expression of a DSBI enzyme are avoided.

Other preferred promotors are promoters induced by biotic or abiotic stress, such as, for example, the pathogen-inducible promotor of the PRP1 gene (Ward et al., Plant Mol Biol 1993, 22: 361-366), the tomato heat-inducible hsp80 promotor (U.S. Pat. No. 5,187,267), the potato chill-inducible alpha-amylase promotor (WO 96/12814) or the wound-induced pinII promotor (EP375091).

Other preferred promoters are promoters with specificity for the anthers, ovaries, pollen, the meristem, flowers, leaves, stems, roots and seeds.

A development-regulated promotor is, inter alia, described by Baerson et al. (Baerson S R, Lamppa G K (1993) Plant Mol Biol 22(2):255-67).

Especially preferred promoters are those which ensure expression in tissues or plant parts in which the biosynthesis of starch and/or oils or their precursors takes place or in which the products are advantageously accumulated. The biosynthesis site of starch are the chloroplasts of the leaves or the amyloplasts of the storage organs such as seeds, fruits or tubers. Within these organs, it is predominantly the cells of the endosperm or the cotyledons of the embryo in which synthesis takes place. Preferred promotors are thus in addition to the abovementioned constitutive promotors in particular seed-specific promotors such as, for example, the phaseolin promotor (U.S. Pat. No. 5,504,200, Bustos M M et al., Plant Cell. 1989; 1(9):839-53), the promotor of the 2S albumin gene (Joseffson L G et al. (1987) J Biol Chem 262: 12196-12201), the legumin promotor (Shirsat A et al. (1989) Mol Gen Genet. 215(2):326-331), the USP (unknown seed protein) promotor (Bäumlein H et al. (1 991) Molecular & General Genetics 225(3):459-67), the napin gene promotor (U.S. Pat. No. 5,608,152; Stalberg K, et al. (1996) L. Planta 199: 515-519), the sucrose binding protein promotor (WO 00/26388) or the legumin B4 promotor (LeB4; Bäumlein H et al. (1991) Mol Gen Genet 225:121-128; Baeumlein et al. (1992) Plant Journal 2(2):233-239; Fiedler U et al. (1995) Biotechnology (NY) 13(10):1090-1093), the Ins *Arabidopsis* oleosin promotor (WO9845461), the *Brassica* Bce4 promotor (WO 91/13980). Further suitable seed-specific promoters are those of the genes encoding the "high-molecular-weight glutenin" (HMWG), gliadin, branching enzyme, ADP-glucose pyrophosphatase (AGPase) or starch synthase. Furthermore preferred promoters are those which enable seed-specific expression in monocots such as maize, barley, wheat, rye, rice and the like. Promotors which may advantageously be employed are the promotor of the lpt2 or lpt1 gene (WO 95/15389, WO 95/23230) or the promotors described in WO 99/16890 (promoters of the hordein gene, the glutelin gene, the oryzin gene, the prolamine gene, the gliadin gene, the glutelin gene, the zein gene, the kasirin gene or the secalin gene).

Promotors which are preferred as genetic control elements are, furthermore, pollen-specific promoters such as, for example, the promotor of the B. campestris bgp1 gene (GenBank Acc.-No: X68210; Xu H et al. (1993) Mol Gen Genet 239(1-2):58-65; WO 94/13809), of the Oryza sativa ory s1 gene (GenBank Acc.-No.: AJ012760; Xu H et al. (1995) Gene 164 (2):255-259), of the pollen-specific maize gene ZM13 (Hamilton D A et al. (1998) Plant Mol Biol 38(4):663-669; U.S. Pat. No. 5,086,169), of the B.napus gene Bp10 (GenBank Acc.-No.: X64257; Albani D (1992) Plant J 2(3):331-342; U.S. Pat. No. 6,013,859), and functional combinations of such promoters.

Other preferred promoters are the Lcg1 promotor for cell-specific expression in the male gametes (WO 99/05281; XU H et al. (1999) Proc. Natl. Acad. Sci. USA Vol. 96:2554-2558) and the promotor of the AtDMC1 gene (Klimyuk V I et al.(1997) Plant J. 11(1):1-14).

Further suitable promoters are, for example, specific promotors for tubers, storage roots or roots such as, for example, the class I patatin promoter (B33), the potato cathepsin D inhibitor promoter, the starch synthase (GBSS1) promoter or the sporamin promoter, and fruit-specific promoters such as, for example, the tomato fruit-specific promotor (EP-A 409625).

Promotors which are furthermore suitable are those which ensure leaf-specific expression. Promotors which may be mentioned are the potato cytosolic FBPase promoter (WO 98/18940), the Rubisco (ribulose-1,5-bisphosphate carboxylase) SSU (small subunit) promoter, the potato ST-LSI promotor (Stockhaus et al. (1989) EMBO J 8(9):2445-2451) or functional combinations of such promoters. Other preferred promotors are those which govern expression in seeds and plant embryos.

Further suitable promoters are, for example, fruit-maturation-specific promoters such as, for example, the tomato fruit-maturation-specific promoter (WO 94/21794), flower-specific promoters such as, for example, the phytoene synthase promotor (WO 92/16635) or the promotor of the P-rr gene (WO 98/22593) or another node-specific promotor as described in EP-A 249676 may be used advantageously.

In principle, all natural promoters together with their regulatory sequences, such as those mentioned above, may be used for the method according to the invention. In addition, synthetic promoters may also be used advantageously.

Genetic control sequences also encompass further promoters, promotor elements or minimal promotors capable of modifying the expression-specific characteristics. Thus, for example, the tissue-specific expression may take place in addition as a function of certain stress factors, owing to genetic control sequences. Such elements are, for example, described for water stress, abscisic acid (Lam E and Chua N H (1991) J Biol Chem 266(26):17131-17135) and heat stress (Schoffl F et al. (1989) Molecular & General Genetics 217 (2-3):246-53).

Furthermore, other promotors which enable expression in further plant tissues or other organisms, such as, for example, E.coli bacteria, may be linked operably with the nucleic acid sequence to be expressed. Plant promotors which are suitable are, in principle, all of the above-described promotors.

Genetic control sequences furthermore also encompass the 5'-untranslated region, introns or the noncoding 3'-region of genes. It has been demonstrated that they may play a significant role in the regulation of gene expression. Thus, it has been demonstrated that 5'-untranslated sequences are capable of enhancing the transient expression of heterologous genes. Furthermore, they may promote tissue specificity (Rouster J et al., Plant J. 1998, 15: 435-440.). Conversely, the 5'-untranslated region of the opaque-2 gene suppresses expression. Deletion of the region in question leads to an increased gene activity (Lohmer S et al., Plant Cell 1993, 5:65-73).

Genetic control sequences may also encompass ribosome binding sequences for initiating translation. This is preferred in particular when the nucleic acid sequence to be expressed does not provide suitable sequences or when they are not compatible with the expression system.

The expression cassette can advantageously comprise one or more of what are known as enhancer sequences in operable linkage with the promotor, which enable the increased transgenic expression of the nucleic acid sequence. Additional advantageous sequences, such as further regulatory elements or terminators, may also be inserted at the 3' end of the nucleic acid sequences to be expressed recombinantly. One or more copies of the nucleic acid sequences to be expressed recombinantly may be present in the gene construct.

Genetic control sequences are furthermore understood as meaning sequences which encode fusion proteins consisting of a signal peptide sequence.

Polyadenylation signals which are suitable as genetic control sequences are plant polyadenylation signals, preferably those which correspond essentially to T-DNA polyadenylation signals from *Agrobacterium tumefaciens*, in particular of gene 3 of the T-DNA (octopine synthase) of the Ti plasmids pTiACH5 (Gielen et al., EMBO J. 3 (1984), 835 et sec.) or functional equivalents thereof. Examples of particularly suitable terminator sequences are the OCS (octopine synthase) terminator and the NOS (nopaline synthase) terminator.

As mentioned above, the recombination constructs according to the invention may encompass further nucleic acid sequences. Such nucleic acid sequences may preferably constitute expression cassettes. The following may be mentioned by way of example of the DNA sequences to be expressed in the expression constructs, but not by way of limitation:

i) Positive selection markers:

As a rule, selection markers are required for selecting cells which have successfully undergone homologous recombination or transformation. The selectable marker which has been introduced together with the expression construct confers resistance to a biocide (for example a herbicide such as phosphinothricin, glyphosate or bromoxynil), a metabolism inhibitor such as 2-deoxyglucose-6-phosphate (WO 98/45456) or an antibiotic such as, for example, tetracyclines, ampicillin, kanamycin, G 418, neomycin, bleomycin or hygromycin to the cells which have successfully undergone recombination or transformation. The selection marker permits the selection of the transformed cells from untransformed cells (McCormick et al., Plant Cell Reports 5 (1986), 81-84). Especially preferred selection markers are those which confer resistance to herbicides. Examples of selection markers which may be mentioned are:

DNA sequences which encode phosphinothricin acetyltransferases (PAT), which acetylates the free amino group of the glutamine synthase inhibitor phosphinothricin (PPT) and thus brings about detoxification of the PPT (de Block et al. 1987, EMBO J. 6, 2513-2518) (also referred to as Bialophos® resistance gene (bar)), 5-enolpyruvylshikimate-3-phosphate synthase genes (EPSP synthase genes), which confer resistance to Glyphosate® (N-(phosphonomethyl)glycine), the gox gene, which encodes the Glyphosate®-degrading enzyme (Glyphosate oxidoreductase), the deh gene (encoding a dehalogenase which inactivates Dalapon®), acetolactate synthases which inactivate sulfonylurea and imidazolinone, bxn genes which encode Bromoxynil®-degrading nitrilase enzymes, the kanamycin, or G418, resistance gene (NPTII). The NPTII gene encodes a neomycin phosphotransferase which reduces the inhibitory effect of kanamycin, neomycin, G418 and paromomycin owing to a phosphorylation reaction, the $DOG^R1$ gene. The $DOG^R1$ gene has been isolated from the yeast *Saccharomyces cerevisiae* (EP 0 807 836). It encodes a 2-deoxyglucose-6-phosphate phosphatase which confers resistance to 2-DOG (Randez-Gil et al. 1995, Yeast 11, 1233-1240).

ii) Negative selection markers enable for example the selection of organisms with successfully deleted sequences which encompass the marker gene (Koprek T et al. (1999) The Plant Journal 19(6):719-726). TK thymidine kinase (TK) and diphtheria toxin A fragment (DT-A), codA gene encoding a cytosine deaminase (Gleve A P et al. (1999) Plant Mol Biol. 40(2):223-35; Pereat R I et al. (1993) Plant Mol. Biol 23(4): 793-799; Stougaard J; (1993) Plant J 3:755-761), the cytochrome P450 gene (Koprek et al. (1999) Plant J. 16:719-726), genes encoding a haloalkane dehalogenase (Naested H (1999) Plant J. 18:571-576), the iaah gene (Sundaresan V et al. (1995) Genes & Development 9:1797-1810) or the tms2 gene (Fedoroff N V & Smith D L 1993, Plant J 3: 273-289).

iii) Report genes which encode readily quantifiable proteins and which, via intrinsic color or enzyme activity, ensure the assessment of the transformation efficacy or of the location or timing of expression. Very especially preferred here are genes encoding reporter proteins (see also Schenborn E, Groskreutz D. Mol Biotechnol. 1999; 13(1):29-44) such as "green fluorescence protein" (GFP) (Chui W L et al., Curr Biol 1996, 6:325-330; Leffel S M et al., Biotechniques. 23(5):912-8, 1997; Sheen et al.(1995) Plant Journal 8(5):777-784; Haseloff et al.(1997) Proc Natl Acad Sci USA 94(6):2122-2127; Reichel et al.(1996) Proc Natl Acad Sci USA 93(12):5888-5893; Tian et al. (1997) Plant Cell Rep 16:267-271; WO 97/41228).

Chloramphenicol transferase, luciferase (Millar et al., Plant Mol Biol Rep 1992 10:324-414; Ow et al. (1986) Science, 234:856-859); permits the detection of bioluminescence, β-galactosidase, encodes an enzyme for which a variety of chromogenic substrates are available, β-glucuronidase (GUS) (Jefferson et al., EMBO J. 1987, 6, 3901-3907) or the uidA gene, which encodes an enzyme for a variety of chromogenic substrates, R locus gene product: protein which regulates the production of anthocyanin pigments (red coloration) in plant tissue and thus makes possible the direct analysis of the promotor activity without the addition of additional adjuvants or chromogenic substrates (Dellaporta et al., In: Chromosome Structure and Function: Impact of New Concepts, 18th Stadler Genetics Symposium, 11:263-282, 1988), β-lactamase (Sutcliffe (1978) Proc Natl Acad Sci USA 75:3737-3741), enzyme for a variety of chromogenic substrates (for example PADAC, a chromogenic cephalosporin), xylE gene product (Zukowsky et al. (1983) Proc Natl Acad Sci USA 80:1101-1105), catechol dioxygenase capable of converting chromogenic catechols, alpha-amylase (Ikuta et al. (1990) Bio/technol. 8:241-242), tyrosinase (Katz et al. (1983) J Gene Microbiol 129:2703-2714), enzyme which oxidizes tyrosine to give DOPA and dopaquinone which subsequently form melanine, which is readily detectable, aequorin (Prasher et al. (1985) Biochem Biophys Res Commun 126(3):1259-1268), can be used in the calcium-sensitive bioluminescence detection.

The recombination construct according to the invention and any vectors derived from it may comprise further functional elements. The term "further functional elements" is to be understood in the broad sense. It preferably refers to all those elements which affect the generation, multiplication, function, use or value of the recombination system according to the invention, recombination construct according to the invention or cells or organisms comprising them. The following may be mentioned by way of example, but not by limitation, of the further functional elements.

iv) Replication origins which ensure replication of the expression cassettes or vectors according to the invention in, for example, *E. coli*. Examples which may be mentioned are ORI (origin of DNA replication), the pBR322 ori or the P15A ori (Sambrook et al.: Molecular Cloning. A Laboratory Manual, $2^{nd}$ ed. Cold Spring Harbor Laboratory Press, Cold Spring Harbor, N.Y., 1989).

v) Multiple cloning regions (MCS) enable and facilitate the insertion of one or more nucleic acid sequences.

vi) Sequences which make possible homologous recombination or insertion into the genome of a host organism.

vii) Elements, for example border sequences, which make possible the *agrobacterium*-mediated transfer in plant cells for the transfer and integration into the plant genome, such as, for example, the right or left border of the T-DNA or the vir region.

All of the abovementioned expression cassettes or further functional elements may be located, as mentioned, between the homology sequences A and B. However, they may also be located outside them. This is advantageous in particular in the case of border sequences.

A recombination cassette or expression construct according to the invention for a DSBI enzyme may advantageously be introduced into cells using vectors into which these constructs or cassettes are inserted. Examples of vectors include, for example, plasmids, cosmids, phages, viruses, retroviruses or agrobacteria.

Vectors for expression in *E. coli* are preferably pQE70, pQE60 and pQE-9 (QIAGEN, Inc.); pBluescript vectors, Phagescript vectors, pNH8A, pNH16a, pNH18A, pNH46A (Stratagene Cloning Systems, Inc.); ptrc99a, pKK223-3, pKK233-3, pDR540, pRIT5 (Pharmacia Biotech, Inc.), or combinations thereof.

Preferred vectors for eukaryotic expression encompass pWLNE0, pSV2CAT, pOG44, pXT1 and pSG (Stratagene Inc.); pSVK3, pBPV, pMSG and pSVL (Pharmacia Biotech, Inc.). Inducible vectors which may be mentioned are pTet-Thia, Potter-Splice, pcDNA4/TO, pcDNA4/TO/LacZ, pcDNA6/TR, pcDNA4/TO/Myc-His/LacZ, pcDNA4/TO/Myc-His A, pcDNA4/TO/Myc-His B, pcDNA4/TO/Myc-His C, pVgRXR (Invitrogen, Inc.), the pMAM series (Clontech, Inc.; GenBank Accession No.: U02443), or combinations thereof. These already provide the inducible regulatory control element for example for a chemical inducible expression of a DSBI enzyme. The nucleic acid sequence encoding a DSBI enzyme may be inserted directly into these vectors.

Vectors for the expression in yeast encompass by way of example pYES2, pYD1, pTEF1/Zeo, pYES2/GS, pPICZ,p-GAPZ, pGAPZalph, pPIC9, pPIC3.5, PHIL-D2, PHIL-S1, pPIC3SK, pPIC9K, PA0815 (Invitrogen, Inc.) and combinations thereof.

In an advantageous embodiment, the expression cassette is introduced by means of plasmid vectors. Preferred vectors are those which enable the stable integration of the expression cassette into the host genome.

Another subject matter of the invention relates to eukaryotic transgenic organisms comprising the recombination system according to the invention, and to cells, cell cultures, tissues, parts or propagation material—such as, for example, in the case of plant organisms leaves, roots, seeds, fruit, pollen and the like—derived from such organisms.

Eukaryotic organism, starting organism or host organism refers to higher and lower, single- and multi-celled eukaryotic organisms. Also encompassed are eukaryotic microorganisms such as, for example, yeasts, algae or fungi. Preferred yeasts are *Candida, Saccharomyces, Hansenula* or *Pichia*, with *Saccharomyces cerevisiae* or *Pichia pastoris* (ATCC Accession No. 201178) being particularly preferred. Preferred fungi are *Aspergillus, Trichoderma, Ashbya, Neurospora, Fusarium, Beauveria* or other fungi described in Indian Chem Engr. Section B. Vol 37, No 1,2 (1995) on page 15, Table 6. The filamentous Hemiascomycete *Ashbya gossypii* is particularly preferred.

Host or starting organisms which are preferred in accordance with the invention are, furthermore, animal organisms and cells or tissue derived from them. Animal organisms encompass preferably vertebrates and invertebrates. Especially preferred vertebrates are mammals such as in dogs, cats, sheep, goats, chickens, mice, rats, bovines or horses. Preferred animal cells encompass CHO, COS and HEK293 cells. Preferred invertebrates encompass insect cells such as *Drosophila* S2 and *Spodoptera* Sf9 or Sf21 cells.

Host organisms or starting organisms which are preferred as transgenic organisms are especially plants. Included within the scope of the invention are all genera and species of higher and lower plants of the plant kingdom. Included are furthermore the mature plants, seed, shoots and seedlings, and parts, propagation material (for example seeds and fruit) and cultures, for example cell cultures, derived therefrom. Mature plants are to be understood as meaning plants at any developmental stage beyond the seedling. Seedling is to be understood as meaning a young, immature plant in an early developmental stage.

The recombination system according to the invention may preferably be used for the following plant families: Amaranthaceae, Brassicaceae, Carophyllaceae, Chenopodiaceae, Compositae, Cucurbitaceae, Labiatae, Leguminosae-Papilionoideae, Liliaceae, Linaceae, Malvaceae, Rosaceae, Saxifragaceae, Scrophulariaceae, Solanacea, Tetragoniacea and transgene combinations thereof.

Annual, perennial, monocotyledonour and dicotyledonous plants are preferred host organisms for the generation of transgenic plants. The use of the recombination system, or method according to the invention is furthermore advantageous in all ornamental plants, useful or ornamental trees, flowers, cut flowers, shrubs or turf. Plants which may be mentioned by way of example but not by limitation are angiosperms, bryophytes such as, for example, Hepaticae (hepaticas) and Musci (mosses); pteridophytes such as ferns, horsetail and clubmosses; gymnosperms such as conifers, cycads, ginkgo and Gnetaceae; algae such as Chlorophyceae, Phaeophpyceae, Rhodophyceae, Myxophyceae, Xanthophyceae, Bacillariophyceae (diatoms) and Euglenophyceae.

Plants for the purposes of the invention comprise by way of example and not by way of limitation the families of the Rosaceae such as rose, Ericaceae such as rhododendrons and azaleas, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, Iridaceae such as gladioli, iris, freesia and crocus, Compositae such as marigold, Geraniaceae such as geraniums, Liliaceae such as drachaena, Moraceae such as ficus, Araceae such as philodendron and many others.

Flowering plants which may be mentioned by way of example but not by limitation are the families of the Leguminosae such as pea, alfalfa and soya; Gramineae such as rice, maize, wheat; Solanaceae such as tobacco and many others; the family of the Umbelliferae, particularly the genus *Daucus* (very particularly the species *carota* (carrot)) and *Apium* (very particularly the species *graveolens dulce* (celery)) and many others; the family of the Solanacea, particularly the genus *Lycopersicon*, very particularly the species *esculentum* (tomato) and the genus *Solanum*, very particularly the species *tuberosum* (potato) and *melongena* (aubergine) and many others; and the genus *Capsicum*, very particularly the species *annum* (peppers) and many others; the family of the Leguminosae, particularly the genus *Glycine*, very particularly the species *max* (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidopsis*, very particularly the species *thaliana* and many others; the family of the Compositae, particularly the genus *Lactuca*, very particularly the species *sativa* (lettuce) and many others.

The transgenic plants according to the invention are selected in particular among monocotyledonous crop plants, such as, for example, cereals such as wheat, barley, sorghum and millet, rye, triticale, maize, rice or oats, and sugar cane. The transgenic plants according to the invention are furthermore selected in particular from among dicotyledonous crop plants such as, for example, Brassicaceae such oilseed rape, cress, *Arabidopsis*, cabbages or canola, Leguminosae such as soya, alfalfa, peas, beans or peanut. Solanaceae such as potato, tobacco, tomato, aubergine or peppers, Asteraceae such as sunflower, Tagetes, lettuce or Calendula. Cucurbitaceae such as melon, pumpkin/squash or courgette, and linseed, cotton, hemp. Flax, red pepper, carrot, sugar beet and the various tree, nut and wine species.

Especially preferred are *Arabidopsis thaliana, Nicotiana tabacum* and oilseed rape and all genera and species which are used as food or feedstuffs, such as the above-described cereal species, or which are suitable for the production of oils, such as oil crops (such as, for example, oilseed rape), nut species, soya, sunflower, pumpkin/squash and peanut.

Plant organisms are furthermore, for the purposes of the invention, other organisms which are capable of photosynthetic activity, such as, for example, algae or cyanobacteria, and also mosses. Preferred algae are green algae, such as, for example, algae of the genus *Haematococcus, Phaedactylum tricornatum, Volvox* or *Dunaliella*.

The generation of a transformed organism or a transformed cell requires introducing the DNA in question into the host cell in question. A multiplicity of methods is available for this procedure, which is termed transformation (see also Keown et al. 1990 Methods in Enzymology 185:527-537). For example, the DNA can be introduced directly by microinjection or by bombardment with DNA-coated microparticles. Also, the cell can be permeabilized chemically, for example using polyethylene glycol, so that the DNA can enter the cell by diffusion. The DNA can also be introduced by protoplast fusion with other DNA-containing units such as minicells, cells, lysosomes or liposomes. Another suitable method of introducing DNA is electroporation, where the cells are permeabilized reversibly by an electrical pulse. Preferred general methods which may be mentioned are the calcium-phosphate-mediated transfection, the DEAE-dextran-mediated transfection, the cationic lipid-mediated transfection, electroporation, transduction and infection. Such methods are known to the skilled worker and described, for example, in Davis et al., Basic Methods In Molecular Biology (1986).

In plants, methods for transforming and regenerating plants from plant tissues or plant cells with which the skilled worker is familiar are exploited for transient or stable transformation. Suitable methods are especially protoplast transformation by means of polyethylene-glycol-induced DNA uptake, biolistic methods such as the gene gun ("particle bombardment" method), electroporation, the incubation of dry embryos in DNA-containing solution, sonication and microinjection, and the transformation of intact cells or tissues by micro- or macroinjection into tissues or embryos, tissue electroporation, incubation of dry embryos in DNA-containing solution or vacuum infiltration of seeds. In the case of injection or electroporation of DNA into plant cells, the plasmid used need not meet any particular requirement. Simple plasmids such as those of the pUC series may be used. If intact plants are to be regenerated from the transformed cells, the presence of an additional selectable marker gene on the plasmid is useful.

Any plant tissue may act as target material. Likewise, expression may take place in callus, embryogenic tissue or somatic embryos.

In addition to these "direct" transformation techniques, transformation can also be carried out by bacterial infection by means of *Agrobacterium tumefaciens* or *Agrobacterium rhizogenes*. These strains contain a plasmid (Ti or Ri plasmid). Part of this plasmid, termed T-DNA (transferred DNA), is transferred to the plant following agrobacterial infection and integrated into the genome of the plant cell.

The recombination construct or the expression cassette for the DSBI enzyme is preferably integrated into specific plasmids, either into a shuttle, or intermediate, vector or into a binary vector). If, for example, a Ti or Ri plasmid is to be used for the transformation, at least the right border, but in most cases the right and the left border, of the Ti or Ri plasmid T-DNA is linked with the expression cassette to be introduced as a flanking region. Binary vectors are preferably used. Binary vectors are capable of replication both in *E. coli* and in *Agrobacterium*. As a rule, they contain a selection marker gene and a linker or polylinker flanked by the right or left T-DNA flanking sequence. They can be transformed directly into *Agrobacterium* (Holsters et al., Mol. Gen. Genet. 163 (1978), 181-187). The selection marker gene permits the selection of transformed agrobacteria and is, for example, the nptII gene, which imparts resistance to kanamycin. The *agrobacterium*, which acts as host organism in this case, should already contain a plasmid with the vir region. The latter is required for transferring the T-DNA to the plant cell. An *agrobacterium* thus transformed can be used for transforming plant cells.

The use of *Agrobacterium tumefaciens* for the transformation of plants using tissue culture explants has been described by Horsch et al. (Horsch RB (1986) Proc Natl Acad Sci USA 83(8):2571-2575), Fraley et al. (Fraley et al. 1983, Proc. Natl. Acad. Sci. USA 80, 4803-4807) and Bevans et al. (Bevans et al. 1983, Nature 304, 184-187). Many strains of *Agrobacterium tumefaciens* are capable of transferring genetic material—for example the recombination constructs according to the invention—, such as, for example, the strains EHA101 [pEHA101], EHA105[pEHA105], LBA4404[pAL4404], C58C1[pMP90]and C58C1[pGV2260]. The strain EHA101 [pEHA101] has been described by Hood et al. (Hood E E et al. (1996) J Bacteriol 168(3):1291-1301), the strain EHA105 [pEHA105] by Hood et al. (Hood et al. 1993, Transgenic Research 2, 208-218), the strain LBA4404[pAL4404] by Hoekema et al. (Hoekema et al. 1983, Nature 303, 179-181), the strain C58C1[pMP90] by Koncz and Schell (Koncz and Schell 1986, Mol. Gen. Genet. 204, 383-396), and the strain C58C1[pGV2260] by Deblaere et al. (Deblaere et al. 1985, Nucl. Acids Res. 13, 4777-4788).

The agrobacterial strain employed for the transformation comprises, in addition to its disarmed Ti plasmid, a binary plasmid with the T-DNA to be transferred, which, as a rule, comprises a gene for the selection of the transformed cells and the gene to be transferred. Both genes must be equipped with transcriptional and translational initiation and termination signals. The binary plasmid can be transferred into the agrobacterial strain for example by electroporation or other transformation methods (Mozo & Hooykaas 1991, Plant Mol. Biol. 16, 917-918). Coculture of the plant explants with the agrobacterial strain is usually performed for two to three days.

A variety of vectors could, or can, be used. In principle, one differentiates between those vectors which can be employed for the *agrobacterium*-mediated transformation or agroinfection, i.e. which comprise the recombination constructs, or the expression cassette, for the expression of the DSBI enzyme within a T-DNA, which indeed permits stable integration of the T-DNA into the plant genome. Moreover, border-sequence-free vectors may be employed, which can be transformed into the plant cells for example by particle bombardment, where they can lead both to transient and to stable expression.

The use of T-DNA for the transformation of plant cells has been studied and described intensively (EP 120516; Hoekema, In: The Binary Plant Vector System, Offsetdrukkerij Kanters B. V., Alblasserdam, Chapter V; Fraley et al., Crit. Rev. Plant. Sci., 4:1-46 and An et al., EMBO J. 4 (1985), 277-287). Various binary vectors are known, some of which are commercially available such as, for example, pBIN19 (Clontech Laboratories, Inc. USA).

To transfer the DNA to the plant cell, plant explants are cocultured with *Agrobacterium tumefaciens* or *Agrobacterium rhizogenes*. Starting from infected plant material (for example leaf, root or stalk sections, but also protoplasts or suspensions of plant cells), intact plants can be regenerated using a suitable medium which may contain, for example, antibiotics or biocides for selecting transformed cells. The plants obtained can then be screened in the presence of the DNA introduced, in this case the recombination construct or the expression cassette for the DSBI enzyme according to the invention. As soon as the DNA has integrated into the host genome, the genotype in question is, as a rule, stable and the insertion in question is also found in the subsequent generations. As a rule, the expression cassette integrated contains a selection marker which confers a resistance to a biocide (for example a herbicide) or an antibiotic such as kanamycin, G 418, bleomycin, hygromycin or phosphinotricin and the like to the transformed plant. The selection marker permits the selection of transformed cells (McCormick et al., Plant Cell Reports 5 (1986), 81-84). The plants obtained can be cultured and hybridized in the customary fashion. Two or more generations should be grown in order to ensure that the genomic integration is stable and hereditary.

The abovementioned methods are described, for example, in B. Jenes et al., Techniques for Gene Transfer, in: Transgenic Plants, Vol. 1, Engineering and Utilization, edited by S. D. Kung and R. Wu, Academic Press (1993), 128-143 and in Potrykus, Annu. Rev. Plant Physiol. Plant Molec. Biol. 42 (1991), 205-225). The construct to be expressed is preferably cloned into a vector which is suitable for the transformation of *Agrobacterium tumefaciens*, for example pBin19 (Bevan et al., Nucl. Acids Res. 12 (1984), 8711).

*Agrobacterium*-mediated transformation is suited best to dicotyledonous plant cells, whereas the direct transformation techniques are suitable for any cell type.

Transformed cells, i.e. those which comprise the DNA integrated into the DNA of the host cell, can be selected from untransformed cells if a selectable marker is part of the DNA introduced. A marker can be, for example, any gene which is capable of conferring a resistance to antibiotics or herbicides. Transformed cells which express such a marker gene are capable of surviving in the presence of concentrations of a suitable antibiotic or herbicide which kill an untransformed wild type. Various positive and negative selection markers are described hereinabove. Examples are the bar gene, which confers resistance to the herbicide phosphinothricin (Rathore K S et al., Plant Mol Biol. March 1993; 21(5):871-884), the nptII gene, which confers resistance to kanamycin, the hpt gene, which confers resistance to hygromycin, or the EPSP gene, which confers resistance to the herbicide Glyphosate.

As soon as a transformed plant cell has been generated, an intact plant can be obtained using methods known to the skilled worker. For example, callus cultures are used as starting material. The formation of shoot and root can be induced in this as yet undifferentiated cell biomass in the known fashion. The shoots obtained can be planted and cultured.

Also in accordance with the invention are cells, cell cultures, parts—such as, for example, in the case of transgenic plant organisms, roots, leaves and the like—derived from the above-described transgenic organisms, and transgenic propagation material (such as seeds or fruits).

Genetically modified plants according to the invention which can be consumed by humans or animals can also be used as food or feedstuffs, for example directly or following processing known per se. Here, the deletion of, for example, resistances to antibiotics and/or herbicides, as are frequently introduced when generating the transgenic plants, makes sense for reasons of customer acceptance, but also product safety.

A further subject matter of the invention relates to the use of the above-described transgenic organisms according to the invention and the cells, cell cultures, parts —such as, for example, in the case of transgenic plant organisms, roots, leaves and the like—derived from them, and transgenic propagation material such as seeds or fruits, for the production of food or feedstuffs, pharmaceuticals or fine chemicals. Here again, the deletion of, for example, resistances to antibiotics and/or herbicides is advantageous for reasons of customer acceptance, but also product safety.

Fine chemicals is understood as meaning enzymes, vitamins, amino acids, sugars, fatty acids, natural and synthetic flavors, aromas and colorants widely usable. Especially preferred is the production of tocopherols and tocotrienols, and of carotenoids. Culturing the transformed host organisms, and isolation from the host organisms or from the culture medium, is performed by methods known to the skilled worker. The production of pharmaceuticals such as, for example, antibodies or vaccines, is described by Hood E E, Jilka J M. (1999) Curr Open Biotechnol. 10(4):382-386; Ma J K and Vine N D (1999) Curr Top Microbiol Immunol. 236:275-92).

Figure 2:
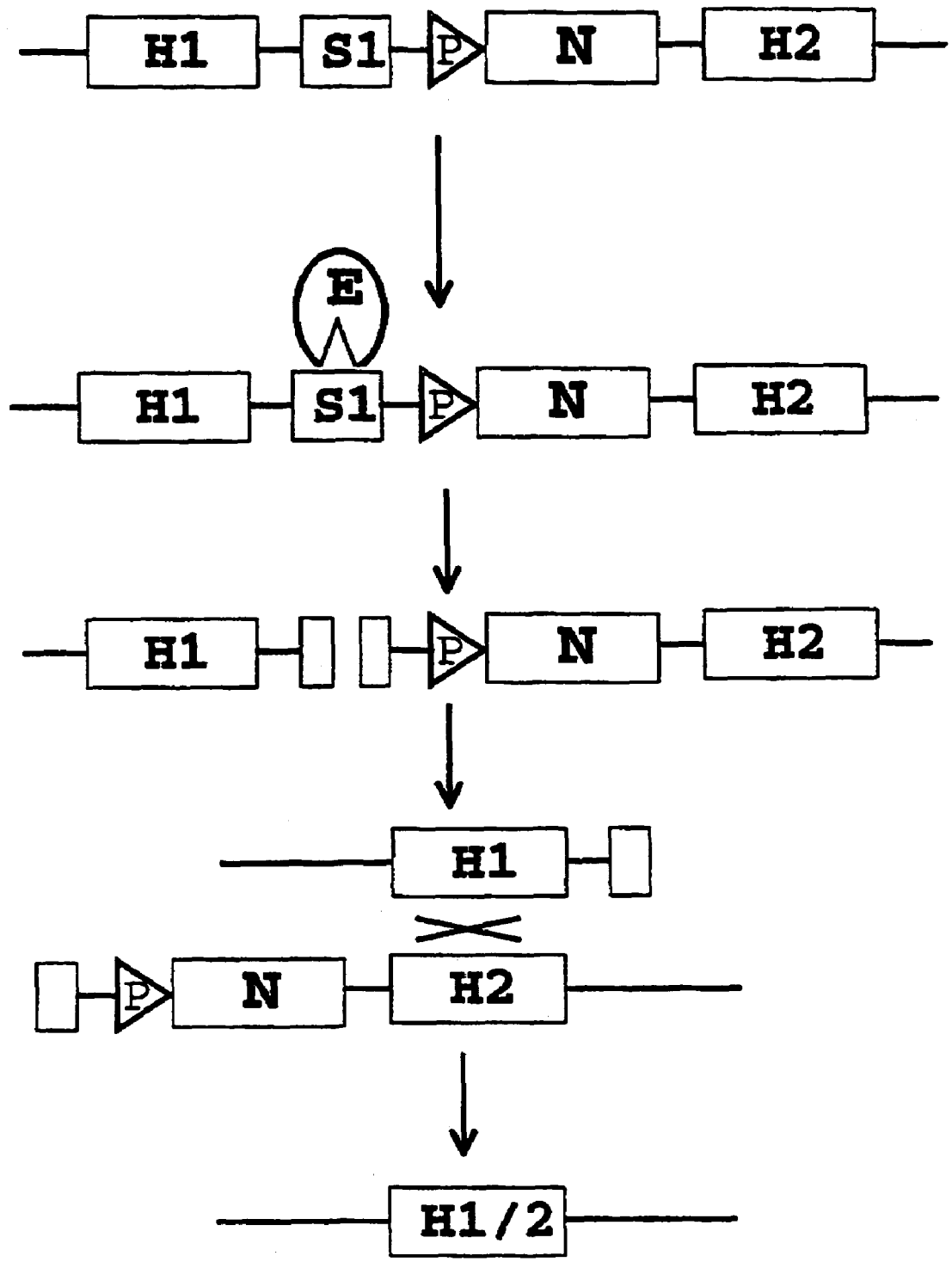
FIG. 2. Diagram of a preferred embodiment of the invention.
Figure 3:
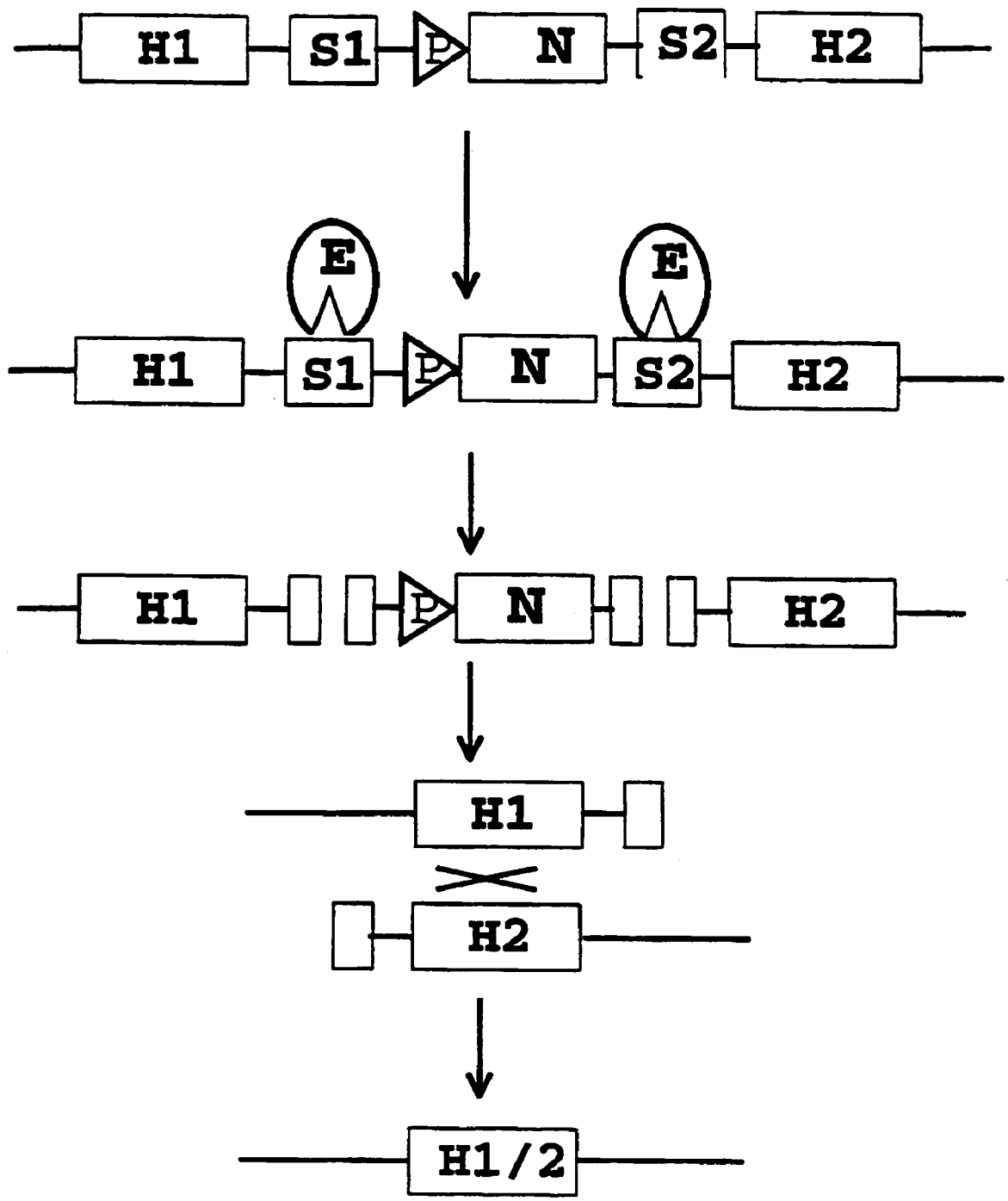
FIG. 3. Diagram of another preferred embodiment of the invention.

The recombination system or method according to the invention furthermore offers various advantageous uses which can not be achieved with the deletion methods described in the prior art. Various use examples are described herein by way of example, but not by limitation:

Simple deletion of a nucleic acid sequence from the chromosomal DNA of an organism:

Using any homology sequences A and B, nucleic acid sequences located between them can be deleted. The sequence which is the result of the recombination of the homology sequences A and B remains in the genome. The method is suitable for example for removing, from the chromosomal DNA, selection markers after a transgenic organism, for example a transgenic plant, has been generated. The method is shown schematically in FIGS. 2 and 3, FIG. 2 showing the variant with one recognition sequence for the site-directed induction of DNA double-strand breaks and FIG. 3 showing the variant with two recognition sequences for the site-directed induction of DNA double-strand breaks.

Complete deletion of recombinantly introduced heterologous nucleic acid sequences from the chromosomal DNA of an organism:

Using homology sequences A and B, which are homologous to certain sequences of the organism, the expression construct can be introduced into the organism by homologous recombination. Using the recombination system or method according to the invention, the nucleic acid sequences located between the homology sequences would be deleted. The induced homologous recombination between homology sequences A and B restores the original sequence. All of the construct is removed from the chromosomal DNA. The method is suitable for example for removing selection markers from the chromosomal DNA after a transgenic plant has been generated. Furthermore, the system or method according to the invention is suitable for expressing certain proteins transiently in order to achieve an advantageous effect and then to switch them off using an induced DSBI enzyme expression or activity by irreversibly removing the gene in question from the genome. The method is shown schematically in FIG. 4, the variant with two recognition sequences for the site-directed induction of DNA double-strand breaks being shown. The system can also be realized using one recognition sequence; however, two cleavage sites are advantageous in the case of larger insertions between the homology sequences A and B since this allows the deletion efficacy and homologous recombination efficacy to be increased further (further recognition sequences may be located within the sequence region to be deleted).

Figure 5:
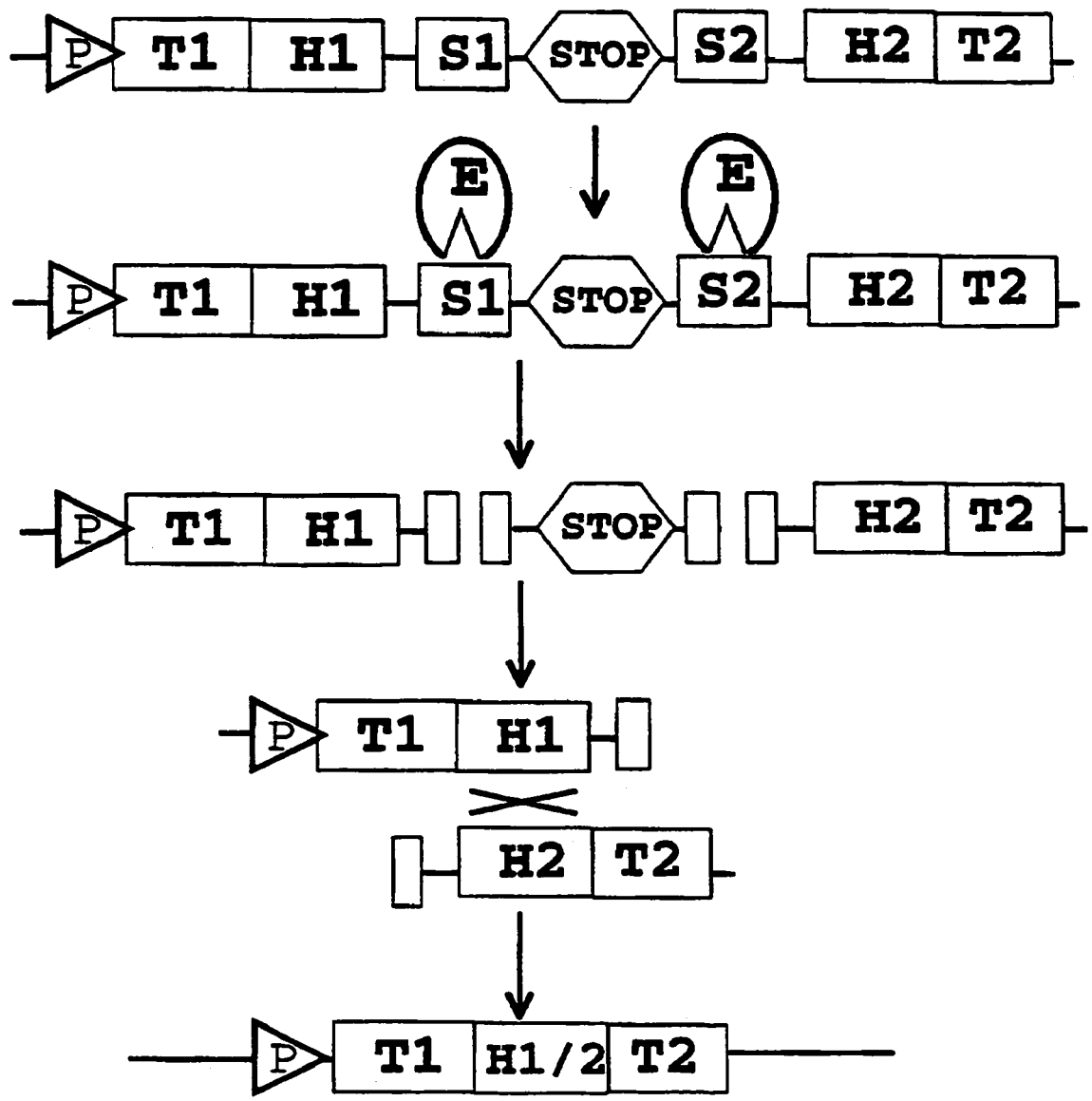
FIG. 5. Diagram of another preferred embodiment of the invention.
Figure 6:
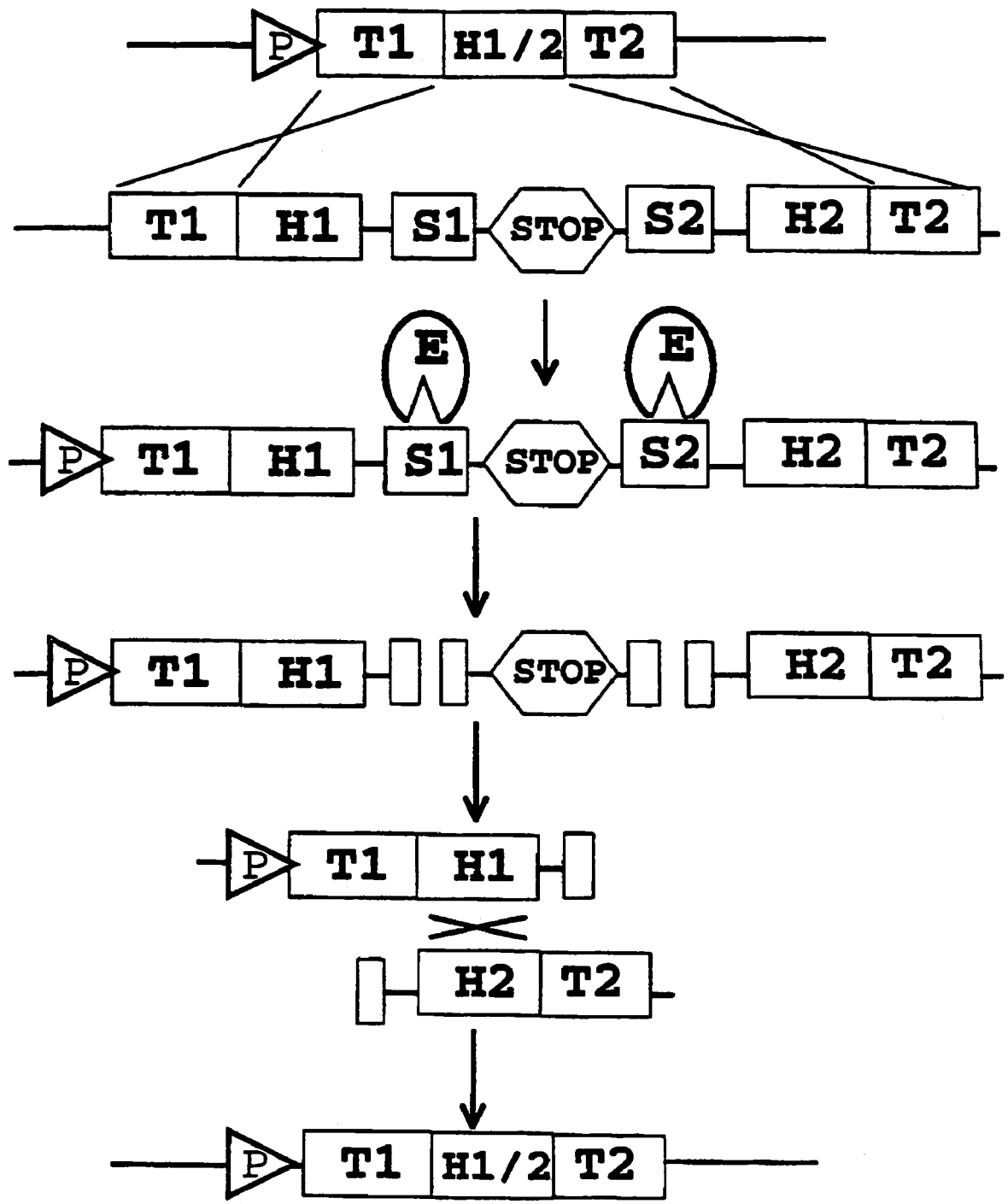
FIG. 6. Diagram of another preferred embodiment of the invention.
Figure 7A:
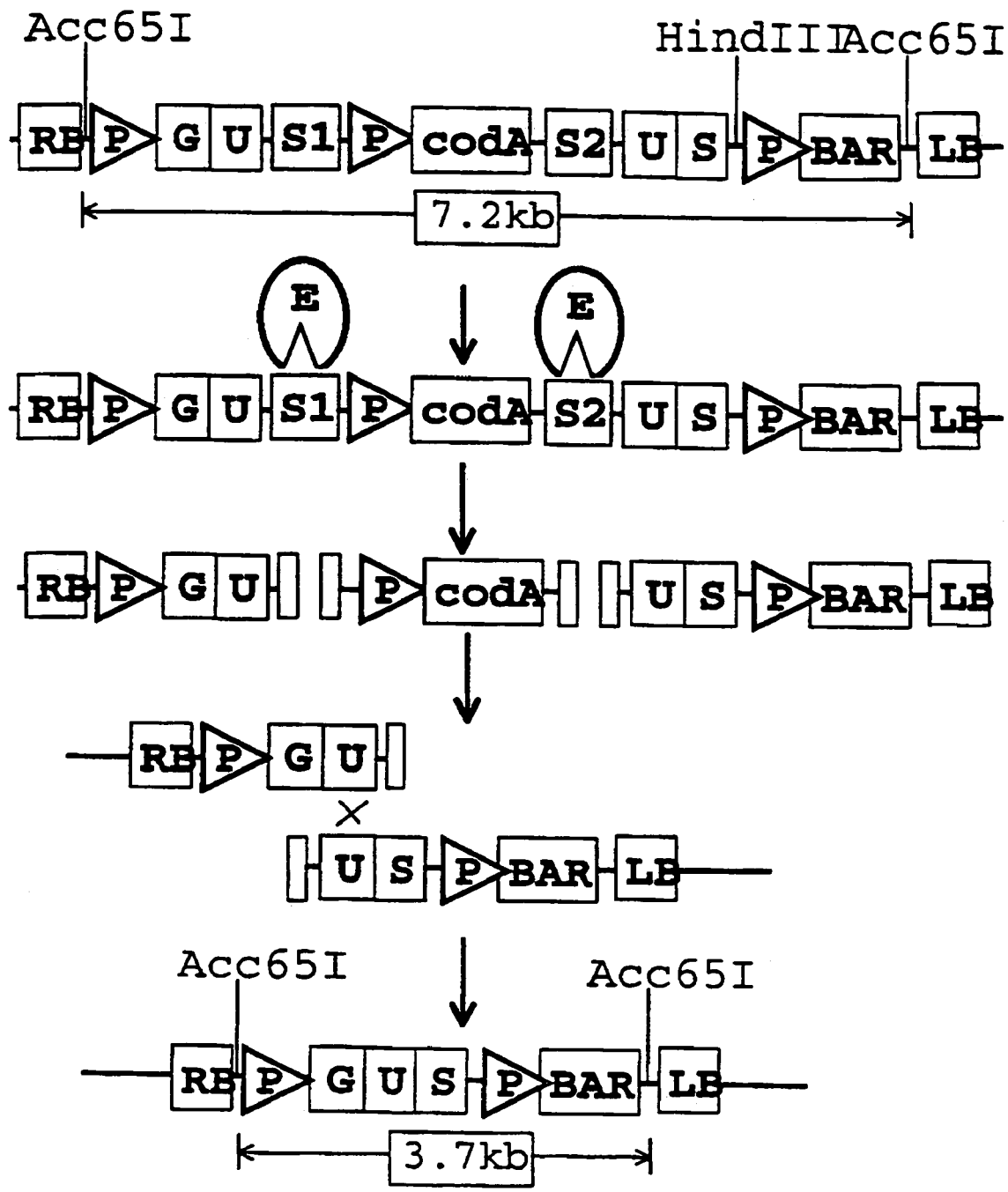
FIG. 7a illustrates the appearance of double-strand breaks and the homologous recombination between the homologous U sequences, brought about by the action of the DSBI enzyme, whereby firstly the sequences located between the homologous U sequences are deleted and secondly the GUS gene is restored.

Induced gene activation by the site-directed deletion of nucleic acid sequences:

Using homology sequences A and B, whose homologous recombination restores for example a complete open reading frame of a protein, or a functional promotor, the inducible expression of target proteins can be realized as a function of the presence of the DSBI enzyme. Using the recombination system or method according to the invention, the nucleic acid sequences located between the homology sequences would be deleted. The method is shown schematically in FIGS. 5 and 6, FIG. 6 showing a specific embodiment of the general method shown in FIG. 5 in which the recombination construct is inserted into an endogenous gene at an earlier point in time by means of homologous recombination, thus enabling this gene to be inducibly activated as a function of the presence of the DSBI enzyme. FIG. 7*a* illustrates the system of gene activation with reference to a specific use example where the β-glucuronidase (GUS) gene is reconstituted using the system or method according to the invention, enabling a color reaction to take place (see description to FIG. 7a and Examples).

Figure 8:
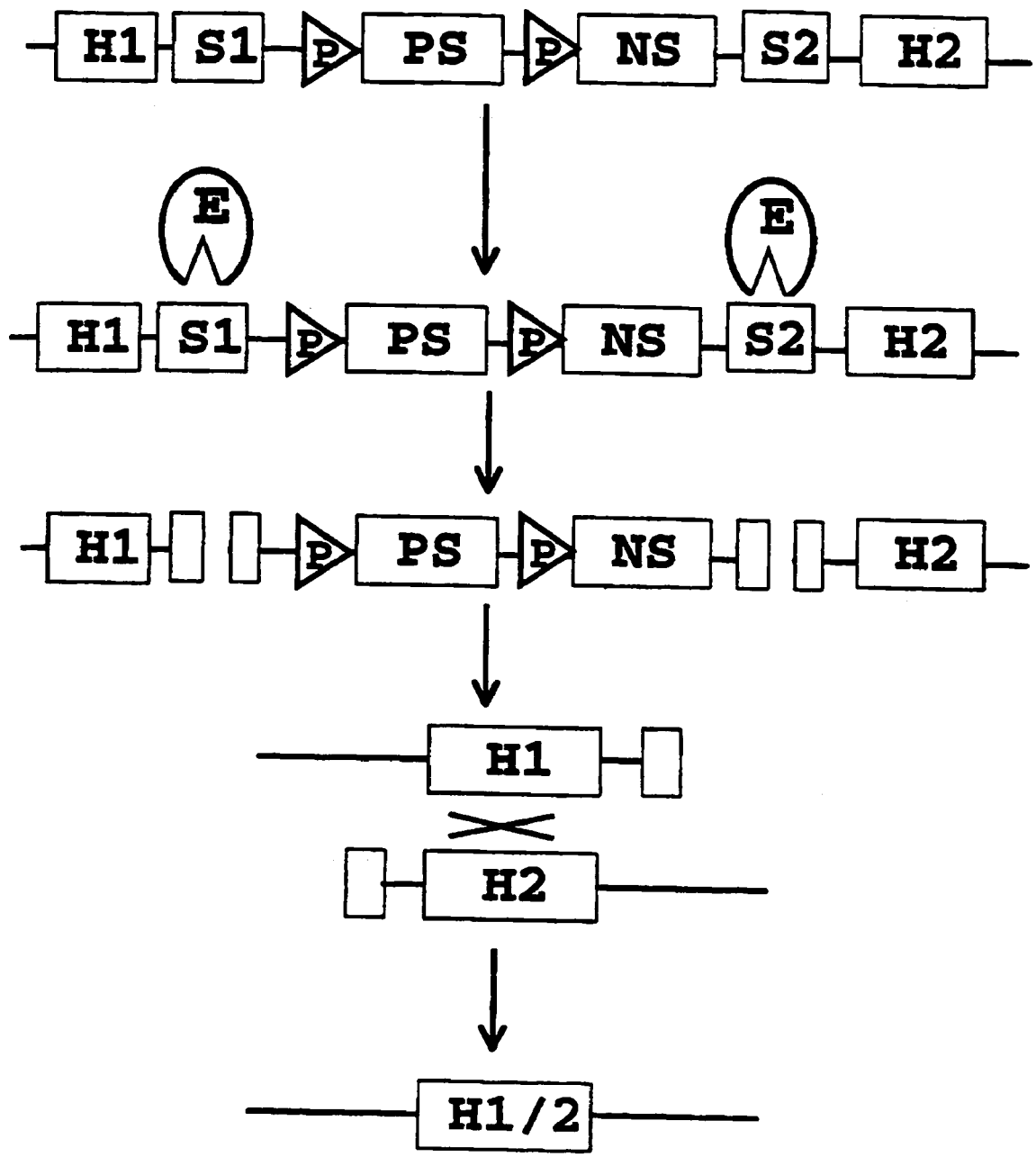
FIG. 8. Diagram of another preferred embodiment of the invention.

Readily selectable system for the deletion of a nucleic acid sequence from the chromosomal DNA of an organism:

In a preferred embodiment, the recombination construct comprises a positive and a negative selection marker (and, if appropriate, further nucleic acid sequences to be deleted) in such a way that both markers are deleted when the double-strand breaks are induced. Such a system is shown in FIGS. 8 and 9(A). Moreover, the expression cassette for the DSBI enzyme may also be present between the homology sequences (FIG. 10(B)), expression preferably being effected under the control of an inducible promotor (Pi) (for example: Aoyama T and Chua N H (1997) Plant J 11:605-612; Caddick M X et al. (1998) Nat. Biotechnol 16:177-180). As already described, further nucleic acid sequences may be present (FIG. 9(C)).

Expression of the DSBI enzyme leads in both cases to the elimination of the DNA sequences located between the two recognition sequences and the recombination of the homologous sequences. Since the cells simultaneously lose a negative selection marker, the cells with a successful deletion can be identified by means of selection (Gleave A P et al. (1999) Plant Mol Biol. 40:223-235).

In the case of plant cells, for example, the resulting cells can be used for regenerating and propagating the corresponding intact plants, which now no longer contain any marker genes.

Genetic Manipulation of the Host Genome:

The recombination system or method according to the invention can be used for in-situ modifications of the host genome. Thus, for example, a homology sequence may already exist endogenously in the genome. After insertion of the second homology sequence, which is linked with a DSBI enzyme recognition sequence, any regulatory or coding sequences located between the homology sequences A and B are eliminated from the genome.

At the same time, it is conceivable that the recombination construct encompasses regulatory or coding sequences which are eliminated from the organism once deletion has taken place. Thus, it is possible for example to regulate transiently an endogenous gene in a site-directed fashion.

In a further preferred embodiment, the efficacy of the recombination system is increased by combination with systems which promote homologous recombination. Such systems are described and encompass, for example, the expression of proteins such as RecA or the treatment with PARP inhibitors. It has been demonstrated that the intrachromosomal homologous recombination in tobacco plants can be increased by using PARP inhibitors (Puchta H et al. (1995) Plant J. 7:203-210). Using these inhibitors, the homologous recombination rate in the recombination constructs after induction of the sequence-specific DNA double-strand break, and thus the efficacy of the deletion of the transgenesequences, can be increased further. Various PARP inhibitors may be employed for this purpose. Preferably encompassed are inhibitors such as 3-aminobenzamide, 8-hydroxy-2-methylquinazolin-4-one (NU1025), 1,11b-dihydro-[2H]benzopyrano[4,3,2-de]isoquinolin-3-one (GPI 6150), 5-aminoisoquinolinone, 3,4-dihydro-5-[4-(1-piperidinyl)butoxy]-1(2H)-isoquinolinone, or the compounds described in WO 00/26192, WO 00/29384, WO 00/32579, WO 00/64878, WO 00/68206, WO 00/67734, WO 01/23386 and WO 01/23390.

In addition, it was possible to increase the frequency of various homologous recombination reactions in plants by expressing the *E. coli* RecA gene (Reiss B et al. (1996) Proc Natl Acad Sci USA 93(7):3094-3098). Also, the presence of the protein shifts the ratio between homologous and illegitimate DSB repair in favor of homologous repair (Reiss B et al. (2000) Proc Natl Acad Sci USA 97(7):3358-3363). Reference may also be made to the methods described in WO 97/08331 for increasing the homologous recombination in plants. A further increase in the efficacy of the recombination system might be achieved by the simultaneous expression of the RecA gene or other genes which increase the homologous recombination efficacy (Shalev G et al. (1999) Proc Natl Acad Sci USA 96(13):7398-402). The above-stated systems for promoting homologous recombination can also be advantageously employed in cases where the recombination construct is to be introduced in a site-directed fashion into the genome of a eukaryotic organism by means of homologous recombination.

Sequences:

1. SEQ ID NO: 1

Nucleic acid sequence for the I-SceI homing endonuclease.

2. SEQ ID NO:2

Protein sequence for the I-SceI homing endonuclease.

3. SEQ ID NO:3

Nucleic acid sequence for fusion protein of I-ChuI homing endonuclease and N-terminal nuclear localization sequence.

4. SEQ ID NO:4

Protein sequence for fusion protein of I-ChuI homing endonuclease and N-terminal nuclear localization sequence.

5. SEQ ID NO:5

Nucleic acid sequence for fusion protein of I-CreI homing endonuclease and N-terminal nuclear localization sequence.

6. SEQ ID NO:6

Protein sequence for fusion protein of I-CreI homing endonuclease and N-terminal nuclear localization sequence.

7. SEQ ID NO:7

Nucleic acid sequence for fusion protein of I-CpaI homing endonuclease and N-terminal nuclear localization sequence.

8. SEQ ID NO:8

Protein sequence for fusion protein of I-CpaI homing endonuclease and N-terminal nuclear localization sequence.

9. SEQ ID NO:9

Nucleic acid sequence for fusion protein of I-CpaII homing endonuclease and N-terminal nuclear localization sequence.

10. SEQ ID NO:10

Protein sequence for fusion protein of I-CpaII homing endonuclease and N-terminal nuclear localization sequence.

11. SEQ ID NO: 11: oligonucleotide primer OPN1

```
5'-CGG CTC GAG CTA CGG GGA CGA TTT CTT TTT TTC
AC-3'
```

12. SEQ ID NO: 12: oligonucleotide primer OPN2

```
5'-CGG CTC GAG TAC CTA GAA TAC AAA GAA GAG GAA GAA
GAA ACC TCT ACA GAA GAA GCC ATG GGT CCA AAG AAA
AAG AGA AAG GTT ATC AT GAA TAC AAA ATA TAA TAA AGA
GTT CTT ACT C-3'
```

13. SEQ ID NO: 13: oligonucleotide primer OPN3

```
5'-CGG CTC GAG TAC CTA GAA TAC AAA GAA GAG GAA GAA
GAA ACC TCT ACA GAA GAA GCC ATG GGT CCA AAG AAA
AAG AGA AAG GTT ATC ATG GAC ATT AAT CCT CAA TGG
ATT ACA GG-3'
```

14. SEQ ID NO: 14: oligonucleotide primer OPN4

```
5'-CGG CTC GAG TTA CTC GCC AGT TTC TTC AAA ACG-3'
```

15. SEQ ID NO: 15: oligonucleotide primer OPN5

```
5'-CGG CTC GAG TAC CTA GAA TAC AAA GAA GAG GAA GAA
GAA ACC TCT ACA GAA GAA GCC ATG GGT CCA AAG AAA
AAG AGA AAG GTT ATC ATG ACC GAT TCT AAA TCT AGA
AAC AAC-3'
```

16. SEQ ID NO: 16: oligonucleotide primer OPN6

```
5'-CGG CTC GAG CTA AAG GTG GCC TTT ATT GCC ATC
AG-3'
```

17. SEQ ID NO: 17: oligonucleotide primer OPN7

```
5'-CGG CTC GAG TAC CTA GAA TAC AAA GAA GAG GAA GAA
GAA ACC TCT ACA GAA GAA GCC ATG GGT CCA AAG AAA
AAG AGA AAG GTT ATC ATG TCA TTA ACA CAA CAA CAA
AAA GAC-3'
```

18. SEQ ID NO: 18: oligonucleotide primer OPN8

```
5'-CGG CTC GAG CTA AAG GTG GCC TTT ATT GCC ATC
AG-3'
```

19. SEQ ID NO: 19: oligonucleotide primer OPN9

```
5'-CGG CTC TAG AGC GGC CGC CTA GGG ATA ACA GGG TAA
TAG AAT CCC ACA AAA ATC TGA GCT AAA CAG 3'
```

20. SEQ ID NO: 20: oligonucleotide primer OPN10

```
5'-CGG AAG CTT CGT CAC CAA TCC CAA TTC GAT CTA
C-3'
```

21. SEQ ID NO: 21: oligonucleotide primer OPN11

```
5'-CGG AAG CTT CCA CTT GCA AAG TCC CGC TAG TGC
C-3'
```

22. SEQ ID NO: 22: oligonucleotide primer OPN12

```
5'-CGG CTC TAG ACT ATT ACC CTG TTA TCC CTA GGC CCG
ATC TAG TAA CAT AGA TGA CAC CGC GCG CG 3'
```

23. SEQ ID NO: 23: oligonucleotide primer OPN13

```
5'-CGG AAG CTT CGT CAC CAA TCC CAA TTC GAT CTA
C-3'
```

24. SEQ ID NO: 24: oligonucleotide primer OPN14

```
5'-CGG AAG CTT CCA CTT GCA AAG TCC CGC TAG TGC
C-3'
```

25. SEQ ID NO: 25: oligonucleotide primer OPN15

```
5'-CTA GTA CAA AAC GTC GTG AGA CAT TTT AAT CTG AAG
GTT TGG CAC CTC GAT GTC GGC TCA TC-3'
```

26. SEQ ID NO: 26: oligonucleotide primer OPN16

```
5'-CTA GGA TGA GCC GTC ATC GAG GTG CCA AAC CTT CAG
ATT AAA ATG TCT CAC GAC GTT TTG TA-3'
```

27. SEQ ID NO: 27: oligonucleotide primer OPN17

```
5'-CTA GTC CGA AAA CGC CGT GAG ACA TAT TGG TTA CGA
TCC TAA GGT AGC GAA ATT CAC CCG GTA ACT CTG TGC
CAG-3'
```

28. SEQ ID NO: 28: oligonucleotide primer OPN18

```
5'-CTA GCT GGC ACA GAG TTA CCG GGT GAA TTT CGC TAC
CTT AGG ATC GTA ACC AAT ATG TCT CAC GGC GTT TTC
GGA-3'
```

29. SEQ ID NO: 29: nuclear localization sequence NLS1

```
N-Pro-lys-Thr-Lys-Arg-Lys-Val-C
```

30. SEQ ID NO: 30: nuclear localization sequence NLS2

```
N-Pro-Lys-Lys-Lys-Arg-Lys-Val-C    (SEQ ID NO: 30)
```

Figures

The following abbreviations apply to the figures in general:

H1: Homology sequence A
H2: Homology sequence B
H1/2: Sequence as the result of homologous recombination of H1 and H2
S1: First recognition sequence for the site-directed induction of DNA double-strand breaks
S2: Second recognition sequence for the site-directed induction of DNA double-strand breaks.
E: DSBI enzyme
P: Promotor or other genetic control element
N: Further nucleic acid sequence
NS: Negative selection marker
PS: Positive selection marker
T1: Front part, for example of a gene or open reading frame
T2: Back part, for example of a gene or open reading frame
STOP: Interruption of a gene or open reading frame by, for example, stop codons or reading-frame shifts.

FIG. 1: Diagram of the principle of the invention. Sequences in the genome can be eliminated efficiently when they are flanked by the homology sequences H1 and H2 and when a cleavage site (S1) for a DSBI enzyme is located between the homology sequences. Owing to the action of the DSBI enzyme (E) on this recombination cassette (H1-S1-H2), double-strand breaks are formed at the cleavage site S1 and the sequences located between H1 and H2 are eliminated.

FIG. 2: Preferred embodiment. Sequences—in the present case for example an expression cassette consisting of a promotor (P) and a further nucleic acid sequence (N) to be expressed (for example a selection marker)—can be eliminated efficiently from the chromosomal DNA when the are flanked by the homology sequences H1 and H2 and when a cleavage site (S1) for a DSBI enzyme is located between the homology sequences. Owing to the action of the DSBI enzyme (E) on this recombination cassette (H1-S1-P-N-H2), double-strand breaks are formed at the cleavage site S1 and the sequences located between H1 and H2 are eliminated. The cleavage site S1 may also be located behind or within the expression cassette.

FIG. 3: Preferred embodiment. Sequences—in the present case for example an expression cassette consisting of a promotor (P) and a further nucleic acid sequence (N) to be expressed (for example a selection marker)—can be eliminated particularly efficiently from the chromosomal DNA when they are flanked by the homology sequences H1 and H2 and when in each case one cleavage site (S1 and S2) for a DSBI enzyme is located before and after the nucleic acid sequence to be deleted. Owing to the action of the DSBI enzyme (E) on this recombination cassette (H1-S1-P-N-S2-H2), double-strand breaks are formed at the cleavage sites S1 and S2 and the sequences located between H1 and H2 are eliminated.

Figure 4:
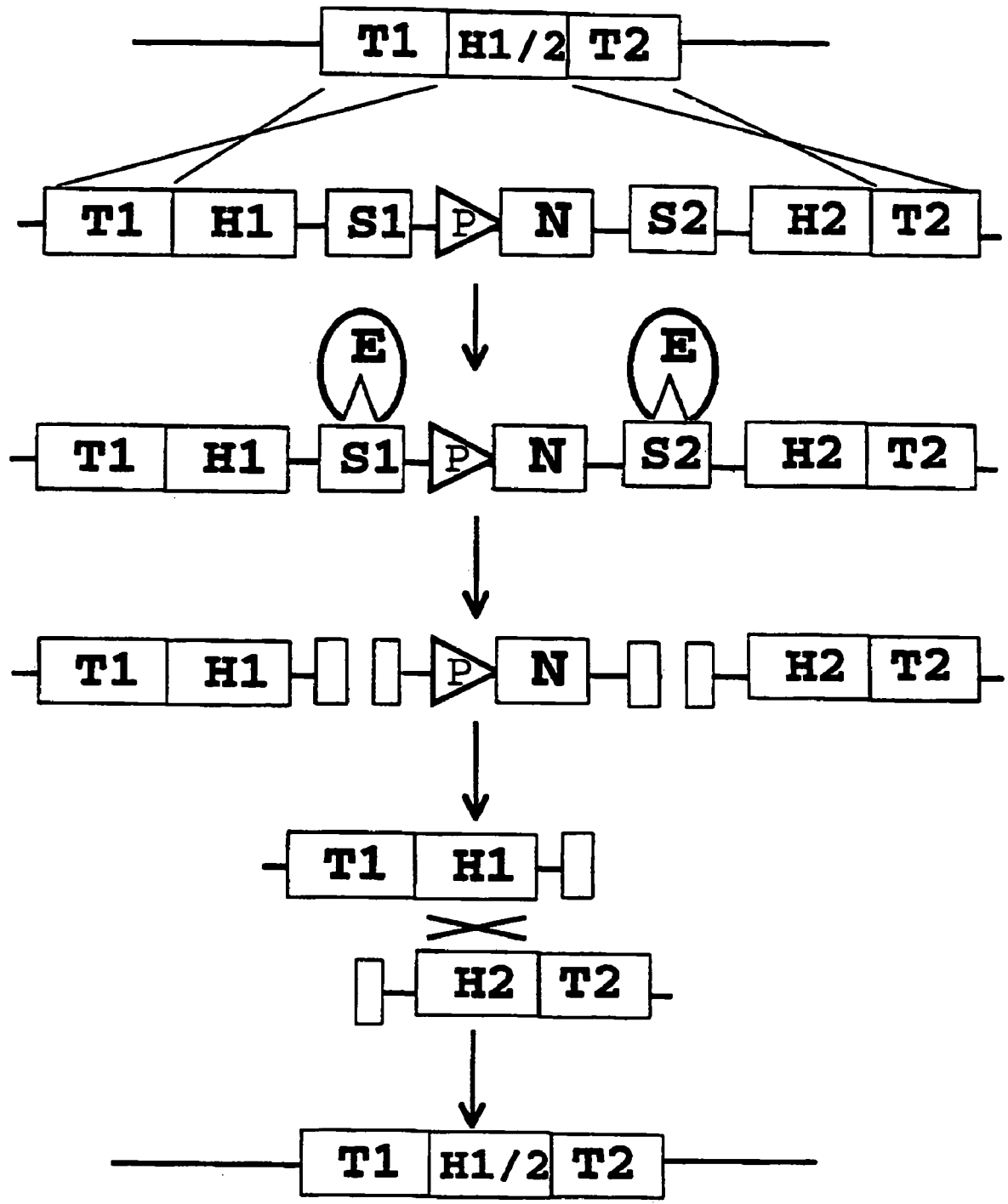
FIG. 4. Diagram of another preferred embodiment of the invention.

FIG. 4: Preferred embodiment. Sequences—in the present case for example an expression cassette consisting of a promotor (P) and a further nucleic acid sequence (N) to be expressed (for example a selection marker) can be eliminated virtually without trace from the chromosomal DNA when the recombination construct comprising them has previously been inserted into the host genome, for example by homologous recombination. In doing so, the gene consisting of the sequence segments T1, H1/2 and T2 is interrupted. The recombination construct is flanked by two parts of the interrupted gene (T1-H1 or H2-T2), the middle part (H1 or H2) having been duplicated in order to enable homologous recombination to take place. The action of the DSBI enzyme (E) on the cleavage sites (S1 and S2) induces double-strand breaks and induces the homologous recombination between the homology sequences H1 and H2, whereby firstly the sequences located between H1 and H2 are deleted and secondly the original gene is restored.

FIG. 5: Preferred embodiment. Nucleic acid sequences (in the present case a gene with the sequence T1-H1/2-T2 under the control of a promotor P) can be expressed inducibly by reconstituting the intact gene only by applying the recombination system. The gene, consisting of the sequence segments T1, H1/2 and T2 is inactivated, for example by the insertion of stop codons or other interruptions of the reading frame within the recombination construct. The recombination construct is flanked by two parts of the interrupted gene (T1-H1 or H2-T2), the middle part (H1 or H2) having been duplicated in order to enable homologous recombination to take place. The action of the DSBI enzyme (E) on the cleavage sites (S1 and S2) induces double-strand breaks and induces the homologous recombination between the homology sequences H1 and H2, whereby firstly the sequences located between H1 and H2 are deleted and secondly the intact gene is restored.

FIG. 6: Preferred embodiment. The figure shows a method which is identical to that described in FIG. 5, only that in the present case an endogenous gene is to be activated in a site-directed manner by introducing the recombination construct for example by means of homologous recombination.

FIG. 7a: Exemplary embodiment. The figure illustrates a specific embodiment of the method described in FIG. 6. A recombination construct is introduced via *agrobacterium*-mediated transfection. Flanked by the right and left border sequence (RB and LB, respectively), the construct comprises the interrupted reading frame of the GUS gene (β-glucuronidase) under the control of the 35S promotor (P) and the nopaline synthase (nos) terminator. The middle region of the GUS gene (U) was duplicated and constitutes the homology sequences A and B. Located between these sequences is the codA gene as negative selection marker under the control of the Cauliflower Mosaic Virus (CaMV) 35S promotor and the nopaline synthase (nos) terminator, flanked by two recognition sequences of the DSBI enzyme (S1 and S2). The recombination construct furthermore additionally comprises the BAR gene under the control of the 35S promotor (P) and the 35S terminator, as positive selection marker.

FIG. 7a illustrates the appearance of double-strand breaks and the homologous recombination between the homologous U sequences, brought about by the action of the DSBI enzyme, whereby firstly the sequences located between the homologous U sequences are deleted and secondly the GUS gene is restored. The length of the Acc65I fragment is thus reduced from 7.3 kb to 3.7 kb.

Figure 7B:
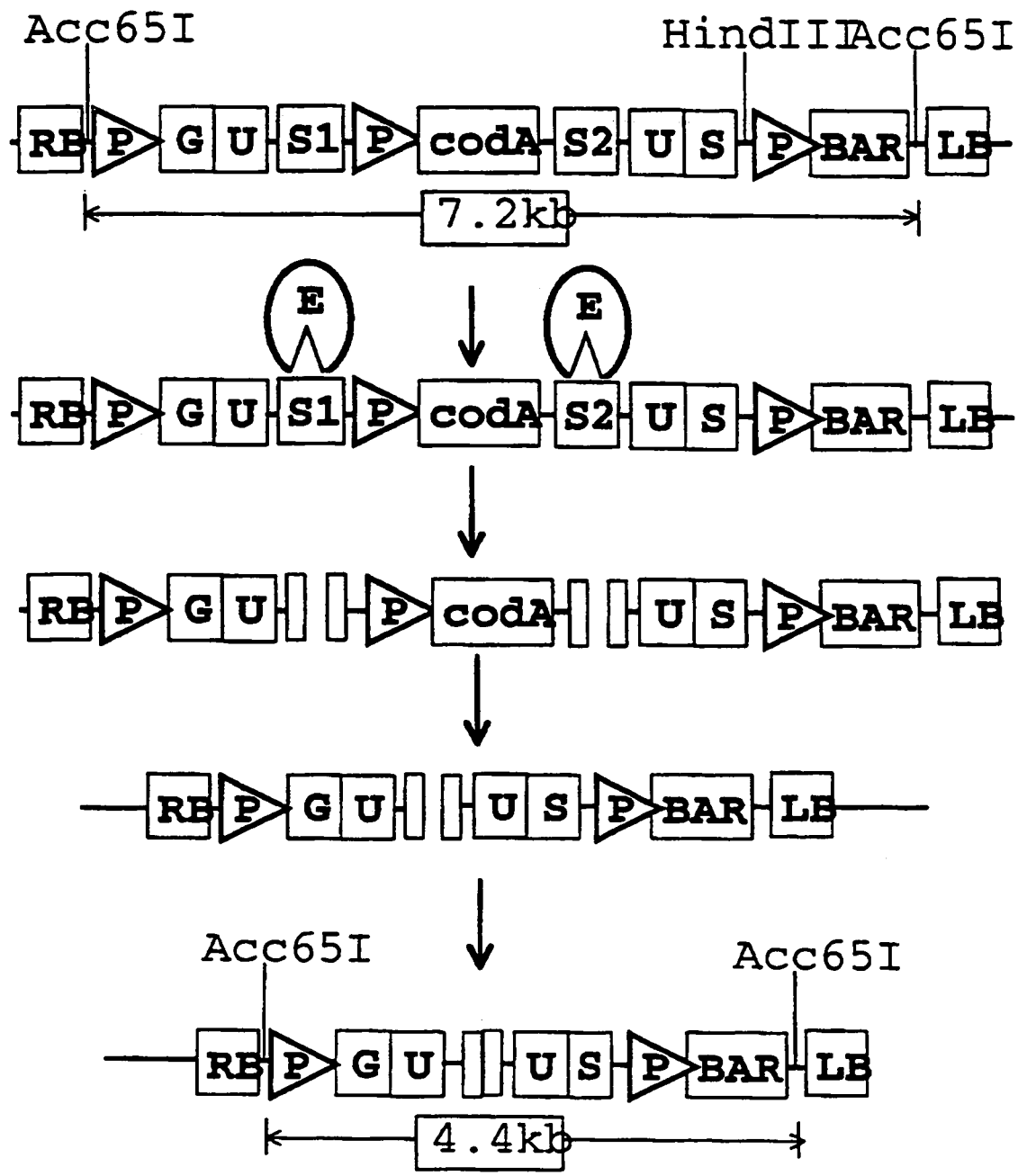
FIG. 7b shows the same system as described under FIG. 7a, however, in contrast, no homologous recombination takes place in the present case, but illegitimate recombination by non-homologous end-joining, whereby the region between S1 and S2 is deleted owing to the two cleavage sites and the GUS gene is not restored.

FIG. 7b: Shows the same system as described under FIG. 7a. FIG. 7a illustrates the appearance of double-strand breaks as the result of the action of the DSBI enzyme. In contrast to FIG. 7a, no homologous recombination takes place in the present case, but illegitimate recombination by non-homologous end-joining. While the region between S1 and S2 is deleted owing to the two cleavage sites, the GUS gene is not restored. The length of the Acc65I fragment is thus reduced from 7.3 kb to 4.4 kb.

Figure 7C:
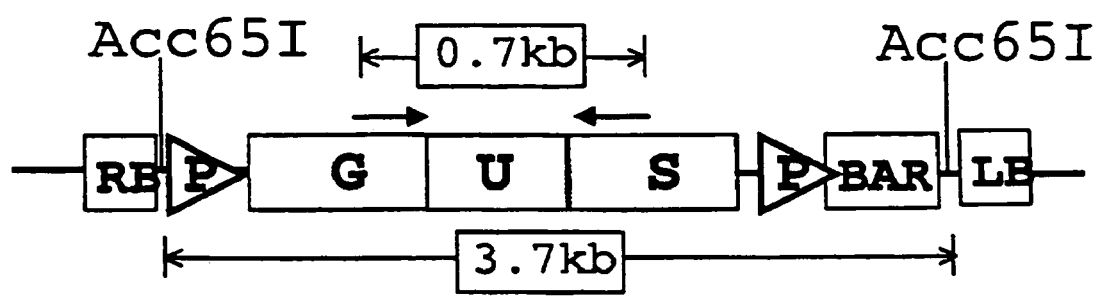
FIG. 7c illustrates another representation of the two end products of the processes described under FIGS. 7a and 7b. A is the result of the homologous recombination and B is the result of the illegitime recombination (non-homologous end-joining).
Figure 7C:
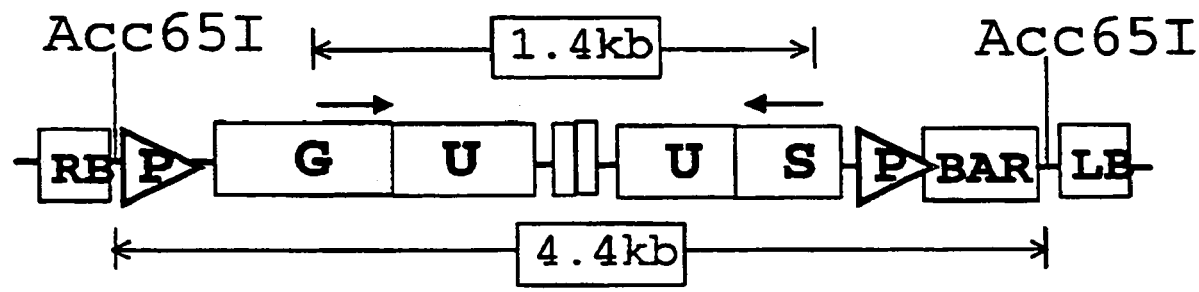

FIG. 7c: The figure is another representation of the two end products of the processes described under FIG. 7a and FIG. 7b. A: Result of the homologous recombination; Acc65I fragment has a length of 3.7 kb; the size of the fragment amplified with the aid of the primers OPN13 and OPN14 (shown by the arrows) is 0.7 kb. B: Result of the illegitimate recombination (non-homologous end-joining); Acc65I fragment has a length of 4.4 kb; the size of the fragment amplified with the aid of the primers OPN13 and OPN14 (shown by the arrows) is 1.4 kb.

FIG. 8: Preferred embodiment. The recombination cassettes advantageously encompass both a positive and a negative selection marker (PS and NS, respectively), in each case under the control of a promoter. The positive selection marker is useful for facilitating and detecting the introduction of the construct into the genome. The negative selection marker is useful for detecting the deletion of the construct from the genome. Both markers are eliminated efficiently from the chromosomal DNA when they are flanked by the homology sequences H1 and H2 and when in each case one cleavage site (S1 and S2, respectively) for a DSBI enzyme is located before and/or after the nucleic acid sequence to be deleted. Owing to the effect of the DSBI enzyme (E) on this recombination cassette, double-strand breaks appear at the cleavage sites S1 and/or S2 and the sequences located between H1 and H2 are then eliminated.

The effect of one of the abovementioned DSBI enzymes brings about site-directed double-strand breaks and induces the homologous recombination between the homologous U sequences, whereby firstly the sequences located between the homologous U sequences are deleted and secondly the GUS gene is restored.

Figure 9:
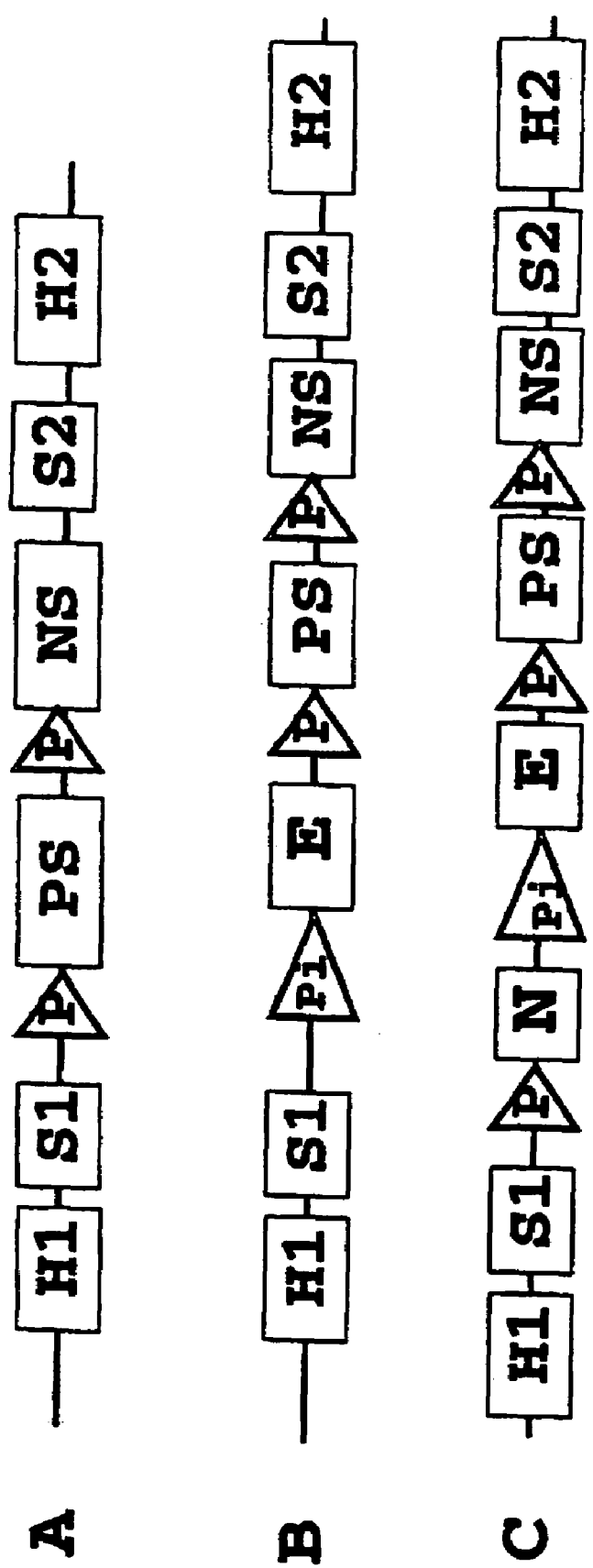
FIG. 9. Readily selectable systems for deleting nucleic acid sequences from chromosomal DNA of an organism.

FIG. 9: Readily selectable systems for deleting a nucleic acid sequence from the chromosomal DNA of an organism. The constructs comprise a positive selection marker (PS) and negative selection marker (NS), in each case under the control of a promoter (P).

(B) additionally comprises an expression cassette for the DSBI enzyme, expression preferably taking place under the control of an inducible promoter (Pi). (C) Further nucleic acid sequences may be present.

Expression of the DSBI enzyme leads in all cases to the elimination of the DNA sequences located between the two recognition sequences and to the recombination of the homologous sequences. Since the cells simultaneously lose a negative selection marker, the cells where successful deletion has taken place can be identified by means of selection (Gleave A P et al.(1999) Plant Mol Biol. 40:223-235).

Figure 10:
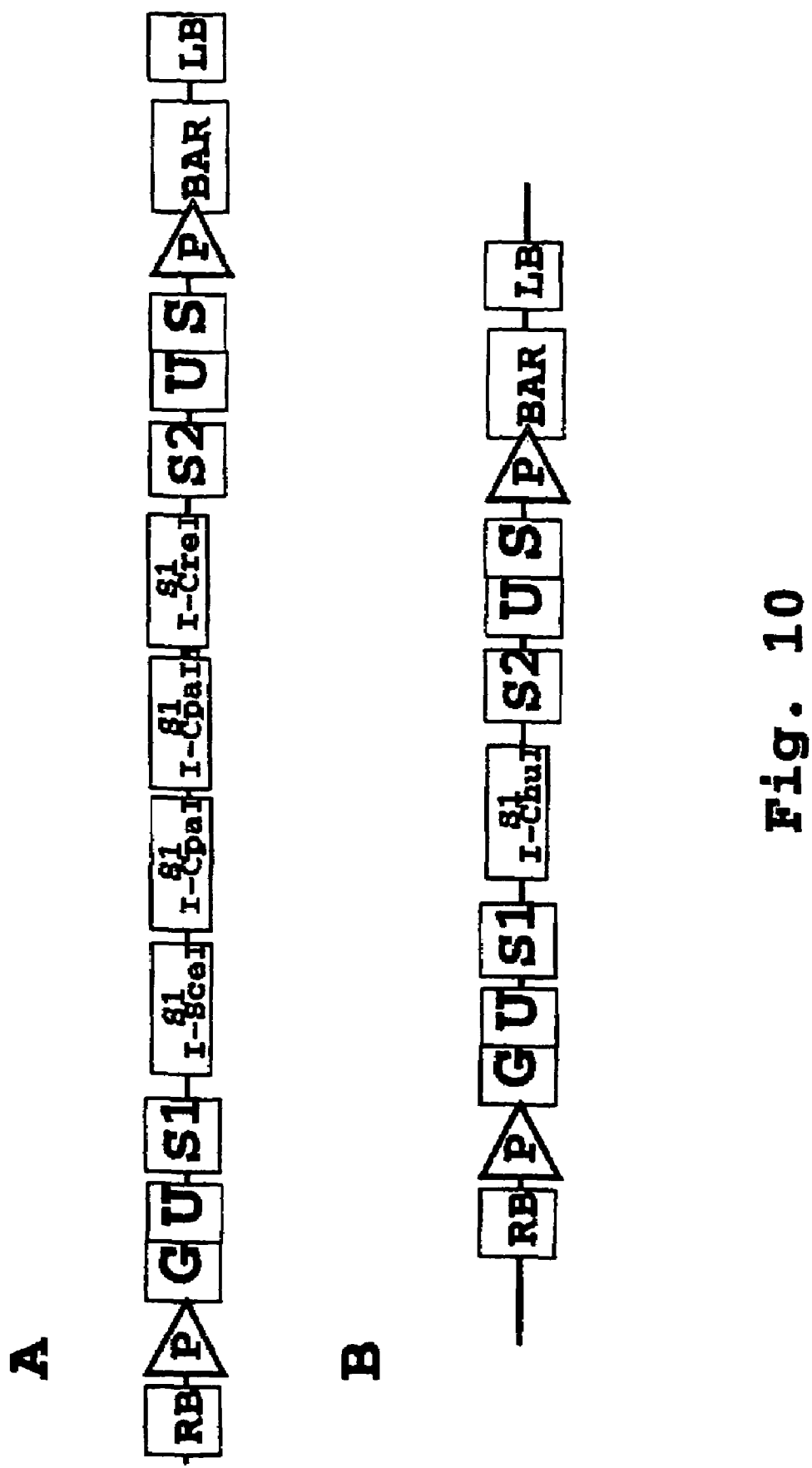
FIG. 10. Two constructs that demonstrate homologous recombination by double-strand breaks can be induced with restriction enzymes.

FIG. 10: The figure illustrates the two constructs (S1 construct (A) and SD construct (B)) which were used for proving that homologous recombination by double-strand breaks can be induced with different restriction enzymes. The constructs are introduced via *agrobacterium*-mediated transfection. The constructs, which are flanked by the right and left border sequence (RB and LB, respectively) contain the interrupted reading frame of the GUS gene (□-glucuronidase) under the control of the 35S promotor (P) and the nopaline synthase (nos) terminator. The middle region of the GUS gene (U) was duplicated and constitutes the homology sequences A and B. Located between these sequences are, in the case of the S1 construct (A), the recognition sequences of the DSBI enzymes I-SceI, I-CpaI, I-CpaII and I-CreI, and, in the case of the SD construct (B), the recognition sequence of the I-ChuI enzyme. The recombination constructs furthermore additionally contain the BAR gene under the control of a promotor (P) as positive selection marker.

Figure 11:
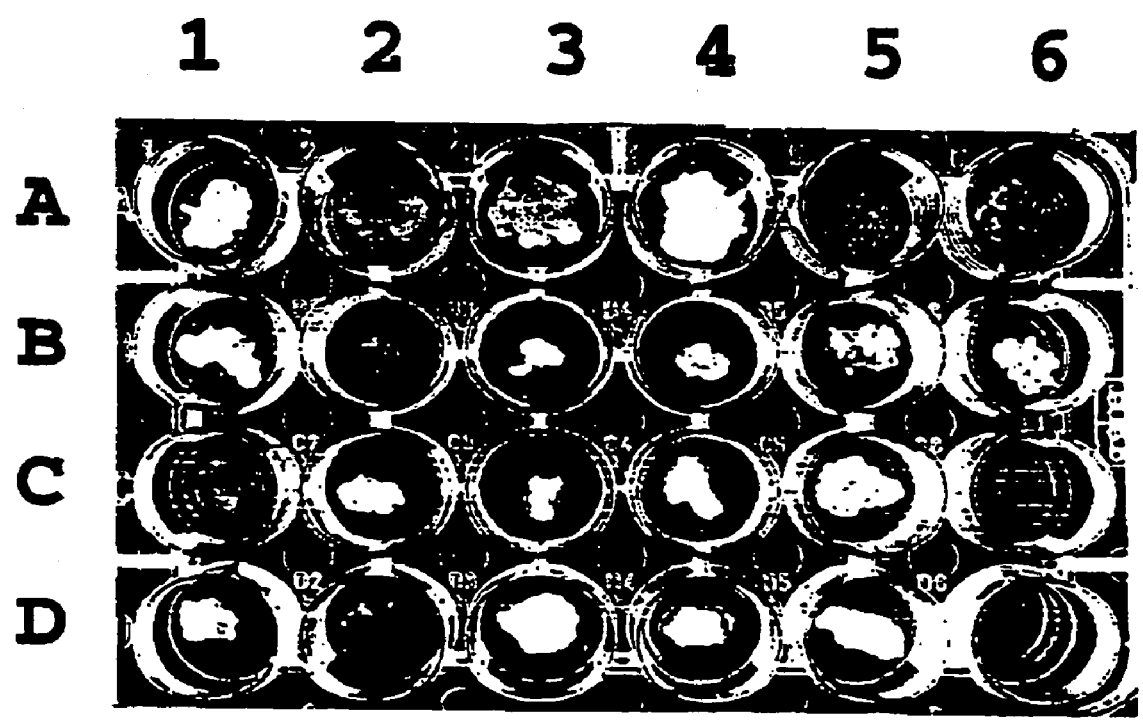
FIG. 11. Representative histochemical analysis of tobacco calli obtained after induction of double-strand breaks.

FIG. 11 Representative histochemical analysis of tobacco calli obtained after the induction of double-strand breaks. A blue coloration (here shown as dark coloration) indicates the expression of the β-glucuronidase gene, and thus the elimination of the selection marker by homologous recombination. Blue (dark colorations) can be seen in the case of the calli in the wells A2, A5, A6, B2, C1, C6 and D2.

Figure 12:
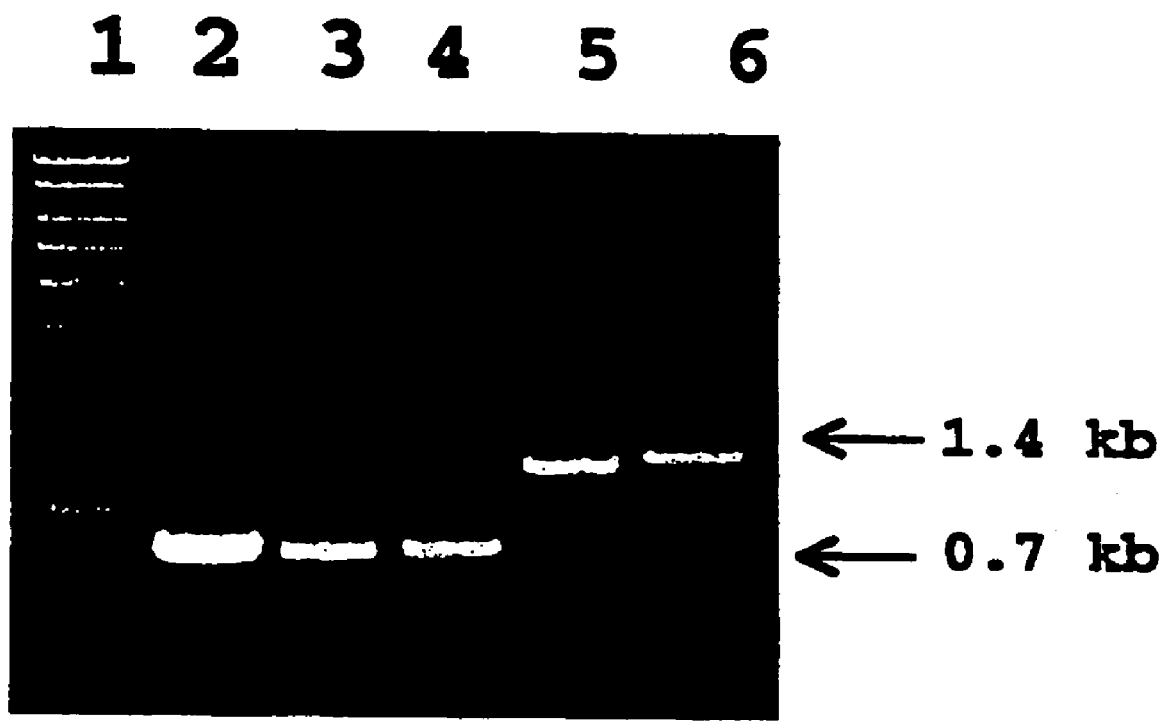
FIG. 12. PCR analysis for detecting homologous recombination.

FIG. 12: PCR analysis for detecting homologous recombination. PCR of DNA from tobacco calli using the primers OPN13 and OPN14. The PCR product (size 0.7 kb) which indicates homologous recombination can be seen in lanes 1, 2 and 3. The corresponding calli were blue following histochemical staining, and the corresponding PCR bands were sequenced in order to demonstrate that the open reading frame (ORF) of β-glucuronidase was indeed restored by homologous recombination. Lanes 4 and 5: PCR products (1.4 kb) of calli which did not turn blue upon staining, where the transgene was eliminated by non-homologous end-joining.

Figure 13:
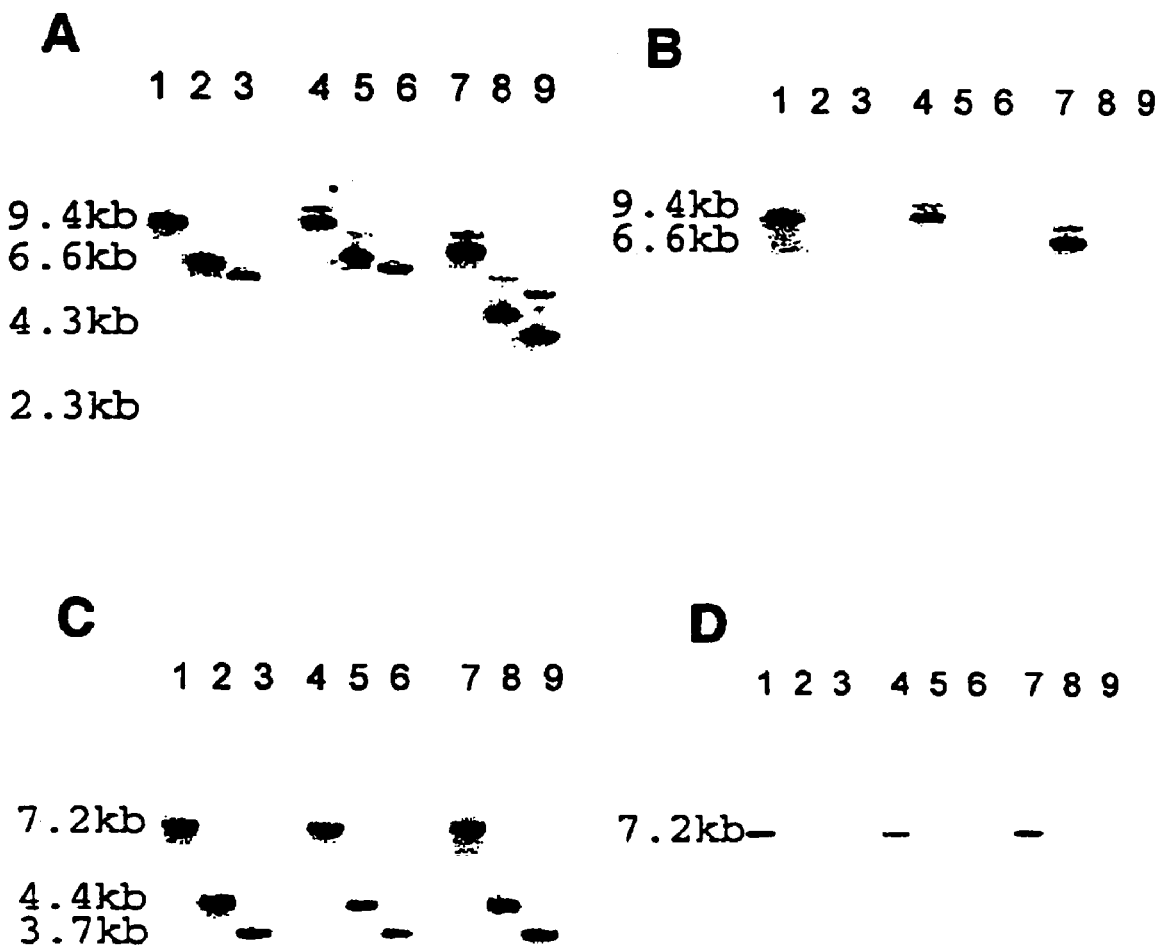
FIG. 13. Southern blots indicating complete elimination of a transgene sequence.

FIG. 13: Southern blots which indicate the complete elimination of the transgene sequence in question. The lanes of blots A to D comprise in each case:

| Lane | Line | Description |
|---|---|---|
| 1 | GU.C.USB 1 | Original line |
| 2 | GU.C.USB 1-61 | Non-homologous end-joining |
| 3 | GU.C.USB 1-83 | Homologous recombination |
| 4 | GU.C.USB 3 | Original line |
| 5 | GU.C.USB 3-1 | Non-homologous end-joining |
| 6 | GU.C.USB 3-3 | Homologous recombination |
| 7 | GU.C.USB 7 | Original line |
| 8 | GU.C.USB 7-14 | Non-homologous end-joining |
| 9 | GU.C.USB 7-34 | Homologous recombination |
| A: | | HindIII-digested DNA hybridized with a β-glucuronidase-specific probe. |
| B: | | HindIII-digested DNA hybridized with a codA-specific probe. |
| C: | | Acc65I-digested DNA hybridized with a β-glucuronidase-specific probe. |
| D: | | Acc65I-digested DNA hybridized with a codA-specific probe. |

The analysis demonstrates that, following the induction of DNA double-strand breaks by means of expression of the restriction enzyme, not only homologous recombination (lanes 3, 6 and 9), but also illegitimate recombination (lanes 2, 5 and 8) may occur, the transgene sequence (codA) located between the restriction cleavage sites always having been eliminated from the plant genome.

The following examples illustrate embodiments of the invention, but should not be viewed as limiting the scope of the invention.

EXAMPLES

General Methods:

The chemical synthesis of oligonucleotides can be affected for example in the known manner using the phosphoamidite method (Voet, Voet, 2nd edition, Wiley Press New York, pages 896-897). The cloning steps carried out for the purposes of the present invention, such as, for example, restriction cleavages, agarose gel electrophoresis, purification of DNA fragments, the transfer of nucleic acids to nitrocellulose and nylon membranes, the linkage of DNA fragments, the transformation of *E. coli* cells, bacterial cultures, the propagation of phages and the sequence analysis of recombinant DNA are carried out as described by Sambrook et al. (1989) Cold Spring Harbor Laboratory Press; ISBN 0-87969-309-6. Recombinant DNA molecules were sequenced using an ALF Express laser fluorescence DNA sequencer (Pharmacia, Upsala, Sweden) following the method of Sanger (Sanger et al., Proc. Natl. Acad. Sci. USA 74 (1977), 5463-5467).

Example 1

Cloning of the Homing Endonucleases

The open reading frames (ORFs) of the homing endonucleases I-CreI (Wang J et al. (1997) Nucleic Acids Res 25: 3767-3776), I-ChuI (Cote V et al.(1993) Gene 129:69-76), I-CpaI (Turmel M et al. (1995a) Nucleic Acids Res 23:2519-2525) and I-CpaII (Turmel M et al. (1995b) Mol. Biol. Evol. 12, 533-545) were cloned from the corresponding *Chlamydomonas* strains.

To ensure optimal translation of the gene, the ORFs of the endonucleases were linked to the leader sequence of a plant virus (CaMV gene V, as has proven useful in the case of I-SceI; Puchta H (1993) Nucl Acids Res 21:5034-5040). Also, a nuclear localization sequence (NLS2; SEQ ID NO: 30) was placed in front of the ORFs in order to efficiently transport the protein to the intended site of action. The two elements (leader sequence and nuclear localization sequence) were introduced via PCR by means of the oligonucleotide primers used.

To isolate the open reading frames (ORFs) of the endonucleases from *Chlamydomonas*, the algal cultures *Chlamy-*

*domonas reinhardtii*/Smith (strain no. 11-32b), *Chlamydomonas applanata*/Lucksch (strain no.: 11-9) and *Chlamydomonas segris*/King (strain no.: 9.83) were obtained from the algal culture collection at Göttingen (University of Göttingen, experimental phycology and collection of algal cultures, Albrecht-von-Haller Institute for Plant Sciences, Untere Karspüle 2, D-37073 Göttingen). The cultures were grown with the aid of a shake culture in MS medium, and DNA was obtained using the DNeasy Plant Maxi Kit (Qiagen, Hilden).

The I-CreI ORF (GenBank Acc. No.: X01977) was amplified from a sample of the algal culture 11-32b *Chlamydomonas reinhardtii*/Smith with the aid of the oligonucleotides OPN1 and OPN2 (SEQ ID NO: 11 and 12).

```
OPN1 (SEQ ID NO: 11):
5'-CGG CTC GAG CTA CGG GGA CGA TTT CTT TTT TTC
AC-3'

OPN2 (SEQ ID NO: 12):
5'-CGG CTC GAG TAC CTA GAA TAC AAA GAA GAG GAA GAA
GAA ACC TCT ACA GAA GAA GCC ATG GGT CCA AAG AAA
AAG AGA AAG GTT ATC AT GAA TAC AAA ATA TAA TAA AGA
GTT CTT ACT C 3'
```

2 ml (corresponding to approximately 100 ng DNA) of the DNA preparation were employed in the PCR reaction. The following were combined in a total volume of 50 ml in accordance with the manufacturer's instructions (Life Technologies):

5 ml 10× PCR buffer [200 mM Tris-HCl (pH 8.4), 500 mM KCl] 1.5 ml 50 mM MgCl$_2$ 1 ml 10 mM dNTP mix (10 mM of each dATP, dCTP, dGTP and dTTP) 1 ml primer OPN1 (10 mM) 1 ml primer OPN2 (10 mM) 0.4 ml Taq DNA polymerase (5 U/ml) 2 ml DNA preparation 38.1 ml autoclaved distilled water.

The reaction mixture is covered with approx. 50 ml of silicone oil and subjected to the following temperature program (Thermocycler: MWG Biotech Primus HT; MWG Biotech, Germany):

| | |
|---|---|
| 1 | cycle of 180 sec at 95° C. |
| 30 | cycles of 60 sec at 92° C., 60 sec at 54° C. and 3 min at 72° C. |
| 1 | cycle of 5 min at 72° C. |

The PCR fragment was purified via agarose gel electrophoresis using the QIAquickr Gel Extraction Kit (Qiagen, Hilden, Germany) and cloned into the pGEM-T Easy vector (Promega, Madison, USA). Next, a sequence analysis is carried out using the ALF-Express DNA sequencer (Pharmacia, Upsala, Sweden). The sequence is shown in SEQ ID NO: 5.

Cloning of the ORF of I-CpaI from the algal culture 9.83 *Chlamydomonas segris*/King (Genbank Acc. No.: L36830) was carried out analogously to the description given for I-CreI. The oligonucleotides OPN3 and OPN4 were used for the PCR. The sequence is shown in SEQ ID NO: 7.

```
OPN3 (SEQ ID NO: 13):
5'-CGG CTC GAG TAC CTA GAA TAC AAA GAA GAG GAA GAA
GAA ACC TCT ACA GAA GAA GCC ATG GGT CCA AAG AAA
AAG AGA AAG GTT ATC ATG GAC ATT AAT CCT CAA TGG
ATT ACA GG-3'

OPN4 (SEQ ID NO: 14):
5'-CGG CTC GAG TTA CTC GCC AGT TTC TTC AAA ACG-3'
```

Cloning the ORF of I-CpaII was also carried out analogously as described for I-CreI (Genbank Acc. No: L39865). A sample of the algal culture 9.83 *Chlamydomonas segris*/King was used for this purpose. The oligonucleotides OPN5 and OPN6 were used for the PCR. The sequence is shown in SEQ ID NO: 9.

```
OPN5 (SEQ ID NO: 15):
5'-CGG CTC GAG TAC CTA GAA TAC AAA GAA GAG GAA GAA
GAA ACC TCT ACA GAA GAA GCC ATG GGT CCA AAG AAA
AAG AGA AAG GTT ATC ATG ACC GAT TCT AAA TCT AGA
AAC AAC-3'

OPN6 (SEQ ID NO: 16):
5'-CGG CTC GAG CTA AAG GTG GCC TTT ATT GCC ATC
AG-3'
```

Cloning of the ORF of I-ChuI from the algal culture 11-9 *Chlamydomonas applanata*/Lucksch (Genbank Acc. No.: L06107) was carried out analogously to the description given for I-CreI. The oligonucleotides OPN7 and OPN8 were used for the PCR. The sequence is shown in SEQ ID NO: 3.

```
OPN7 (SEQ ID NO: 17):
5'-CGG CTC GAG TAC CTA GAA TAC AAA GAA GAG GAA GAA
GAA ACC TCT ACA GAA GAA GCC ATG GGT CCA AAG AAA
AAG AGA AAG GTT ATC ATG TCA TTA ACA CAA CAA CAA
AAA GAC-3'

OPN8 (SEQ ID NO: 18):
5'-CGG CTC GAG CTA AAG GTG GCC TTT ATT GCC ATC
AG-3')
```

The ORF of the individual homing endonucleases (with the nuclear localization signal) was in each case excised from the pGEM-T Easy vector by means of restriction digestion with SalI, purified by gel electrophoresis and in each case cloned into the SalI restriction cleavage site of the binary vector pBinAR (Höfgen and Willmitzer (1990) Plant Science 66:221-230). Expression of the individual enzymes takes place under the control of the 35S promotor and the octopine synthase terminator.

The binary I-SceI expression vector pCISceI (Puchta H et al. (1996) Proc. Natl. Acad. Sci. USA 93:5055-5060) contains a synthetic I-SceI ORF under the control of the CaMV 35S promotor (Puchta H et al. (1993) Nucl Acids Res 21: 5034-5040) between the T-DNA borders.

All of the five plasmids were multiplied in *E. coli*, purified by means of the QIAfilter Plasmid Midi kit (Qiagen, Hilden) and transferred into the agrobacterial strain C58 by means of electroporation.

Example 2

Generation of the Construct pGU.I.USB

The plasmid pGU.US (Tinland B et al. (1994) Proc. Natl. Acad. Sci. USA 91:8000-8004) was used for constructing the recombination substrates. Within the T-DNA region, the plasmid contain two overlapping halves of the β-glucuronidase (GUS) gene with a 557 bp overlap. A hygromycin gene is integrated in a unique XbaI cleavage site between the GUS sequences.

In a first step, the BAR gene together with promotor and terminator sequences was excised from the vector pRC (Puchta H et al. (1996) Proc Natl Acad Sci USA 93:5055-5060) in the form of an isolated HindIII fragment, separated from the vector sequence via agarose gel electrophoresis, excised from the gel, isolated with the aid of the QIAquickr Gel Extraction Kit (Qiagen, Hilden, Germany) and thereafter inserted into the unique HindIII cleavage site of pGU.US. To this end, the vector pGU.US was previously cut with HindIII and dephosphorylated with alkaline phosphatase (calf intestinal alkaline phosphatase (CIP), New England Biolabs, Frankfurt, Germany) in order to prevent recircularization. The resulting vector is termed pGU.US-BAR.

In the vector pNE3 (Stougaard J (1993) Plant J 3:755-761), the XbaI cleavage site was first removed by a Klenow filling-in reaction. The open reading frame (ORF) of the negative selection marker gene cytosine deaminase (codA) under the control of the Cauliflower Mosaic Virus (CaMV) 35S promotor and of the nopaline synthase (nos) terminator was amplified from the resulting vector pNE3-XBA by means of PCR using the oligonucleotide primers ONP9 (SEQ ID NO: 16) and ONP10 (SEQ ID NO: 17). Owing to the oligonucleotide primers OPN9 and OPN10 used, in each case one I-SceI cleavage site (emphasized in bold in the sequences stated herein) and a NotI or XbaI cleavage site were added to the two ends of the amplificate.

```
OPN9 (SEQ ID NO: 19):
5'-CGG CTC TAG AGC GGC CGC CTA GGG ATA ACA GGG TAA
TAG AAT CCC ACA AAA ATC TGA GCT AAA CAG 3'

OPN10 (SEQ ID NO: 20):
5'-CGG CTC TAG ACT ATT ACC CTG TTA TCC CTA GGC CCG
ATC TAG TAA CAT AGA TGA CAC CGC GCG CG 3'
```

2 ml (corresponding to approximately 100 ng) of a plasmid preparation of pNE3-XBA were employed for the PCR reaction. The following were combined in a total volume of 50 ml in accordance with the manufacturer's instructions (Life Technologies):

5 ml 10× PCR buffer [200 mM Tris-HCl (pH 8.4), 500 mM KCl] 1.5 ml 50 mM $MgCl_2$ 1 ml 10 mM dNTP mix (10 mM of each dATP, dCTP, dGTP and dTTP) 1 ml primer OPN1 (10 mM) 1 ml primer OPN2 (10 mM) 0.4 ml Taq DNA polymerase (5 U/ml) 2 ml plasmid preparation of pNE3-XBA 38.1 ml autoclaved distilled water.

The reaction mixture is covered with approx. 50 ml of silicone oil and subjected to the following temperature program (Thermocycler: MWG Biotech Primus HT; MWG Biotech, Germany):

| 1 | cycle of 180 sec at 95° C. |
| 30 | cycles of 60 sec at 92° C., 60 sec at 54° C. and 3 min at 72° C. |
| 1 | cycle of 5 min at 72° C. |

The PCR product was digested with XbaI and NotI. The vector pGU-US-BAR was likewise digested with XbaI and NotI (which resulted in the deletion of the hygromycin marker gene), and the vector fragment was purified by agarose gel electrophoresis using the QIAquickr Gel Extraction Kit (Qiagen, Hilden, Germany). Ligation of the digested PCR fragment and vector gave rise to the binary vector pGU.C.USB (see FIG. 7a). The vector contains a marker gene (cytosine deaminase (codA)) on a T-DNA between two I-SceI cleavage sites. The I-SceI cleavage sites are outwardly flanked by homologous sequence regions 557 bp in size of the β-glucuronidase gene (GUS). The GUS gene acts as homologous restoration marker (Swoboda P et al. (1994) EMBO J 13:481-489). If the gene is restored by homologous recombination, the expression can be detected histochemically. Elimination of the marker gene gives rise to 5-FC (fluorocytosine)-resistant tobacco cells, which can then regenerate it to give calli (Salomon S and Puchta H (1998) EMBO J 17:6086-6095).

Example 3

Plant Transformation with pGU.I.USB

*Nicotiana tabacum* L. cv. Petite Havana Line SR1 seedlings were transformed with the agrobacterial strain C58, which contained the binary vector pGU.C.USB.

To this end, seeds were placed on moistened filter paper under sterile conditions and the seedlings were harvested after 2 weeks, all as described by Puchta H. (1999) Methods Mol Biol 113: 447-451 (25° C., 16 hours light/8 hours dark rhythm).

For the inoculation, the agrobacteral strain containing the binary transformation plasmid was first grown overnight in a shake culture at 28° C. in YEB medium. Then, the agrobacterial suspension was centrifuged for 10 minutes at 15.000 g and the cells were taken up in 10 mM $MgSO_4$ so that the final optical density of the suspension had a value of approximately 0.5. In a reaction vessel, the seedlings were then placed into the bacterial solution under sterile conditions and a vacuum of 0.15 at was applied in a sterile desiccator. After 10 minutes, the seedlings were then placed on MS plates supplemented with BAP (6-benzylaminopurine 5 mg/ml) and NAA (1-naphthaleneaceteic acid 0.5 mg/ml) and left for 3 days in a growth cabinet (25° C., 16 hours light/8 hours dark rhythm). The seedlings were then placed on MS medium supplemented additionally with phosphinothricin (100 mg/ml), vancomycin (1 mg/ml) and cefotaxim (0.5 mg/ml) in addition to NAA and BAP. Every 10 days, the seedlings were transferred to freshly made plates. Eventually, the resulting calli formed shoots. As soon as the shoots had attained a certain size (1 to 2 cm), they were excised from the callus material and planted in magenta boxes comprising MS medium supplemented with phosphinothricin, vancomycin and cefotaxin (concentrations as above). After a short time, the shoots developed roots; they were transferred into soil after 2 to 4 weeks. The plants were made to flower in the greenhouse and were then shelled, and the seeds formed were left to ripen in the capsules. The seeds were then placed on MS medium supplemented with 300 mg of phosphinothricin (for the positive selection) or 500 mg of 5-FC (fluorocytosin; for the negative selection) per ml in order to carry out the segregation analyses. By determining the ratio of resistant to sensitive seedlings (3:1 in the case of positive selection and 1:3 in the case of negative selection), it was possible to demonstrate that the recombination constructs were inserted at a locus in the three selected lines.

Example 5

Induction of Gene Deletion by Introducing the DSBI Enzyme I-SceI

In the experiments, F1 seedlings of the transgenic lines GU.C.USB 1, 3 and 7, each of which comprises a copy of the T-DNA GU.C.USB shown in FIG. 2, were inoculated with an agrobacterial strain which transiently expressed I-SceI and which comprised the plasmid pCISceI (Puchta H et al. (1996) Proc Natl Acad Sci USA 93, 5055-5060) in the above described manner (see also Puchta, 1999b). After 3 days, the seedlings were plated on MS medium supplemented with BAP and NAA (concentrations as above) medium to the same medium additionally in the presence of 100 mg of 5-FC and 100 mg of phosphinothricin per ml incubated in order to detect plant cells in which the marker gene to be eliminated (in this case the codA gene) was deleted. After 6 weeks, the calli growing on the medium were divided into two, and one part was used for the regeneration of shoot axes while the other was used for isolating DNA and for the β-glucuronidase assay. The resulting 5-FC-resistant transgenic calli were analyzed for homologous recombination events by means of histochemical staining. A blue staining indicated restoration of the callus (see FIG. 11).

The histochemical staining of the calli was carried out as described by Swoboda et al., 1994. To this end, the calli were introduced into staining solution (0.3 mg X-Gluc [Duchefa, Harlem, Nl] per ml of 100 mM sodium phosphate buffer pH 7.0; 0.1% Triton; 0.05% $NaN_3$). A vacuum was applied for 15 minutes to the desiccator, and the calli were subsequently incubated in the solution for 48 hours at 37° C. After the staining solution was poured off, the remaining chlorophyll was removed from the plant material by repeated shaking in 80% ethanol. The blue staining obtained indicated the β-glucuronidase activity.

In approximately one quarter of the cases, the marker gene was eliminated successfully by homologous recombination (FIG. 11, Table 2).

TABLE 2

Number of 5-FC-resistant tobacco calli following transient DSB induction

| Transgenic line | Seedlings | resistant calli | GUS-positive | GUS-positive (% of resistant calli) |
|---|---|---|---|---|
| GU.C.USB 1 | 290 | 56 | 22 | 39 |
| GU.C.USB 3 | 490 | 90 | 24 | 27 |
| GU.C.USB 7 | 370 | 59 | 11 | 19 |

Molecular analyses confirm the facts: since the line GU.C.USB 1 contained a single copy of the transgene, the calli were analyzed directly for recombination results by means of PCR.

A random fraction of calli was then analyzed at the molecular level by means of PCR. Molecular analysis with the primer pairs OPN11 (SEQ ID NO: 21)
5'-CGG AAG CTT CGT CAC CAA TCC CAA TTC GAT CTA C-3'
and

OPN12 (SEQ ID NO: 22)
5'-CGG AAG CTT CCA CTT GCA AAG TCC CGC TAG TGC C-3' allowed the isolation of the newly-formed linkage sites from the tobacco genome (FIG. 12; Table 3).

TABLE 3

Molecular analysis of recombination events by means of PCR

| Transgenic line | Calli | PCR fragment(s) | | |
|---|---|---|---|---|
| | | 0.7 kb | 1.4 kb | none/other |
| GU.C.USB 1 | 30 | 10 | 12 | 7 |

Three 0.7 kb PCR fragments were selected and sequenced. In all three cases, sequencing confirmed the functional sequence of the β-glucuronidase gene, i.e. the restoration of the gene did indeed take place accurately by homologous recombination.

When five 1.4 kb PCR bands were sequenced, it was found that these bands were formed after excision of the codA gene by reparation of the two I-SceI cleavage sites (by non-homologous end-joining, NHEJ) without homologous recombination taking place. In most cases, minor deletions at the I-SceI cleavage site resulted.

Southern blots demonstrated that, as expected, complete elimination of the sequence located between the I-SceI cleavage sites took place in the recombinants with the 0.7 and 1.4 kb bands, respectively. No codA-specific DNA whatsoever was detectable any longer in the genome of the regenerated plants (FIG. 13B and D, lanes 2 and 3).

The DNA was isolated with the aid of the DNeasy Plant Mini Kit (Quiagen, Hilden). To detect the recombination products, genomic DNA was analyzed by means of PCR using the oligonucleotides OPN13 and OPN14.

OPN13 (SEQ ID NO: 23):
5'-CGG AAG CTT CGT CAC CAA TCC CAA TTC GAT CTA C-3'

OPN14 (SEQ ID NO: 24):
5'-CGG AAG CTT CCA CTT GCA AAG TCC CGC TAG TGC C-3'

5 ml 10× PCR buffer [200 mM Tris-HCl (pH 8.4), 500 mM KCl] 1.5 ml 50 mM $MgCl_2$ 1 ml 10 mM dNTP mix (10 mM of each dATP, dCTP, dGTP and dTTP) 1 ml primer OPN1 (10 mM) 1 ml primer OPN2 (10 mM) 0.4 ml Taq DNA polymerase (5 U/ml) 2 ml DNA preparation 38.1 ml autoclaved distilled water.

The reaction mixture is covered with approx. 50 ml of silicone oil and subjected to the following temperature program (Thermocycler: MWG Biotech Primus HT; MWG Biotech, Germany):

| | |
|---|---|
| 1 | cycle of 180 sec at 95° C. |
| 30 | cycles of 60 sec at 92° C., 60 sec at 54° C. and 3 min at 72° C. |
| 1 | cycle of 5 min at 72° C. |

The PCR products were sequenced using the "ABI Prism Dye Terminator Cycle Sequencing Reaction Kit" (PE Applied Biosystems, Weiterstadt).

For the Southern blotting, the DNA was cut with HindIII or Acc65I and subjected to electrophoresis in a 0.8% agarose gel. The DNA in the gel was then transferred to the hybridization membrane 'Hybond N' (Amersham, Little Chalfont, UK) by means of capillary blotting as described in the manufacturer's instructions. For the molecular hybridization, codA- or GUS-specific gene fragments were isolated from the starting plasmids (XbaI/XhoI fragment as PNE3; Stougaard, 1993, and KpnI/SacI fragment from pGUS23, Puchta and Hohn, 1991, isolated using the QIAquick Gel Extraction Kit [Qiagen, Hilden]) and labeled with the aid of a "Random Priming Labeling Kit" (Megaprime DNA labeling system RPN1607, Amersham, Little Chalfont, UK) and [$\square$-$^{32}$P]dATP (Amersham, Little Chalfont, UK). The hybridization reactions were carried out at 65° C.

Since in each case 2 genetically linked transgene copies were integrated in the case of lines GU.C.USB 3 and GU.C.USB 7, a representative number of plants was regenerated from callus in the case of these lines, DNA was obtained and then analyzed per Southern blot (Table 4).

In the case of Acc65I, the presence of a GUS-specific 3.7 kb band suggests a homologous recombination, while a 4.4 kb band suggests an NHEJ event ("non-homologous end-joining"; NHEJ) (FIG. 7b and c; FIG. 13C).

TABLE 4

Molecular analysis of recombination events by means of Southern blots

| Transgenic line | Calli | Acc65I fragment (kb) | | |
|---|---|---|---|---|
| | | 3.7 | 4.4 | Deletion |
| GU.C.USB 3 | 39 | 6 | 18 | 15 |
| GU.C.USB 7 | 14 | 2 | 5 | 7 |

Interestingly, the same type of linkage in the two transgene copies was found in all cases. In other words, either only homologous recombinations or only NHEJ events occurred. In no case did both possibilities exist in parallel, i.e. for example a homologous recombination in the one transgene and an NHEJ event in the other.

In both lines, PCR analyses were also carried out, and in each case three 0.7 kb PCR fragments were selected and sequenced. In all three cases, sequencing revealed the functional sequence of the β-glucuronidase gene, i.e. the restoration of the gene did indeed occur by means of homologous recombination.

When a total of nine 1.4 kb PCR bands of the two lines were sequenced, it was furthermore found that these bands indeed originated after excision of the codA gene by repair of the two I-SceI cleavage sites (by "non-homologous end-joining" NHEJ). Again, minor deletions resulted at the I-SceI cleavage site in most cases.

Southern blots demonstrated that, as expected, the sequence between the I-SceI cleavage sites were eliminated completely in the recombinant. No codA-specific DNA whatsoever was detected any longer in the genome of the regenerated plants (FIG. 13B and D, lanes 5, 6 and 8,9).

Example 5

Various transgenic tobacco plant lines were generated which, between the halves of the β-glucuronidase gene (arrangement as described above) also contained cleavage sites for the abovementioned restriction enzymes in addition to a I-SceI cleavage site by means of cloning synthetic oligonucleotides (FIG. 10). Seedlings of this tobacco line were inoculated in each case in direct comparison with agrobacteria capable of expressing either I-SceI or the corresponding enzyme in plant cells. The resulting calli were then stained histochemically after 2 weeks. The results are shown in Table 4.

The plasmid pGU.C.US.B was cut with I-SceI so that the codA gene was excised from the plasmid. The digested DNA was separated by means of agarose gel electrophoresis, the larger band was excised and purified by means of the QIAquick Gel Extraction Kit (Qiagen, Hilden) and subsequently ligated and transformed into E. coli. The resulting plasmid was then cut with XbaI.

The complementary single-stranded oligonucleotides OPN25 and OPN26 were made double-stranded by briefly heating to 92° C. and subsequent cooling and then subsequently ligated with the XbaI-cut plasmid. The resulting SI construct (pSI) contains the cleavage sites for I-SceI, I-CpaI, I-CpaII and I-CreI ((see FIG. 10(A)).

OPN15 (SEQ ID NO: 25):
5'-CTA GTA CAA AAC GTC GTG AGA CAT TTT AAT CTG AAG
GTT TGG CAC CTC GAT GTC GGC TCA TC-3'

OPN16 (SEQ ID NO: 26):
5'-CTA GGA TGA GCC GTC ATC GAG GTG CCA AAC CTT CAG
ATT AAA ATG TCT CAC GAC GTT TTG TA-3'

The complementary single-stranded oligonucleotides OPN27 and OPN28 were made double-stranded by briefly heating to 92° C. and subsequent cooling and then subsequently ligated with the XbaI-cut plasmid. The resulting SD construct (pSD) contains the cleavage sites for I-SceI and I-ChuI (see FIG. 10(B)).

OPN17 (SEQ ID NO: 27):
5'-CTA GTC CGA AAA CGC CGT GAG ACA TAT TGG TTA CGA
TCC TAA GGT AGC GAA ATT CAC CCG GTA ACT CTG TGC
CAG-3'

OPN18 (SEQ ID NO: 28):
5'-CTA GCT GGC ACA GAG TTA CCG GGT GAA TTT CGC TAC
CTT AGG ATC GTA ACC AAT ATG TCT CAC GGC GTT TTC
GGA-3'

Transgenic tobacco plants with the two constructs were generated as described further above by means of agrobacterium transformation. Lines which only contained transgenic sequences at one locus were used for the further experiments. These lines were determined by the 3:1 segregation into phosphinothricin-resistant and nonresistant plants. The shelled seedlings were then inoculated with agrobacterial strains which comprised one of the four constructs for expressing the restriction endonucleases or, as the vector control, the plasmid BinAR or, as the positive control, a 1:1 mixture of BinAR and CISce-I. The inoculations were carried out as described above (Puchta H (1999) Methods Mol. Biol. 113:447-451), and for selection purposes the seedlings were grown over several weeks on MS medium supplemented with 100 μg kanamycin per ml, which also contained BAP and NAA, vancomycin and cefotaxin (concentrations as above). The resulting calli were then subjected to histochemical β-glucuronidase staining as described above.

All four of the tested restriction enzymes were capable of inducing homologous recombination in the same order of magnitude as I-SceI (which was employed here in a co inoculation with the selection vector pBinAR [AR]) (Table 5). This demonstrates that homologous recombination can be induced efficiently when using any restriction endonucleases.

TABLE 5

Induction of homologous recombination in plants by means of various endonucleases I-CreI, I-CpaI, I-CpaII and I-ChuI. [Sectors/calli] refers to the number of areas stained blue in the resistant calli.

| Transgenic line | Enzyme | Sectors/calli | Ratio |
|---|---|---|---|
| SI5 | I-SceI/AR | 42/31 | 1.35 |
| | I-CreI | 77/50 | 0.54 |
| | I-CpaII | 51/50 | 1.02 |
| SI2 | I-SceI/AR | 8/9 | 0.89 |
| | I-CreI | 40/18 | 2.22 |
| | I-CpaII | 9/20 | 0.45 |
| SI2 | I-CpaI | 144/106 | 1.36 |
| SD2 | I-ChuI | 166/100 | 1.66 |

Other embodiments and uses of the invention will be apparent to those skilled in the art from consideration of the specification and practice of the invention disclosed herein. All references cited herein, including all U.S. and foreign patents and patent applications, and all publications or other documentary materials, are specifically and entirely hereby incorporated herein by reference. It is intended that the specification and examples be considered exemplary only, with the true scope and spirit of the invention indicated by the following claims.

The invention claimed is:

1. A recombination system comprising:
a transgenic recombination construct capable of being inserted into the chromosomal DNA of a eukaryotic organism said construct comprising in a 5'- to 3'-orientation;
a first homology sequence A;
at least one recognition sequence for site-directed induction of DNA double-strand breaks; and
a second homology sequence B,
where all recognition sequences for site-directed induction of DNA double-strand breaks are located between homology sequences A and B;
wherein the homology sequences A and B have at least 20 base pairs and at least 70% homology that allows for homologous recombination to each other; and
an enzyme suitable for inducing DNA double-strand breaks at a recognition sequence for the site-directed induction of DNA double-strand breaks or a nucleic acid sequence encoding said enzyme;
wherein after homologous recombination of homology sequences A and B the resulting transgenic sequence derived from said transgenic recombination construct does not comprise any recognition site for said enzyme suitable for inducing DNA double-strand breaks.

2. The system of claim 1, wherein the construct, after said first homology sequence, contains a further nucleic acid sequence.

3. The system of claim 2, wherein the construct further contains a second recognition sequence for the site-directed induction of DNA double-strand breaks.

4. The system of claim 2, wherein the further nucleic acid sequence contains at least one selection marker.

5. The system of claim 1, wherein the construct further contains at least one of the elements selected from the group consisting of selection markers, reporter genes, replication origins, multiple cloning regions, border sequences for *Agrobacterium transfection*, sequences which enable homologous recombination or insertion into a genome of a host organism, expression cassette for an enzyme suitable for inducing DNA double-strand breaks at the recognition sequence for the site-directed induction of DNA double-strand breaks and combinations thereof.

6. The system of claim 1, wherein the enzyme is selected from the group consisting of restriction endonucleases, homing endonucleases, group II intron endonucleases, recombinases, transposases, chimeric nucleases and combinations thereof.

7. The system of claim 1, wherein the enzyme is selected from the group consisting of F-SceI, F-SceII, F-SuvI, F-TevI, F-TevII, I-AmaI, I-AniI, I-CeuI, I-CeuAIIP, I,-ChuI, I-CmoeI, I-CpaI, I-CpaII, I-CreI, I-CrepsbIP, I-CrepsbIIP, I-CrepsbIIIP, I-CrepsbIVP, I-CsmI, I-CvuI, I-CvuAIP, I-DdiI, I-DdiII, I-DirI, I-DmoI, I-HmuI, I-HmuII, I-HspNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PpbIP, I-PpoI, I-SPBetaIP, I-ScaI, I-SceI, I-ScelI, I-SceIII, I-SceIV, I-SceV, I-SceVI, I-SceVII, I-SexIP, I-SneIP, I-SpomCP, I-SpomIP, I-SpomIIP, I-SquIP, I-Ssp6803I, I-SthPhiJP, I-SthPhiST3P, I-SthPhiS3bP, I-TdeIP, I-TevI, I-TevII, I-TevIII, I-UarAP, I-UarHGPA1P, I-UarHGPA13P, I-VinIP, I-ZbiIP, PI-MtuI, PI-MtuHIP, PI-MtuHIIP, PI-PfuI, PI-PfuII, PI-PkoI, PI-PkoII, PI-PspI, PI-Rma43812IP, PI-SPBetaIP, PI-SceI, PI-TfuI, PI-TfuII, PI-ThyI, PI-TLiI, PI-TliII and combinations thereof.

8. The system of claim 1, wherein the enzyme is selected from the group consisting of enzymes comprising the sequence as shown in SEQ ID NO: 2, 4, 6, 8 or 10, and combinations thereof.

9. The system of claim 1, wherein the enzyme is expressed from an expression cassette that contains a nucleic acid sequence encoding said enzyme.

10. The system of claim 9, wherein the nucleic acid sequence comprises the sequence as shown in SEQ ID NO: 1, 3, 5, 7 or 9.

11. A method for removing a DNA sequence from chromosomal DNA of a eukaryotic cell or organism comprising:
introducing the recombination system of claim 1 into the chromosomal DNA of a eukaryotic cell or organism;
inducing DNA double-strand breaks at the recognition sequence; and
conducting homologous recombination between the homology sequences A and B.

12. The method of claim 11, wherein the construct contains a further nucleic acid sequence.

13. The method of claim 11, wherein the construct, after said first homology sequence A contains a second recognition sequence for the site-directed induction of DNA double-strand breaks.

14. The method of claim 11, wherein the construct contains at least one of the elements selected from the group consisting of selection markers, reporter genes, replication origins, multiple cloning regions, border sequences for *Agrobacterium transfection*, sequences which enable homologous recombination or insertion into a genome of a host organism, expression cassette for an enzyme suitable for inducing DNA double-strand breaks at the recognition sequence for the site-directed induction of DNA double-strand breaks and combinations thereof.

15. The method of claim 11, wherein the enzyme is selected from the group consisting of restriction endonucleases, homing endonucleases, recombinases, transposases, chimeric nucleases and combinations thereof.

16. The method of claim 11, wherein the enzyme is selected from the group consisting of F-SceI, F-SCeII, F-SuvI, F-TevI, F-TevII, I-AmaI, I-AniI, I-CeuI, I-CeuAIIP, I-ChuI, I-CmoeI, I-CpaI, I-CpaII, I-CreI, I-CrepsbIP, I-CrepsbIIP, I-CrepsbIIIP, I-CrepsbIVP, I-CsmI, I-Cvul, I-CvuAIP, I-DdiI, I-DdiII, I-DirI, I-DmoI, I-HmuI, I-HmuII, I-HspNIP, I-LlaI, I-MsoI, I-NaaI, I-NanI, I-Nc1IP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PpbIP, I-PpoI, I-SPBetaIP, I-ScaI, I-SceI, I-SceII, I-SceIII, I-SceIV, I-SceV, I-SceVI, I-SceVII, I-SexIP, I-SneIP, I-SpomCP, I-SpomIP, I-SpomIIP, I-SquIP, I-Ssp6803I, I-SthPhiJP, I-SthPhiST3P, I-SthPhiS3bP, I-TdeIP, I-TevI, I-TevII, I-TevIII, I-UarAP, I-UarHGPA1P, I-UarHGPA13P, I-VinIP, I-ZbiIP, PI-MtuI, PI-MtuHIP, PI-MtuHIIP, PI-PfuI, PI-PfuII, PI-PkoI, PI-PkoII, PI-PspI, PI-Rma43812IP, PI-SPBetaIP, PI-SceI, PI-TfuI, PI-TfuII, PI-ThyI, PI-TliI, PI-TliII, and combinations thereof.

17. The method of claim 11, wherein the enzyme is selected from the group consisting of enzymes that contain the sequence as shown in SEQ ID NO: 2, 4, 6, 8 or 10, and combinations thereof.

18. The method of claim 11, wherein the enzyme is encoded in an expression cassette.

19. The method of claim 11, wherein the nucleic acid sequence comprises the sequence as shown in SEQ ID NO: 1, 3, 5, 7 or 9, or a combination thereof.

20. An organism comprising the recombination system of claim 1.

21. The organism of claim 20 selected from the group consisting of yeasts, algae, fungi and animal and plant organisms.

22. The organism of claim 21, wherein the plant organism is selected from the group consisting of *Arabidopsis thaliana*, tobacco, wheat, rye, barley, oats, oilseed rape, maize, potato, sugar beet, soybean, sunflower, pumpkin, squash, and peanut.

23. A cell, cell culture, organ, tissue, part or transgenic propagation material comprising the recombination system of claim 1.

24. The system of claim 2, wherein the further nucleic acid sequence comprises an expression cassette for an enzyme suitable for inducing DNA double-strand breaks at the recognition sequence for the site-directed induction of DNA double-strand breaks.

25. The system of claim 1, wherein the construct further comprises an expression cassette for an enzyme suitable for inducing DNA double-strand breaks at the recognition sequence for the site-directed induction of DNA double-strand breaks.

26. The method of claim 12, wherein the further nucleic acid sequence comprises an expression cassette for an enzyme suitable for inducing DNA double-strand breaks at the recognition sequence for the site-directed induction of DNA double-strand breaks.

27. The method of claim 11, wherein the construct comprises an expression cassette for an enzyme suitable for inducing DNA double-strand breaks at the recognition sequence for the site-directed induction of DNA double-strand breaks.

28. The recombination system of claim 1, wherein the eukaryotic organism is a plant organism.

29. The method of claim 11, wherein the eukaryotic cell or organism is a plant cell or plant organism.

* * * * *

UNITED STATES PATENT AND TRADEMARK OFFICE
CERTIFICATE OF CORRECTION

PATENT NO. : 7,736,886 B2
APPLICATION NO. : 10/750891
DATED : June 15, 2010
INVENTOR(S) : Holger Puchta et al.

It is certified that error appears in the above-identified patent and that said Letters Patent is hereby corrected as shown below:

In the claims:

In Claim 16, in column 73, on line 39, "I-CrepsbIIP, I-CrepsbIIIp, I-CrepsbIVP, I-CsmI, I-Cvu1," should read -- I-CrepsbIIP, I-CrepsbIIIP, I-CrepsbIVP, I-CsmI, I-CvuI, --.

Signed and Sealed this
Thirteenth Day of November, 2012

David J. Kappos
*Director of the United States Patent and Trademark Office*

SEQUENCE LISTING

<160> NUMBER OF SEQ ID NOS: 30

<210> SEQ ID NO 1
<211> LENGTH: 788
<212> TYPE: DNA
<213> ORGANISM: Saccharomyces cerevisiae
<220> FEATURE:
<221> NAME/KEY: CDS
<222> LOCATION: (62)..(766)
<223> OTHER INFORMATION: open reading frame coding for I-SceI

<400> SEQUENCE: 1

```
ggatccagta ctgtacctag aatacaaaga agaggaagaa gaaacctcta cagaagaagt       60 g atg aaa aac atc aaa aaa aac cag gta atg aac ctg ggt ccg aac tct      109
  Met Lys Asn Ile Lys Lys Asn Gln Val Met Asn Leu Gly Pro Asn Ser
    1               5                  10                  15 aaa ctg ctg aaa gaa tac aaa tcc cag ctg atc gaa ctg aac atc gaa        157
Lys Leu Leu Lys Glu Tyr Lys Ser Gln Leu Ile Glu Leu Asn Ile Glu
                20                  25                  30 cag ttc gaa gca ggt atc ggt ctg atc ctg ggt gat gct tac atc cgt        205
Gln Phe Glu Ala Gly Ile Gly Leu Ile Leu Gly Asp Ala Tyr Ile Arg
            35                  40                  45 tct cgt gat gaa ggt aaa acc tac tgt atg cag ttc gag tgg aaa aac        253
Ser Arg Asp Glu Gly Lys Thr Tyr Cys Met Gln Phe Glu Trp Lys Asn
        50                  55                  60 aaa gca tac atg gac cac gta tgt ctg ctg tac gat cag tgg gta ctg        301
Lys Ala Tyr Met Asp His Val Cys Leu Leu Tyr Asp Gln Trp Val Leu
    65                  70                  75                  80 tcc ccg ccg cac aaa aaa gaa cgt gtt aac cac ctg ggt aac ctg gta        349
Ser Pro Pro His Lys Lys Glu Arg Val Asn His Leu Gly Asn Leu Val
                85                  90                  95 atc acc tgg ggc gcc cag act ttc aaa cac caa gct ttc aac aaa ctg        397
Ile Thr Trp Gly Ala Gln Thr Phe Lys His Gln Ala Phe Asn Lys Leu
               100                 105                 110 gct agc ctg ttc atc gtt aac aac aaa aaa acc atc ccg aac aac ctg        445
Ala Ser Leu Phe Ile Val Asn Asn Lys Lys Thr Ile Pro Asn Asn Leu
           115                 120                 125 gtt gaa aac tac ctg acc ccg atg tct ctg gca tac tgg ttc atg gat        493
Val Glu Asn Tyr Leu Thr Pro Met Ser Leu Ala Tyr Trp Phe Met Asp
       130                 135                 140 gat ggt ggt aaa tgg gat tac aac aaa aac tct acc aac aaa tcg atc        541
Asp Gly Gly Lys Trp Asp Tyr Asn Lys Asn Ser Thr Asn Lys Ser Ile
145                 150                 155                 160 gta ctg aac acc cag tct ttc act ttc gaa gaa gta gaa tac ctg gtt        589
Val Leu Asn Thr Gln Ser Phe Thr Phe Glu Glu Val Glu Tyr Leu Val
                165                 170                 175 aag ggt ctg cgt aac aaa ttc caa ctg aac tgt tac cta aaa atc aac        637
Lys Gly Leu Arg Asn Lys Phe Gln Leu Asn Cys Tyr Leu Lys Ile Asn
            180                 185                 190 aaa aac aaa ccg atc atc tac atc gat tct atg tct tac ctg atc ttc        685
Lys Asn Lys Pro Ile Ile Tyr Ile Asp Ser Met Ser Tyr Leu Ile Phe
        195                 200                 205 tac aac ctg atc aaa ccg tac ctg atc ccg cag atg atg tac aaa ctg        733
Tyr Asn Leu Ile Lys Pro Tyr Leu Ile Pro Gln Met Met Tyr Lys Leu
```

```
                 210                 215                 220
ccg aac act atc tcc tcc gaa act ttc ctg aaa taataagtcg agtactggat    786
Pro Asn Thr Ile Ser Ser Glu Thr Phe Leu Lys
225                 230                 235 cc                                                                   788
```

<210> SEQ ID NO 2
<211> LENGTH: 235
<212> TYPE: PRT
<213> ORGANISM: Saccharomyces cerevisiae

<400> SEQUENCE: 2

```
Met Lys Asn Ile Lys Lys Asn Gln Val Met Asn Leu Gly Pro Asn Ser
 1               5                  10                  15

Lys Leu Leu Lys Glu Tyr Lys Ser Gln Leu Ile Glu Leu Asn Ile Glu
                20                  25                  30

Gln Phe Glu Ala Gly Ile Gly Leu Ile Leu Gly Asp Ala Tyr Ile Arg
            35                  40                  45

Ser Arg Asp Glu Gly Lys Thr Tyr Cys Met Gln Phe Glu Trp Lys Asn
        50                  55                  60

Lys Ala Tyr Met Asp His Val Cys Leu Leu Tyr Asp Gln Trp Val Leu
65                  70                  75                  80

Ser Pro Pro His Lys Lys Glu Arg Val Asn His Leu Gly Asn Leu Val
                85                  90                  95

Ile Thr Trp Gly Ala Gln Thr Phe Lys His Gln Ala Phe Asn Lys Leu
            100                 105                 110

Ala Ser Leu Phe Ile Val Asn Asn Lys Lys Thr Ile Pro Asn Asn Leu
        115                 120                 125

Val Glu Asn Tyr Leu Thr Pro Met Ser Leu Ala Tyr Trp Phe Met Asp
130                 135                 140

Asp Gly Gly Lys Trp Asp Tyr Asn Lys Asn Ser Thr Asn Lys Ser Ile
145                 150                 155                 160

Val Leu Asn Thr Gln Ser Phe Thr Phe Glu Glu Val Glu Tyr Leu Val
                165                 170                 175

Lys Gly Leu Arg Asn Lys Phe Gln Leu Asn Cys Tyr Leu Lys Ile Asn
            180                 185                 190

Lys Asn Lys Pro Ile Ile Tyr Ile Asp Ser Met Ser Tyr Leu Ile Phe
        195                 200                 205

Tyr Asn Leu Ile Lys Pro Tyr Leu Ile Pro Gln Met Met Tyr Lys Leu
210                 215                 220

Pro Asn Thr Ile Ser Ser Glu Thr Phe Leu Lys
225                 230                 235
```

<210> SEQ ID NO 3
<211> LENGTH: 746
<212> TYPE: DNA
<213> ORGANISM: Chlamydomonas applanata
<220> FEATURE:
<221> NAME/KEY: CDS
<222> LOCATION: (54)..(737)
<223> OTHER INFORMATION: open reading frame of I-ChuI with nuclear
      location signal
<220> FEATURE:
<221> NAME/KEY: misc_feature
<222> LOCATION: (54)..(83)
<223> OTHER INFORMATION: coding for nuclear location signal

<400> SEQUENCE: 3

```
ctcgagtacc tagaatacaa agaagaggaa gaagaaactc tatagaagaa gcc atg       56
```

|                                                                 | Met |     |
|                                                                 | 1   |     |
| ggt cca aag aaa aag aga aag gtt atc atg tca tta aca caa caa caa | 104 |
| Gly Pro Lys Lys Lys Arg Lys Val Ile Met Ser Leu Thr Gln Gln Gln |     |
|         5               10              15                      |     |
| aaa gac tta att ttc gga tct cta ctg ggt gat gga aat tta caa act | 152 |
| Lys Asp Leu Ile Phe Gly Ser Leu Leu Gly Asp Gly Asn Leu Gln Thr |     |
|         20              25              30                      |     |
| ggt tca gta ggt agg act tgg cgc tat cga gcg ctc cat aaa agt gag | 200 |
| Gly Ser Val Gly Arg Thr Trp Arg Tyr Arg Ala Leu His Lys Ser Glu |     |
|         35              40              45                      |     |
| cat cag aca tac tta ttt cat aag tat gaa atc tta aag ccg ctt tgt | 248 |
| His Gln Thr Tyr Leu Phe His Lys Tyr Glu Ile Leu Lys Pro Leu Cys |     |
| 50              55              60              65              |     |
| ggc gaa aat act ctc cca aca gaa agt ata gtg ttc gac gaa aga aca | 296 |
| Gly Glu Asn Thr Leu Pro Thr Glu Ser Ile Val Phe Asp Glu Arg Thr |     |
|         70              75              80                      |     |
| aac aag gag gtt aaa cgt tgg ttt ttc aac aca tta acc aat cct tcc | 344 |
| Asn Lys Glu Val Lys Arg Trp Phe Phe Asn Thr Leu Thr Asn Pro Ser |     |
|         85              90              95                      |     |
| tta aaa ttc ttc gca gac atg ttc tac aca tat gac caa aac aca caa | 392 |
| Leu Lys Phe Phe Ala Asp Met Phe Tyr Thr Tyr Asp Gln Asn Thr Gln |     |
|         100             105             110                     |     |
| aaa tgg gtt aaa gat gta cct gta aag gtt caa aca ttc tta act cct | 440 |
| Lys Trp Val Lys Asp Val Pro Val Lys Val Gln Thr Phe Leu Thr Pro |     |
|         115             120             125                     |     |
| caa gct tta gca tac ttt tat ata gac gat gga gcg tta aaa tgg ctt | 488 |
| Gln Ala Leu Ala Tyr Phe Tyr Ile Asp Asp Gly Ala Leu Lys Trp Leu |     |
| 130             135             140             145             |     |
| aat aag tct aac gct atg caa att tgt act gaa agt ttc agt caa ggg | 536 |
| Asn Lys Ser Asn Ala Met Gln Ile Cys Thr Glu Ser Phe Ser Gln Gly |     |
|             150             155             160                 |     |
| ggc acg att cgg atc caa aaa gca cta aaa acg ctc tat aat att gat | 584 |
| Gly Thr Ile Arg Ile Gln Lys Ala Leu Lys Thr Leu Tyr Asn Ile Asp |     |
|         165             170             175                     |     |
| aca acg ttg aca aaa aaa act cta caa gac ggc aga att ggc tat cgt | 632 |
| Thr Thr Leu Thr Lys Lys Thr Leu Gln Asp Gly Arg Ile Gly Tyr Arg |     |
|         180             185             190                     |     |
| ata gct att cct gaa gcc agt agc ggt gct ttt cgt gaa gtc att aaa | 680 |
| Ile Ala Ile Pro Glu Ala Ser Ser Gly Ala Phe Arg Glu Val Ile Lys |     |
|         195             200             205                     |     |
| cct ttt cta gtt gat tgt atg aga tac aaa gtt tct gat ggc aat aaa | 728 |
| Pro Phe Leu Val Asp Cys Met Arg Tyr Lys Val Ser Asp Gly Asn Lys |     |
| 210             215             220             225             |     |
| ggc cac ctt tagctcgag                                           | 746 |
| Gly His Leu                                                     |     |

<210> SEQ ID NO 4
<211> LENGTH: 228
<212> TYPE: PRT
<213> ORGANISM: Chlamydomonas applanata

<400> SEQUENCE: 4

Met Gly Pro Lys Lys Lys Arg Lys Val Ile Met Ser Leu Thr Gln Gln
1               5                   10                  15

Gln Lys Asp Leu Ile Phe Gly Ser Leu Leu Gly Asp Gly Asn Leu Gln
                20                  25                  30

Thr Gly Ser Val Gly Arg Thr Trp Arg Tyr Arg Ala Leu His Lys Ser
            35                  40                  45

```
Glu His Gln Thr Tyr Leu Phe His Lys Tyr Glu Ile Leu Lys Pro Leu
 50                  55                  60

Cys Gly Glu Asn Thr Leu Pro Thr Glu Ser Ile Val Phe Asp Glu Arg
 65                  70                  75                  80

Thr Asn Lys Glu Val Lys Arg Trp Phe Asn Thr Leu Thr Asn Pro
                 85                  90                  95

Ser Leu Lys Phe Phe Ala Asp Met Phe Tyr Thr Tyr Asp Gln Asn Thr
                100                 105                 110

Gln Lys Trp Val Lys Asp Val Pro Val Lys Val Gln Thr Phe Leu Thr
            115                 120                 125

Pro Gln Ala Leu Ala Tyr Phe Tyr Ile Asp Asp Gly Ala Leu Lys Trp
130                 135                 140

Leu Asn Lys Ser Asn Ala Met Gln Ile Cys Thr Glu Ser Phe Ser Gln
145                 150                 155                 160

Gly Gly Thr Ile Arg Ile Gln Lys Ala Leu Lys Thr Leu Tyr Asn Ile
                165                 170                 175

Asp Thr Thr Leu Thr Lys Lys Thr Leu Gln Asp Gly Arg Ile Gly Tyr
                180                 185                 190

Arg Ile Ala Ile Pro Glu Ala Ser Ser Gly Ala Phe Arg Glu Val Ile
            195                 200                 205

Lys Pro Phe Leu Val Asp Cys Met Arg Tyr Lys Val Ser Asp Gly Asn
210                 215                 220

Lys Gly His Leu
225

<210> SEQ ID NO 5
<211> LENGTH: 582
<212> TYPE: DNA
<213> ORGANISM: Chlamydomonas reinhardtii
<220> FEATURE:
<221> NAME/KEY: CDS
<222> LOCATION: (55)..(573)
<223> OTHER INFORMATION: openreading frame coding for I-CreI with
      nuclear location signal
<220> FEATURE:
<221> NAME/KEY: misc_feature
<222> LOCATION: (55)..(84)
<223> OTHER INFORMATION: coding for nuclear location signal

<400> SEQUENCE: 5
ctcgagtacc tagaatacaa agaagaggaa gagaaacctc taccagaaga agcc atg      57
                                                              Met
                                                              1 ggt cca aag aaa aag aga aag gtt atc atg aat aca aaa tat aat aaa    105
Gly Pro Lys Lys Lys Arg Lys Val Ile Met Asn Thr Lys Tyr Asn Lys
         5                  10                  15 gag ttc tta ctc tac tta gca ggg ttt gta gac ggt gac ggt agc ata    153
Glu Phe Leu Leu Tyr Leu Ala Gly Phe Val Asp Gly Asp Gly Ser Ile
             20                  25                  30 atc gct caa att aag cct aat cag tct tat aaa ttt aag cat cag cta    201
Ile Ala Gln Ile Lys Pro Asn Gln Ser Tyr Lys Phe Lys His Gln Leu
         35                  40                  45 tca ctc gcg ttc caa gtc acg caa aag aca cag aga cgt tgg ttt tta    249
Ser Leu Ala Phe Gln Val Thr Gln Lys Thr Gln Arg Arg Trp Phe Leu
 50                  55                  60                  65 gac aaa tta gtg gat gaa att ggg gtt ggt tat gta aga gat agg ggt    297
Asp Lys Leu Val Asp Glu Ile Gly Val Gly Tyr Val Arg Asp Arg Gly
                 70                  75                  80 agc gtt tcg gat tat att cta agc gaa atc aag cct ttg cat aat ttt    345
Ser Val Ser Asp Tyr Ile Leu Ser Glu Ile Lys Pro Leu His Asn Phe
```

```
                   85                  90                  95
tta aca caa cta caa cct ttt cta aaa cta aaa caa aaa caa gca aat    393
Leu Thr Gln Leu Gln Pro Phe Leu Lys Leu Lys Gln Lys Gln Ala Asn
            100                 105                 110 tta gtt tta aaa att att gaa caa ctt ccg tca gca aaa gaa tcc ccg    441
Leu Val Leu Lys Ile Ile Glu Gln Leu Pro Ser Ala Lys Glu Ser Pro
    115                 120                 125 gac aaa ttc tta gaa gtt tgt aca tgg gtg gat caa att gca gct ctg    489
Asp Lys Phe Leu Glu Val Cys Thr Trp Val Asp Gln Ile Ala Ala Leu
130                 135                 140                 145 aat gat tcg aag acg cgt aaa aca act tct gaa acc gtt cgt gct gtg    537
Asn Asp Ser Lys Thr Arg Lys Thr Thr Ser Glu Thr Val Arg Ala Val
                150                 155                 160 cta gac agt tta agt gaa aaa aag aaa tcg tcc ccg tagctcgag          582
Leu Asp Ser Leu Ser Glu Lys Lys Lys Ser Ser Pro
                165                 170
```

<210> SEQ ID NO 6
<211> LENGTH: 173
<212> TYPE: PRT
<213> ORGANISM: Chlamydomonas reinhardtii

<400> SEQUENCE: 6

```
Met Gly Pro Lys Lys Arg Lys Val Ile Met Asn Thr Lys Tyr Asn
  1               5                  10                  15

Lys Glu Phe Leu Leu Tyr Leu Ala Gly Phe Val Asp Gly Asp Gly Ser
                20                  25                  30

Ile Ile Ala Gln Ile Lys Pro Asn Gln Ser Tyr Lys Phe Lys His Gln
            35                  40                  45

Leu Ser Leu Ala Phe Gln Val Thr Gln Lys Thr Gln Arg Arg Trp Phe
        50                  55                  60

Leu Asp Lys Leu Val Asp Glu Ile Gly Val Gly Tyr Val Arg Asp Arg
    65                  70                  75                  80

Gly Ser Val Ser Asp Tyr Ile Leu Ser Glu Ile Lys Pro Leu His Asn
                85                  90                  95

Phe Leu Thr Gln Leu Gln Pro Phe Leu Lys Leu Lys Gln Lys Gln Ala
            100                 105                 110

Asn Leu Val Leu Lys Ile Ile Glu Gln Leu Pro Ser Ala Lys Glu Ser
        115                 120                 125

Pro Asp Lys Phe Leu Glu Val Cys Thr Trp Val Asp Gln Ile Ala Ala
    130                 135                 140

Leu Asn Asp Ser Lys Thr Arg Lys Thr Thr Ser Glu Thr Val Arg Ala
145                 150                 155                 160

Val Leu Asp Ser Leu Ser Glu Lys Lys Lys Ser Ser Pro
                165                 170
```

<210> SEQ ID NO 7
<211> LENGTH: 546
<212> TYPE: DNA
<213> ORGANISM: Chlamydomonas segnis
<220> FEATURE:
<221> NAME/KEY: CDS
<222> LOCATION: (52)..(537)
<223> OTHER INFORMATION: open readings frame coding for I-CpaI with
      nuclear location signal
<220> FEATURE:
<221> NAME/KEY: misc_feature
<222> LOCATION: (52)..(81)
<223> OTHER INFORMATION: coding for nuclear location signal

<400> SEQUENCE: 7

```
ctcgagtacc tagaatacaa gaagagaaga agaacctcta cagaagaagc c atg ggt      57
                                                        Met Gly
                                                          1 cca aag aaa aag aga aag gtt atc atg gac att aat cct caa tgg att     105
Pro Lys Lys Lys Arg Lys Val Ile Met Asp Ile Asn Pro Gln Trp Ile
         5                  10                  15 aca ggt ttc gta gat ggg gaa ggt tgt ttt agt gta agt att ctt aga     153
Thr Gly Phe Val Asp Gly Glu Gly Cys Phe Ser Val Ser Ile Leu Arg
     20                  25                  30 aat aat tcg ttg cgc tat ggc cat cag ctt caa cca gaa ttc gta gtg     201
Asn Asn Ser Leu Arg Tyr Gly His Gln Leu Gln Pro Glu Phe Val Val
 35                  40                  45                  50 acc caa cat aaa tta gat gca aat gtt tta tat gca tta aaa gac tac     249
Thr Gln His Lys Leu Asp Ala Asn Val Leu Tyr Ala Leu Lys Asp Tyr
             55                  60                  65 ttt aaa gtt gga tca gtc gtt gtg aat cat ggg gaa cgg ctt tgc tat     297
Phe Lys Val Gly Ser Val Val Val Asn His Gly Glu Arg Leu Cys Tyr
                 70                  75                  80 aaa gtc aaa aat att gat cac ttt ata acc gtc att ata cca ttt ttc     345
Lys Val Lys Asn Ile Asp His Phe Ile Thr Val Ile Ile Pro Phe Phe
             85                  90                  95 gaa aaa cat gag cta aaa aca aaa aga aga att gaa ttt ctt cga ttt     393
Glu Lys His Glu Leu Lys Thr Lys Arg Arg Ile Glu Phe Leu Arg Phe
        100                 105                 110 cga aaa atc tgc ttg ctg tta aaa gca ggt aga cat tta gaa tcg cag     441
Arg Lys Ile Cys Leu Leu Leu Lys Ala Gly Arg His Leu Glu Ser Gln
115                 120                 125                 130 gaa gga ttc gag aaa gtg ttg gat tta gca aaa aaa ctc cgt atc aat     489
Glu Gly Phe Glu Lys Val Leu Asp Leu Ala Lys Lys Leu Arg Ile Asn
                135                 140                 145 gag aaa aac tac cag gaa tct atc aaa cgt ttt gaa gaa act ggc gag     537
Glu Lys Asn Tyr Gln Glu Ser Ile Lys Arg Phe Glu Glu Thr Gly Glu
            150                 155                 160 taactcgag                                                           546

<210> SEQ ID NO 8
<211> LENGTH: 162
<212> TYPE: PRT
<213> ORGANISM: Chlamydomonas segnis

<400> SEQUENCE: 8

Met Gly Pro Lys Lys Lys Arg Lys Val Ile Met Asp Ile Asn Pro Gln
  1               5                  10                  15

Trp Ile Thr Gly Phe Val Asp Gly Glu Gly Cys Phe Ser Val Ser Ile
             20                  25                  30

Leu Arg Asn Asn Ser Leu Arg Tyr Gly His Gln Leu Gln Pro Glu Phe
         35                  40                  45

Val Val Thr Gln His Lys Leu Asp Ala Asn Val Leu Tyr Ala Leu Lys
     50                  55                  60

Asp Tyr Phe Lys Val Gly Ser Val Val Val Asn His Gly Glu Arg Leu
 65                  70                  75                  80

Cys Tyr Lys Val Lys Asn Ile Asp His Phe Ile Thr Val Ile Ile Pro
                 85                  90                  95

Phe Phe Glu Lys His Glu Leu Lys Thr Lys Arg Arg Ile Glu Phe Leu
            100                 105                 110

Arg Phe Arg Lys Ile Cys Leu Leu Leu Lys Ala Gly Arg His Leu Glu
        115                 120                 125
```

-continued

```
Ser Gln Glu Gly Phe Glu Lys Val Leu Asp Leu Ala Lys Lys Leu Arg
    130                 135                 140

Ile Asn Glu Lys Asn Tyr Gln Glu Ser Ile Lys Arg Phe Glu Glu Thr
145                 150                 155                 160

Gly Glu

<210> SEQ ID NO 9
<211> LENGTH: 793
<212> TYPE: DNA
<213> ORGANISM: Chlamydomonas segnis
<220> FEATURE:
<221> NAME/KEY: CDS
<222> LOCATION: (53)..(784)
<223> OTHER INFORMATION: open reading frame coding for I-CpaII with
      nuclear location signal
<220> FEATURE:
<221> NAME/KEY: misc_feature
<222> LOCATION: (53)..(82)
<223> OTHER INFORMATION: coding for nuclear location signal

<400> SEQUENCE: 9
ctcgagtacc tagaaacaaa gaagaggaag aagaaactct acagaagaag cc atg ggt     58
                                                          Met Gly
                                                          1 cca aag aaa aag aga aag gtt atc atg acc gat tct aaa tct aga aac     106
Pro Lys Lys Lys Arg Lys Val Ile Met Thr Asp Ser Lys Ser Arg Asn
        5                   10                  15 aac aat aat ttt tta agc aat aat ctt tta cct ttg acc gat gac gag     154
Asn Asn Asn Phe Leu Ser Asn Asn Leu Leu Pro Leu Thr Asp Asp Glu
    20                  25                  30 aag gct tta att gcg ggg aca ctt tta ggg gat gct cat att caa aag     202
Lys Ala Leu Ile Ala Gly Thr Leu Leu Gly Asp Ala His Ile Gln Lys
 35                  40                  45                  50 cgt ggt gat agc tat agg cta aaa ata gct cat ggc ttg gat cat gaa     250
Arg Gly Asp Ser Tyr Arg Leu Lys Ile Ala His Gly Leu Asp His Glu
                55                  60                  65 gag ctt gtc gtc tgg aag tat aac cgt tta atc agg ttg tgt caa aca     298
Glu Leu Val Val Trp Lys Tyr Asn Arg Leu Ile Arg Leu Cys Gln Thr
        70                  75                  80 aca caa ccc cca agg gtg gaa acc tac tca aca aag tta aag tct ggc     346
Thr Gln Pro Pro Arg Val Glu Thr Tyr Ser Thr Lys Leu Lys Ser Gly
    85                  90                  95 gta ttg cct caa ggg gtt gtt ttc tat acc tcg tcc gga aag tat tta     394
Val Leu Pro Gln Gly Val Val Phe Tyr Thr Ser Ser Gly Lys Tyr Leu
100                 105                 110 aaa gag act tat gac ctt ttt tat aaa caa act gca gac ggt cgg agg     442
Lys Glu Thr Tyr Asp Leu Phe Tyr Lys Gln Thr Ala Asp Gly Arg Arg
115                 120                 125                 130 gta aaa aca ata aca cag gag ttg atc gac agt tta ccc aag cat cca     490
Val Lys Thr Ile Thr Gln Glu Leu Ile Asp Ser Leu Pro Lys His Pro
                135                 140                 145 ttg gtc tta gca gcc ttt ttt atg gac gat ggt agt gtt cgg tcc gac     538
Leu Val Leu Ala Ala Phe Phe Met Asp Asp Gly Ser Val Arg Ser Asp
        150                 155                 160 tgt tat tca gga aag att gca acg cca ggg ttt gct ggt aaa gaa gaa     586
Cys Tyr Ser Gly Lys Ile Ala Thr Pro Gly Phe Ala Gly Lys Glu Glu
    165                 170                 175 agc cag ttg ttg tgt aac tat cta cac agt tgg gat gtt caa gca aac     634
Ser Gln Leu Leu Cys Asn Tyr Leu His Ser Trp Asp Val Gln Ala Asn
180                 185                 190 gta gtt gct cat aaa aaa gca aac aat cag tat tac att ggg ctc cca     682
Val Val Ala His Lys Lys Ala Asn Asn Gln Tyr Tyr Ile Gly Leu Pro
```

```
                 195                 200                 205                 210
gca aaa aca ttt ggt cgc ttt att aac att att gaa ccc tac gtt aga           730
Ala Lys Thr Phe Gly Arg Phe Ile Asn Ile Ile Glu Pro Tyr Val Arg
                215                 220                 225 gaa gtt cct gct tta tgt tat aaa tta aac gaa tca aga aaa ccc cgt           778
Glu Val Pro Ala Leu Cys Tyr Lys Leu Asn Glu Ser Arg Lys Pro Arg
                230                 235                 240 aac gac tgactcgag                                                          793
Asn Asp <210> SEQ ID NO 10
<211> LENGTH: 244
<212> TYPE: PRT
<213> ORGANISM: Chlamydomonas segnis

<400> SEQUENCE: 10

Met Gly Pro Lys Lys Arg Lys Val Ile Met Thr Asp Ser Lys Ser
 1               5                  10                  15

Arg Asn Asn Asn Phe Leu Ser Asn Asn Leu Leu Pro Leu Thr Asp
                20                  25                  30

Asp Glu Lys Ala Leu Ile Ala Gly Thr Leu Leu Gly Asp Ala His Ile
                35                  40                  45

Gln Lys Arg Gly Asp Ser Tyr Arg Leu Lys Ile Ala His Gly Leu Asp
        50                  55                  60

His Glu Glu Leu Val Val Trp Lys Tyr Asn Arg Leu Ile Arg Leu Cys
65                  70                  75                  80

Gln Thr Thr Gln Pro Pro Arg Val Glu Thr Tyr Ser Thr Lys Leu Lys
                85                  90                  95

Ser Gly Val Leu Pro Gln Gly Val Phe Tyr Thr Ser Gly Lys
                100                 105                 110

Tyr Leu Lys Glu Thr Tyr Asp Leu Phe Tyr Lys Gln Thr Ala Asp Gly
                115                 120                 125

Arg Arg Val Lys Thr Ile Thr Gln Glu Leu Ile Asp Ser Leu Pro Lys
        130                 135                 140

His Pro Leu Val Leu Ala Ala Phe Phe Met Asp Asp Gly Ser Val Arg
145                 150                 155                 160

Ser Asp Cys Tyr Ser Gly Lys Ile Ala Thr Pro Gly Phe Ala Gly Lys
                165                 170                 175

Glu Glu Ser Gln Leu Leu Cys Asn Tyr Leu His Ser Trp Asp Val Gln
                180                 185                 190

Ala Asn Val Val Ala His Lys Lys Ala Asn Asn Gln Tyr Tyr Ile Gly
        195                 200                 205

Leu Pro Ala Lys Thr Phe Gly Arg Phe Ile Asn Ile Ile Glu Pro Tyr
        210                 215                 220

Val Arg Glu Val Pro Ala Leu Cys Tyr Lys Leu Asn Glu Ser Arg Lys
225                 230                 235                 240

Pro Arg Asn Asp

<210> SEQ ID NO 11
<211> LENGTH: 35
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 11
```

```
cggctcgagc tacggggacg atttctttttt ttcac                               35
```

<210> SEQ ID NO 12
<211> LENGTH: 120
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 12

```
cggctcgagt acctagaata caaagaagag gaagaagaaa cctctacaga agaagccatg      60
ggtccaaaga aaagagaaa ggttatcatg aatacaaat ataataaga gttcttactc        120
```

<210> SEQ ID NO 13
<211> LENGTH: 116
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 13

```
cggctcgagt acctagaata caaagaagag gaagaagaaa cctctacaga agaagccatg      60
ggtccaaaga aaagagaaa ggttatcatg gacattaatc ctcaatggat tacagg         116
```

<210> SEQ ID NO 14
<211> LENGTH: 33
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 14

```
cggctcgagt tactcgccag tttcttcaaa acg                                  33
```

<210> SEQ ID NO 15
<211> LENGTH: 114
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 15

```
cggctcgagt acctagaata caaagaagag gaagaagaaa cctctacaga agaagccatg      60
ggtccaaaga aaagagaaa ggttatcatg accgattcta atctagaaa caac            114
```

<210> SEQ ID NO 16
<211> LENGTH: 35
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 16

```
cggctcgagc taaaggtggc ctttattgcc atcag                                35
```

<210> SEQ ID NO 17
<211> LENGTH: 114
<212> TYPE: DNA
<213> ORGANISM: Artificial Sequence
<220> FEATURE:

-continued

```
<223> OTHER INFORMATION: Description of the artificial sequence:
      oligonucleotide primer

<400> SEQUENCE: 17
cggctcgagt acctagaata caaagaagag gaagaagaaa cctctacaga agaagccatg    60
ggtccaaaga aaagagaaa ggttatcatg tcattaacac aacaacaaaa agac          114

<210> SEQ ID NO 18
<211> LENGTH: 35
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 18
cggctcgagc taaaggtggc ctttattgcc atcag                               35

<210> SEQ ID NO 19
<211> LENGTH: 66
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 19
cggctctaga gcggccgcct agggataaca gggtaataga atcccacaaa aatctgagct    60
taacag                                                              66

<210> SEQ ID NO 20
<211> LENGTH: 65
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 20
cggctctaga ctattaccct gttatcccta ggcccgatct agtaacatag atgacaccgc    60
gcgcg                                                               65

<210> SEQ ID NO 21
<211> LENGTH: 34
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 21
cggaagcttc gtcaccaatc ccaattcgat ctac                                34

<210> SEQ ID NO 22
<211> LENGTH: 34
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 22
cggaagcttc cacttgcaaa gtcccgctag tgcc                                34
```

```
<210> SEQ ID NO 23
<211> LENGTH: 34
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 23
cggaagcttc gtcaccaatc ccaattcgat ctac                              34

<210> SEQ ID NO 24
<211> LENGTH: 34
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 24
cggaagcttc cacttgcaaa gtcccgctag tgcc                              34

<210> SEQ ID NO 25
<211> LENGTH: 62
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 25
ctagtacaaa acgtcgtgag acattttaat ctgaaggttt ggcacctcga tgtcggctca   60
tc                                                                 62

<210> SEQ ID NO 26
<211> LENGTH: 62
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 26
ctaggatgag ccgtcatcga ggtgccaaac cttcagatta aaatgtctca cgacgttttg   60
ta                                                                 62

<210> SEQ ID NO 27
<211> LENGTH: 75
<212> TYPE: DNA
<213> ORGANISM: Artificial Sequence
<220> FEATURE:
<223> OTHER INFORMATION: Description of the artificial sequence:
      oligonucleotide primer

<400> SEQUENCE: 27
ctagtccgaa aacgccgtga gacatattgg ttacgatcct aaggtagcga aattcacccg   60
gtaactctgt gccag                                                   75

<210> SEQ ID NO 28
<211> LENGTH: 75
<212> TYPE: DNA
<213> ORGANISM: Artificial Sequence
<220> FEATURE:
<223> OTHER INFORMATION: Description of the artificial sequence:
      oligonucleotide primer
```

-continued

```
<400> SEQUENCE: 28
ctagctggca cagagttacc gggtgaattt cgctacctta ggatcgtaac caatatgtct      60
cacggcgttt tcgga                                                      75

<210> SEQ ID NO 29
<211> LENGTH: 7
<212> TYPE: PRT
<213> ORGANISM: Artificial Sequence
<220> FEATURE:
<223> OTHER INFORMATION: Description of the artificial sequence: nuclear
      location sequence

<400> SEQUENCE: 29

Pro Lys Thr Lys Arg Lys Val
  1               5

<210> SEQ ID NO 30
<211> LENGTH: 7
<212> TYPE: PRT
<213> ORGANISM: Artificial Sequence
<220> FEATURE:
<223> OTHER INFORMATION: Description of the artificial sequence: nuclear
      location sequence

<400> SEQUENCE: 30

Pro Lys Lys Lys Arg Lys Val
  1               5
```